(12) United States Patent
Takeda et al.

(10) Patent No.: US 11,925,109 B2
(45) Date of Patent: Mar. 5, 2024

(54) ORGANIC COMPOUND, LIGHT-EMITTING DEVICE, OPTICAL DEVICE, LIGHT-EMITTING APPARATUS, ELECTRONIC DEVICE, AND LIGHTING DEVICE

(71) Applicant: SEMICONDUCTOR ENERGY LABORATORY CO., LTD., Atsugi (JP)

(72) Inventors: Kyoko Takeda, Kanagawa (JP); Harue Osaka, Kanagawa (JP); Hiroshi Kadoma, Kanagawa (JP); Satoshi Seo, Kanagawa (JP); Tsunenori Suzuki, Kanagawa (JP); Naoaki Hashimoto, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 589 days.

(21) Appl. No.: 17/116,031

(22) Filed: Dec. 9, 2020

(65) Prior Publication Data
US 2021/0184130 A1    Jun. 17, 2021

(30) Foreign Application Priority Data

Dec. 12, 2019    (JP) ................. 2019-224653

(51) Int. Cl.
| | | |
|---|---|---|
| H01L 51/00 | (2006.01) | |
| H10K 85/60 | (2023.01) | |
| C07D 493/04 | (2006.01) | |
| C09K 11/06 | (2006.01) | |
| H10K 50/11 | (2023.01) | |

(52) U.S. Cl.
CPC ......... H10K 85/636 (2023.02); C07D 493/04 (2013.01); C09K 11/06 (2013.01); C09K 2211/1007 (2013.01); C09K 2211/1018 (2013.01); H10K 50/11 (2023.02); H10K 85/6572 (2023.02); H10K 85/6574 (2023.02)

(58) Field of Classification Search
CPC ............ H01L 51/0061; H01L 51/5012; H01L 51/0073; H01L 51/0072; C07D 493/04; C09K 11/06; C09K 2211/1018; C09K 2211/1007
USPC ...................................................... 428/690
See application file for complete search history.

(56) References Cited

U.S. PATENT DOCUMENTS

2019/0393420 A1    12/2019    Takeda et al.
2021/0193930 A1*    6/2021    Takeda .................. C09K 11/06
2021/0347782 A1    11/2021    Takeda et al.

FOREIGN PATENT DOCUMENTS

| CN | 109320480 A | * | 2/2019 |
|---|---|---|---|
| JP | 2017109929 A | * | 6/2017 |
| JP | 2019-085387 A | | 6/2019 |

OTHER PUBLICATIONS

Translation of JP 2017-109929 (patents application 2015-243085), Jun. 22, 2017. (Year: 2017).*
Translation of CN 109320480, Feb. 12, 2019. (Year: 2019).*

* cited by examiner

*Primary Examiner* — Hui H Chin
(74) *Attorney, Agent, or Firm* — Fish & Richardson P.C.

(57) ABSTRACT

A novel organic compound with favorable thermophysical properties is provided. An organic compound represented by General Formula (G1) is provided. At least one of $X^1$ to $X^5$ is a secondary or tertiary alkyl group having 3 to 6 carbon atoms in which a carbon atom bonded to a phenyl group branches. Each of $R^1$ to $R^7$ is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms. $Ar^1$ represents a substituted or unsubstituted condensed heteroaromatic ring skeleton having 8 to 60 carbon atoms and composed of two or more aromatic rings, and $Ar^2$ represents a substituted or unsubstituted aryl group having 6 to 25 carbon atoms. Furthermore, n is any of 1 to 3.

17 Claims, 27 Drawing Sheets

(G1)

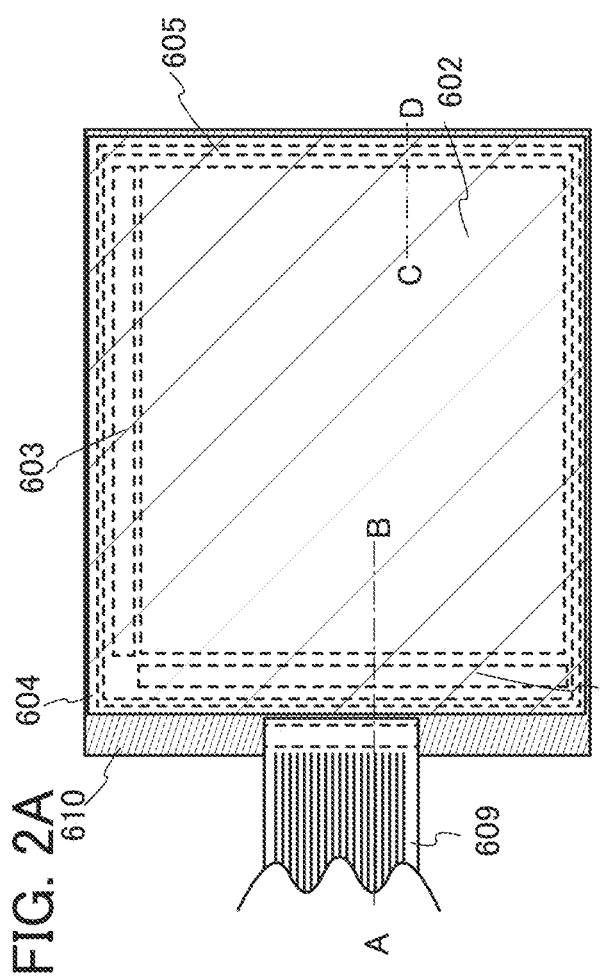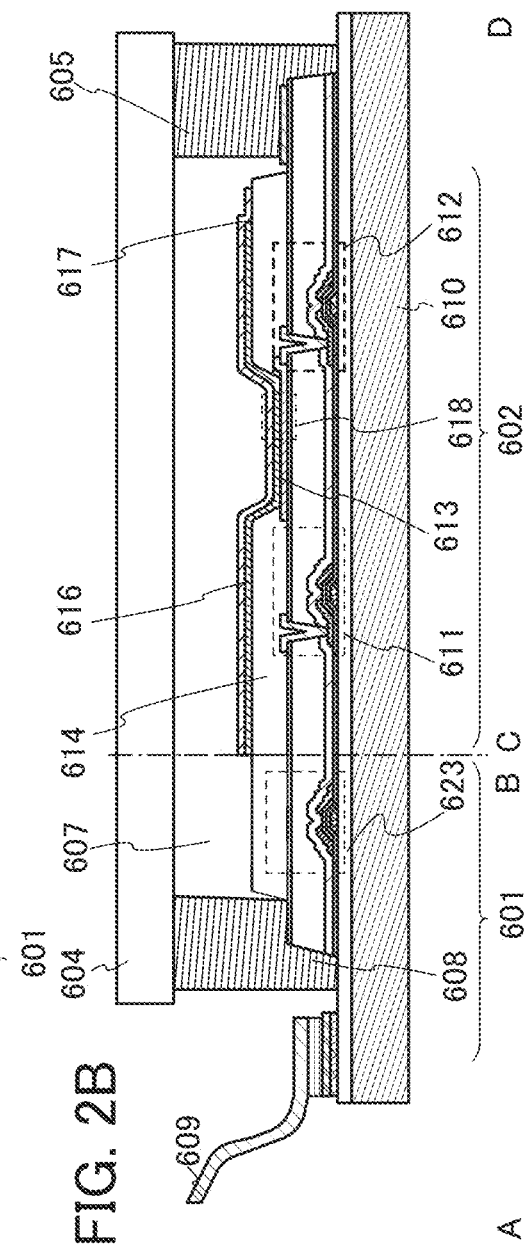

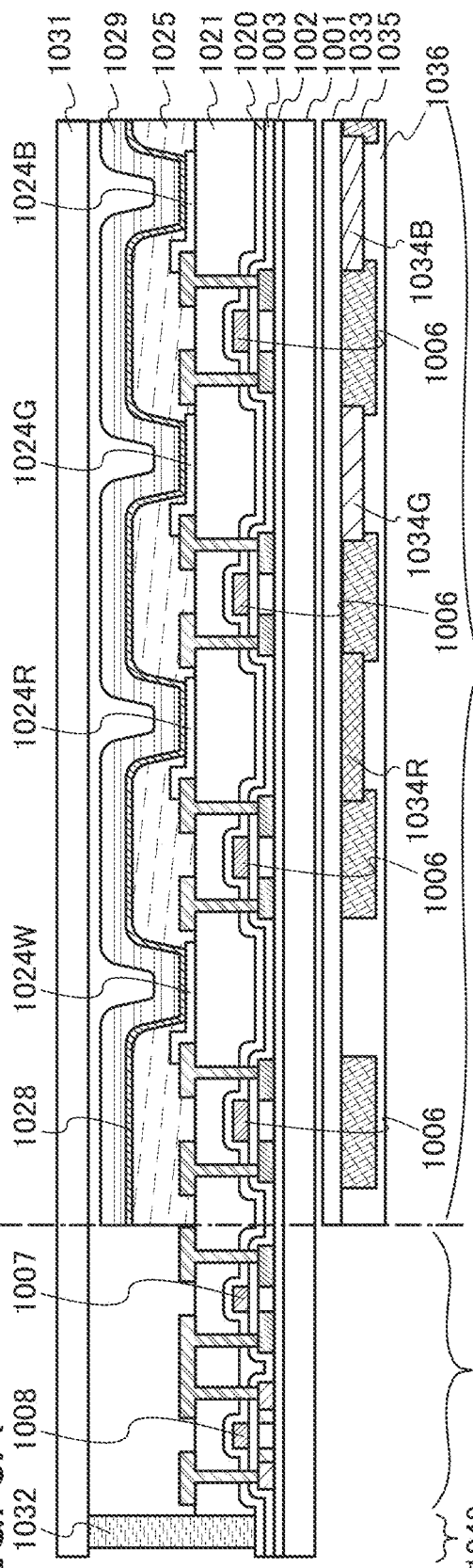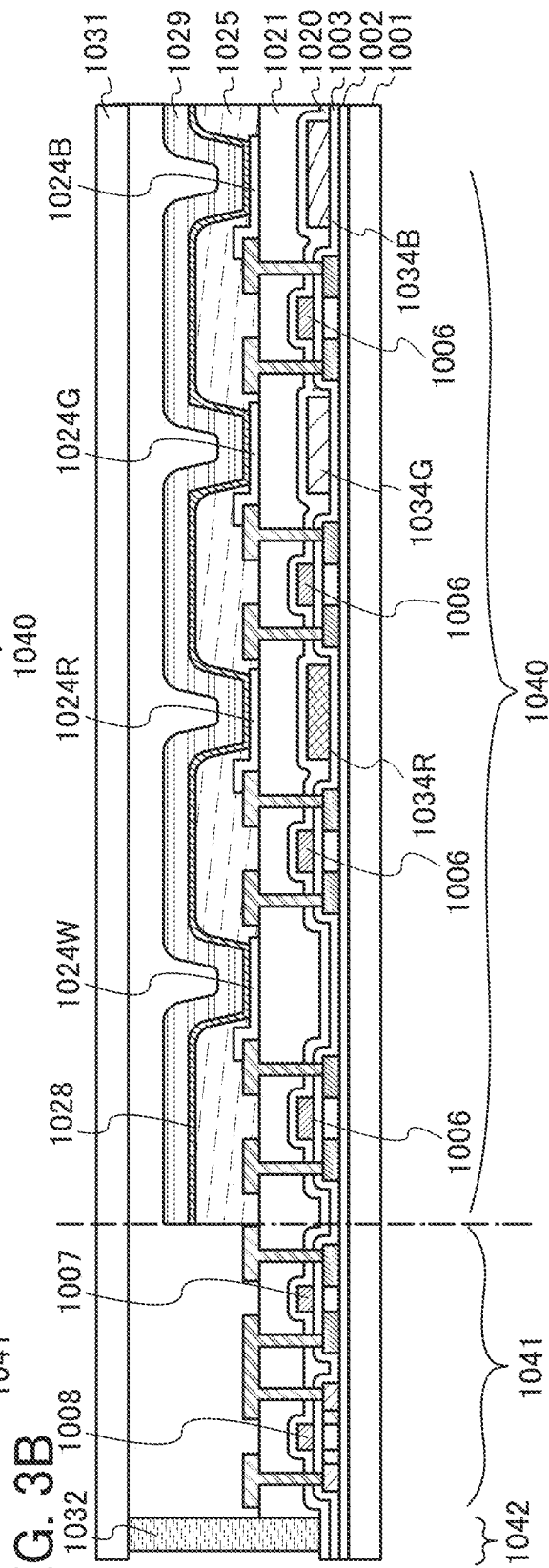

FIG. 7A
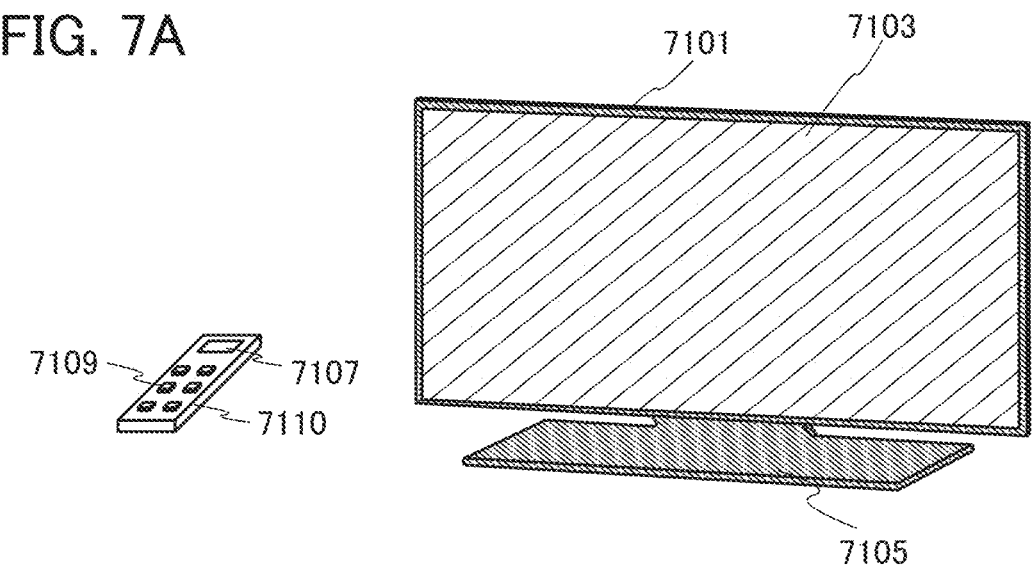
FIG. 7B1
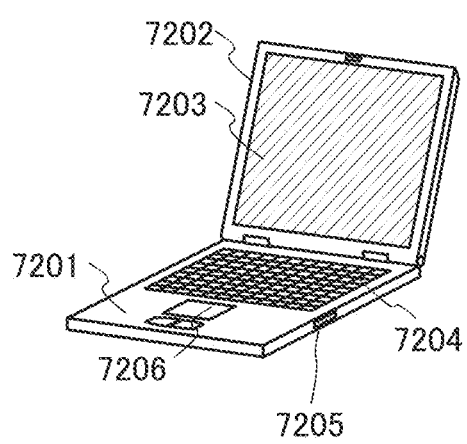
FIG. 7B2
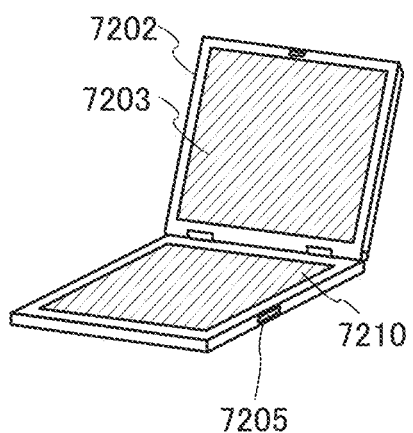
FIG. 7C
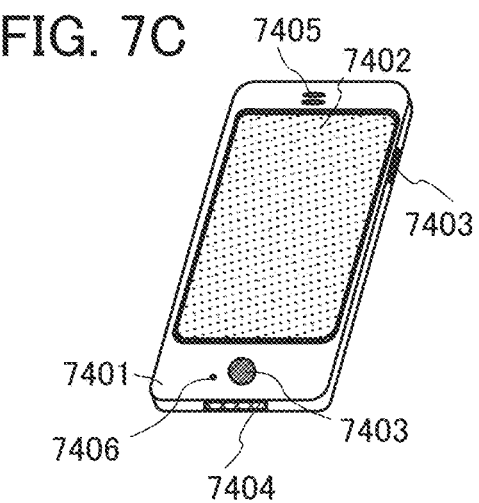

ORGANIC COMPOUND, LIGHT-EMITTING DEVICE, OPTICAL DEVICE, LIGHT-EMITTING APPARATUS, ELECTRONIC DEVICE, AND LIGHTING DEVICE

BACKGROUND OF THE INVENTION

1. Field of the Invention

One embodiment of the present invention relates to an organic compound, a light-emitting element, a light-emitting device, a display module, a lighting module, a display device, a light-emitting apparatus, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

2. Description of the Related Art

Light-emitting devices (organic EL devices) utilizing electroluminescence (EL) of organic compounds have been put to more practical use. In the basic structure of such light-emitting devices, an organic compound layer containing a light-emitting material (an EL layer) is interposed between a pair of electrodes. Carriers are injected by application of voltage to the device, and recombination energy of the carriers is used, whereby light emission can be obtained from the light-emitting material.

Such light-emitting devices are of self-luminous type and thus have advantages over liquid crystal displays, such as high visibility and no need for backlight when used as pixels of a display, and are suitable as flat panel display devices. Displays including such light-emitting devices are also highly advantageous in that they can be thin and lightweight. Moreover, such light-emitting devices also have a feature of extremely fast response speed.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the light-emitting devices also have great potential as planar light sources, which can be applied to lighting devices and the like.

Displays or lighting devices including light-emitting devices are suitable for a variety of electronic devices as described above, and research and development of light-emitting devices have progressed for more favorable characteristics (see Patent Document 1, for example).

REFERENCE

[Patent Document 1] Japanese Published Patent Application No. 2019-085387

SUMMARY OF THE INVENTION

An object of one embodiment of the present invention is to provide a novel organic compound. Another object of one embodiment of the present invention is to provide an organic compound with favorable thermophysical properties. Another object of one embodiment of the present invention is to provide an organic compound with high color purity and a low evaporation temperature.

Another object of one embodiment of the present invention is to provide a novel blue light-emitting material. Another object of one embodiment of the present invention is to provide a novel blue light-emitting material with favorable thermophysical properties. Another object of one embodiment of the present invention is to provide a blue light-emitting material with high solubility. Another object of one embodiment of the present invention is to provide a blue light-emitting material with high color purity and a low evaporation temperature.

Another object of one embodiment of the present invention is to provide an organic compound that has a low evaporation temperature and enables a light-emitting device with favorable characteristics. Another object of one embodiment of the present invention is to provide an organic compound that has a low evaporation temperature and enables a long-life light-emitting device.

Another object of one embodiment of the present invention is to provide a blue light-emitting material that has a low evaporation temperature and enables a light-emitting device with favorable characteristics. Another object of one embodiment of the present invention is to provide a blue light-emitting material that has a low evaporation temperature and enables a long-life light-emitting device. Another object of one embodiment of the present invention is to provide a blue light-emitting material that has favorable initial characteristics, a long lifetime, and a low evaporation temperature.

Another object of one embodiment of the present invention is to provide a light-emitting device, a light-emitting apparatus, an electronic device, and a display device, each of which has a long lifetime and can be fabricated easily.

Note that the descriptions of these objects do not preclude the existence of other objects. One embodiment of the present invention does not necessarily achieve all these objects. Other objects will be apparent from and can be derived from the descriptions of the specification, the drawings, the claims, and the like.

It is only necessary that at least one of the above-described objects be achieved in the present invention.

One embodiment of the present invention is an organic compound represented by General Formula (G1).

[Chemical Formula 1]

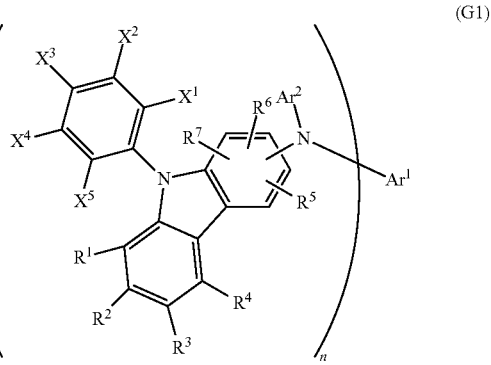

(G1)

Note that in General Formula (G1), at least one of $X^1$ to $X^5$ is a secondary or tertiary alkyl group having 3 to 6 carbon atoms in which a carbon atom bonded to a phenyl group branches, and each of the others is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms. Each of $R^1$ to $R^7$ is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms. $Ar^1$ represents a substituted or unsubstituted condensed heteroaromatic ring skeleton having 8 to 60 carbon atoms and composed of two or more aromatic rings, and $Ar^2$ represents a substituted or unsubstituted aryl group having 6 to 25 carbon atoms. Note that n is any of 1 to 3. In the case where n is 2 or 3, the two or three groups bonded to $Ar^1$ may be the same or different from each other.

Another embodiment of the present invention is the organic compound having the above structure, in which $Ar^1$ is a substituted or unsubstituted condensed heteroaromatic ring skeleton having 8 to 60 carbon atoms and composed of 3 to 9 aromatic rings.

Another embodiment of the present invention is the organic compound having the above structure, in which $Ar^1$ is a substituted or unsubstituted condensed heteroaromatic ring skeleton having 8 to 60 carbon atoms and composed of 3 to 7 aromatic rings.

Another embodiment of the present invention is the organic compound having the above structure, in which at least one of $X^1$ to $X^5$ is a secondary or tertiary alkyl group having 3 or 4 carbon atoms in which a carbon atom bonded to a phenyl group branches, and each of the others is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms.

Another embodiment of the present invention is the organic compound having the above structure, in which n is 2.

Another embodiment of the present invention is the organic compound having the above structure, in which $Ar^1$ is any of heteroaromatic ring skeletons represented by General Formulae (B1) to (B4).

[Chemical Formula 2]

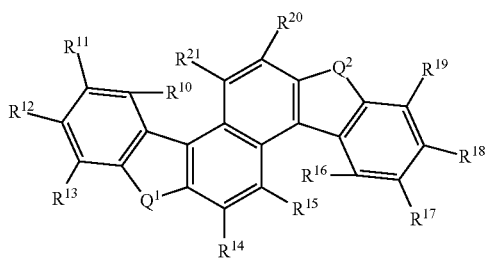

(B1)

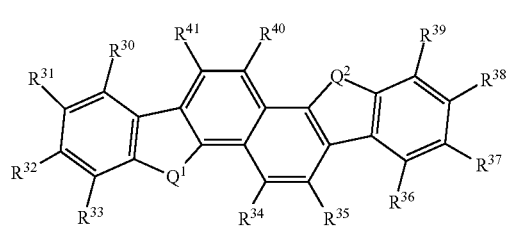

(B2)

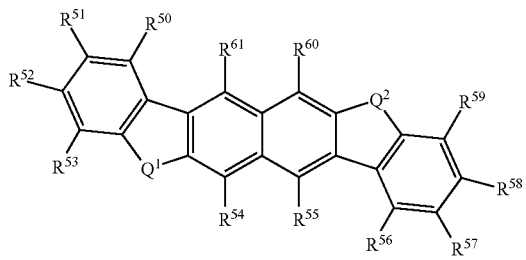

(B3)

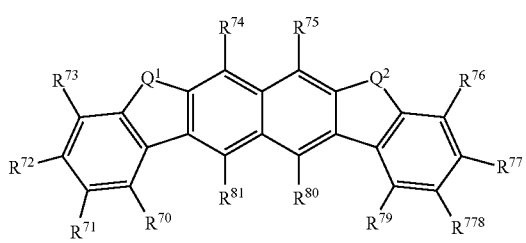

(B4)

Note that in the formulae, each of $Q^1$ and $Q^2$ independently represents an oxygen atom or a sulfur atom. In General Formula (B1), anyone or two of $R^{10}$ to $R^{21}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms. In General Formula (B2), any one or two of $R^{30}$ to $R^{41}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms. In General Formula (B3), any one or two of $R^{50}$ to $R^{61}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms. In General Formula (B4), any one or two of $R^{70}$ to $R^{81}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms.

Another embodiment of the present invention is the organic compound having the above structure, in which $Ar^1$ is a heteroaromatic ring skeleton represented by General Formula (B1-1) or (B3-1).

[Chemical Formula 3]

(B1-1)

-continued

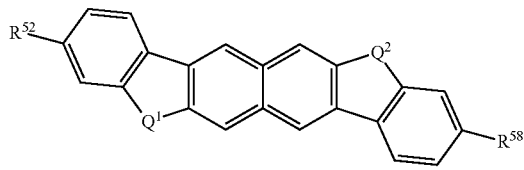
(B3-1)

Note that in the formulae, each of $Q^1$ and $Q^2$ independently represents an oxygen atom or a sulfur atom. In addition, each of $R^{12}$, $R^{18}$, $R^{52}$, and $R^{58}$ represents a single bond.

Another embodiment of the present invention is the organic compound having the above structure, which is represented by General Formula (G1-1).

[Chemical Formula 4]

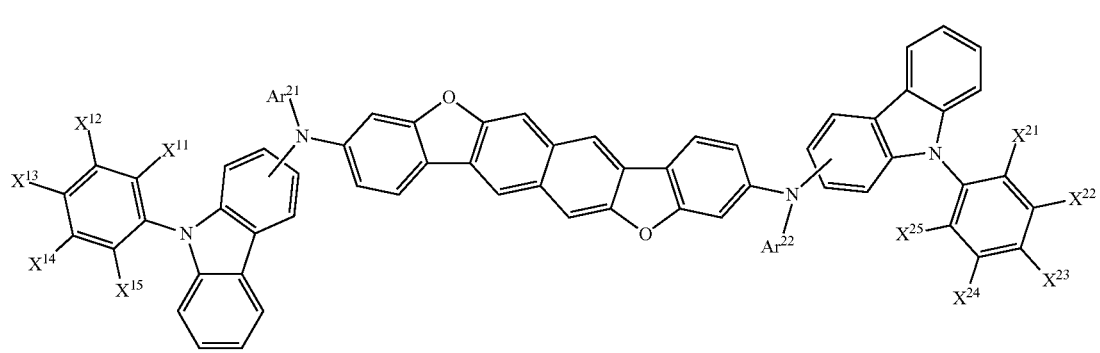
(G1-1)

Note that in General Formula (G1-1), at least one of $X^{11}$ to $X^{15}$ is a secondary or tertiary alkyl group having 3 to 6 carbon atoms in which a carbon atom bonded to a phenyl group branches, and each of the others is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms. At least one of $X^{21}$ to $X^{25}$ is a secondary or tertiary alkyl group having 3 to 6 carbon atoms in which a carbon atom bonded to a phenyl group branches, and each of the others is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms. Each of $Ar^{21}$ and $Ar^{22}$ independently represents a substituted or unsubstituted aryl group having 6 to 25 carbon atoms.

Another embodiment of the present invention is a light-emitting device including any of the above organic compounds.

Another embodiment of the present invention is an electronic device including the above light-emitting device, and at least one of a sensor, an operation button, a speaker, and a microphone.

Another embodiment of the present invention is a light-emitting apparatus including the light-emitting device, and at least one of a transistor and a substrate.

Another embodiment of the present invention is a lighting device including the above light-emitting device and a housing.

Note that the light-emitting apparatus in this specification includes, in its category, an image display device that uses a light-emitting device. The light-emitting apparatus may include a module in which a light-emitting device is provided with a connector such as an anisotropic conductive film or a tape carrier package (TCP), a module in which a printed wiring board is provided at the end of a TCP, and a module in which an integrated circuit (IC) is directly mounted on a light-emitting device by a chip on glass (COG) method. Furthermore, a lighting apparatus or the like may include the light-emitting apparatus.

According to one embodiment of the present invention, a novel organic compound can be provided. According to another embodiment of the present invention, an organic compound with favorable thermophysical properties can be provided. According to another embodiment of the present invention, an organic compound with favorable color purity and a low evaporation temperature can be provided.

According to another embodiment of the present invention, a novel blue light-emitting material can be provided.

According to another embodiment of the present invention, a blue light-emitting material with favorable thermophysical properties can be provided. According to another embodiment of the present invention, a blue light-emitting material with favorable color purity and a low evaporation temperature can be provided.

According to another embodiment of the present invention, an organic compound that has a low evaporation temperature and enables a light-emitting device with favorable characteristics can be provided. According to another embodiment of the present invention, an organic compound that has a low evaporation temperature and enables a long-life light-emitting device can be provided. According to another embodiment of the present invention, an organic compound that has favorable initial characteristics, a long lifetime, and a low evaporation temperature can be provided.

According to another embodiment of the present invention, a blue light-emitting material that has a low evaporation temperature and enables a light-emitting device with favorable characteristics can be provided. According to another embodiment of the present invention, a blue light-emitting material that has a low evaporation temperature and enables a long-life light-emitting device can be provided. According to another embodiment of the present invention, a blue light-emitting material that has favorable initial characteristics, a long lifetime, and a low evaporation temperature can be provided.

According to another embodiment of the present invention, a light-emitting device, a light-emitting apparatus, an electronic device, and a display device, each of which has a long lifetime and can be fabricated easily, can be provided.

Note that the descriptions of these effects do not preclude the existence of other effects. One embodiment of the present invention does not necessarily have all these effects. Other effects will be apparent from and can be derived from the descriptions of the specification, the drawings, the claims, and the like.

BRIEF DESCRIPTION OF THE DRAWINGS

In the accompanying drawings:

FIGS. 2A and 2B are conceptual views of an active matrix light-emitting apparatus;

FIGS. 3A and 3B are conceptual views of active matrix light-emitting apparatuses;

FIGS. 7A, 7B1, 7B2, and 7C illustrate electronic devices;

DETAILED DESCRIPTION OF THE INVENTION

Figure 1A:
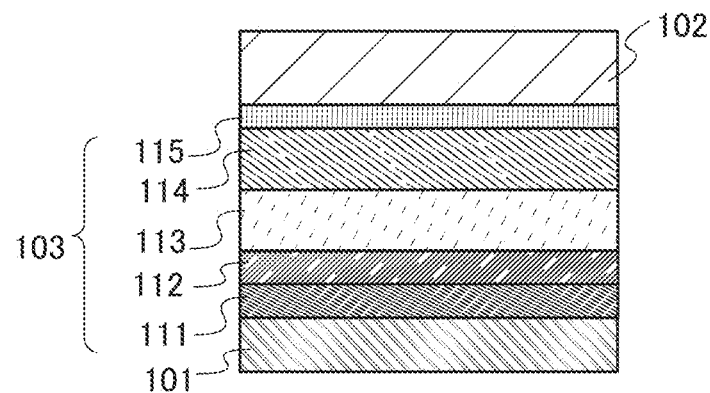
FIGS. 1A to 1C are schematic views of light-emitting devices.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Embodiment 1

In this embodiment, an organic compound of one embodiment of the present invention will be described.

The organic compound of one embodiment of the present invention is represented by General Formula (G1).

[Chemical Formula 5]

(G1)

In the organic compound represented by General Formula (G1), at least one of $X^1$ to $X^5$ is a secondary or tertiary alkyl group having 3 to 6 carbon atoms in which a carbon atom bonded to a phenyl group branches. Hereinafter, the alkyl group is referred to as a branched alkyl group in some cases. When at least one of $X^1$ to $X^5$ in the organic compound represented by General Formula (G1) is the branched alkyl group, the organic compound can have a higher sublimation property or higher solubility in a solvent, and thus can be easily formed and purified. As a result, the organic compound and a device including the organic compound can have high productivity and high reliability.

That is, in an alkyl group bonded to a phenyl group at the 9-position of a carbazolyl group, the carbon atom directly bonded to the phenyl group branches, which can inhibit intermolecular interaction and improve the sublimation property or the solubility in a solvent. In addition, since conjugation is unlikely to extend to the phenyl group at the 9-position of the carbazolyl group, the emission spectrum and the absorption spectrum are unlikely to change even when an alkyl group is introduced to the phenyl group. Furthermore, an alkyl group is preferably introduced to the 5 phenyl group, in which case heat resistance can be improved.

Note that the alkyl group having 3 to 6 carbon atoms is preferably a secondary or tertiary alkyl group having 3 or 4 carbon atoms in which a carbon atom bonded to a phenyl group branches in terms of a low-cost synthesis and a high sublimation property.

At least one of $X^1$ to $X^5$ is the branched alkyl group, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms. Note that hydrogen is preferable in terms of the synthesis cost.

One of the features of the organic compound represented by General Formula (G1) is that the branched alkyl group bonded at any of $X^1$ to $X^5$ hardly affects the HOMO level or the LUMO level. That is, the organic compound represented by General Formula (G1) including the branched alkyl group at any of $X^1$ to $X^5$ can have higher heat resistance, a higher sublimation property, and higher solubility than an organic compound not including the branched alkyl group, with little change in the HOMO level, the LUMO level, the emission spectrum, and the band gap.

Note that $X^1$ to $X^5$ are bonded to the phenyl group at the 9-position of the carbazolyl group included in arylamine in General Formula (G1). At least one of $X^1$ to $X^5$ is the branched alkyl group as described above, and when the branched alkyl group is a secondary or tertiary alkyl group in which a carbon atom bonded to the phenyl group branches, a light-emitting device including the organic compound can have higher reliability.

Specific examples of the secondary or tertiary alkyl group having 3 to 6 carbon atoms in which a carbon atom bonded to the phenyl group branches include the following groups represented by Structural Formulae (X-1) to (X-9).

[Chemical Formula 6]

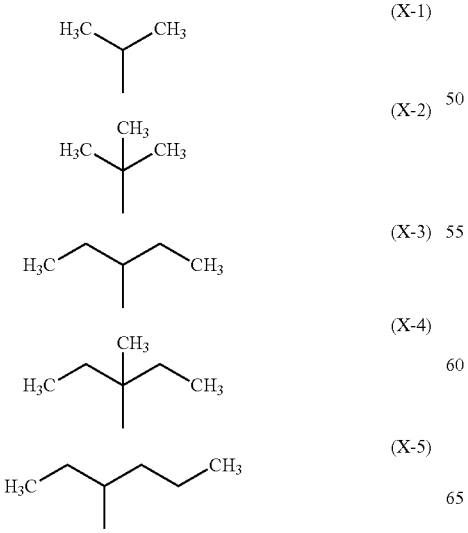

In the organic compound represented by General Formula (G1), each of $R^1$ to $R^7$ is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms.

Note that n is any of 1 to 3. In the case where n is 2 or 3, the two or three groups bonded to $Ar^1$ may be the same or different from each other. That is, in the case where n is 2 or 3, $Ar^1$ may be bonded to a plurality of same substituents or a plurality of substituents having different structures.

$Ar^1$ represents a substituted or unsubstituted condensed heteroaromatic ring skeleton having 8 to 60 carbon atoms and composed of two or more aromatic rings, and $Ar^2$ represents a substituted or unsubstituted aryl group having 6 to 25 carbon atoms.

Specific examples of the substituted or unsubstituted condensed heteroaromatic ring skeleton having 8 to 60 carbon atoms and composed of two or more aromatic rings, which is given as an example of the group represented by $Ar^1$, are Structural Formulae ($Ar^1$-1) to ($Ar^1$-39).

[Chemical Formula 7]

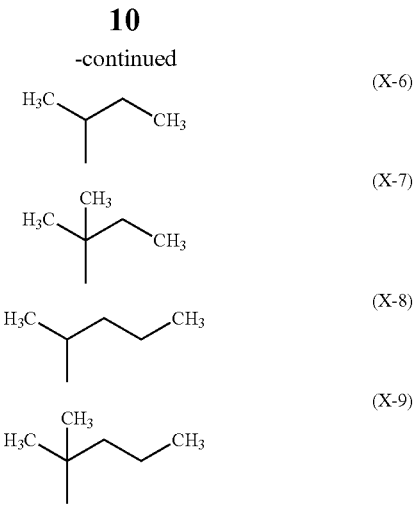
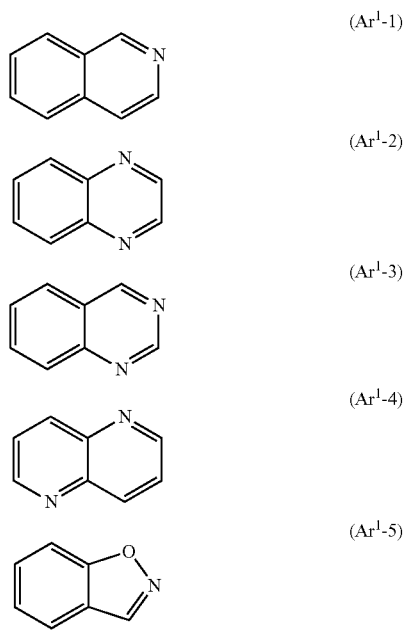

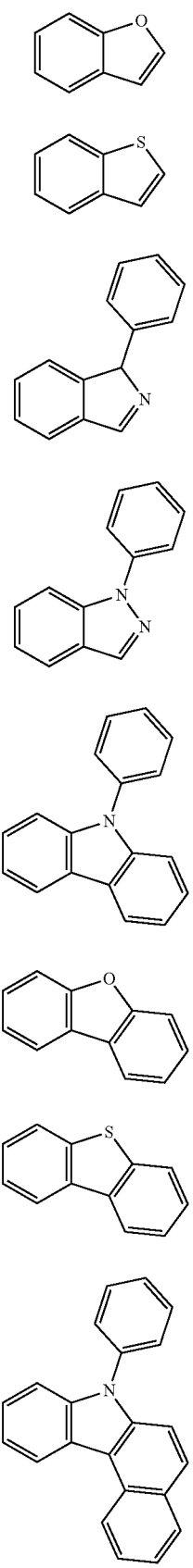
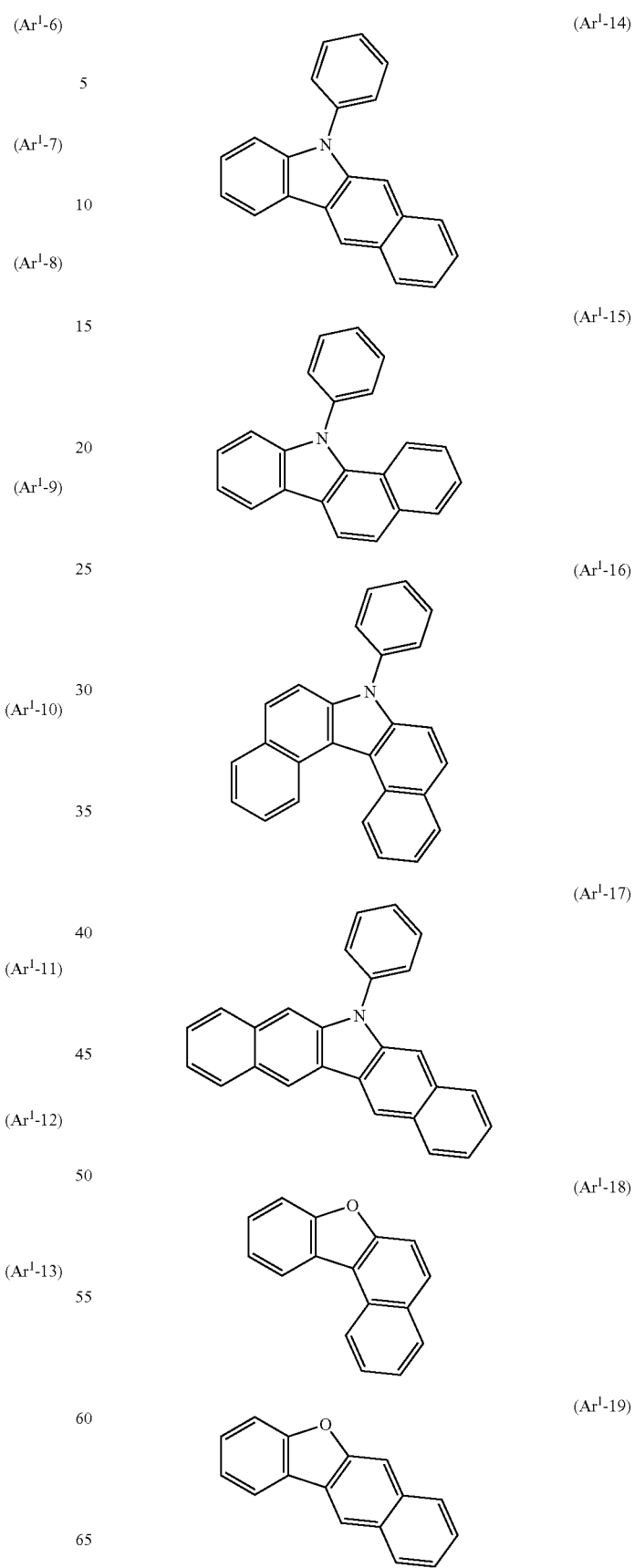

-continued (Ar¹-20)

(Ar¹-21)

(Ar¹-22)

(Ar¹-23)

(Ar¹-24)

(Ar¹-25)

(Ar¹-26)

(Ar¹-27)

(Ar¹-28)

(Ar¹-29)

(Ar¹-30)

(Ar¹-31)

(Ar¹-32)

(Ar¹-33)

(Ar¹-34)
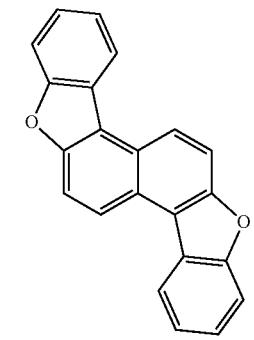

(Ar¹-35)
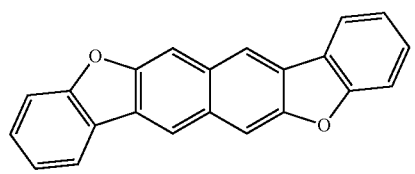

(Ar¹-36)
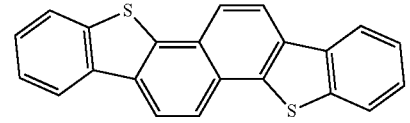

(Ar¹-37)
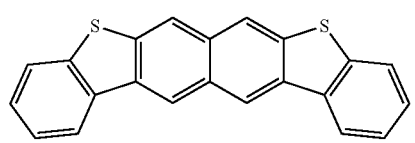

(Ar¹-38)
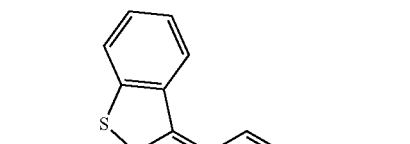

(Ar¹-39)
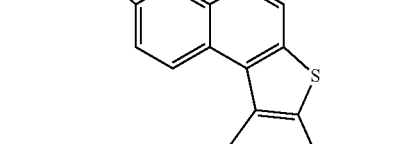

Examples of the substituted or unsubstituted aryl group having 6 to 25 carbon atoms, which is given as an example of the group represented by Ar², include a phenyl group, a thryl group, a dimethylphenyl group, a trimethylphenyl group, a propylphenyl group, a dipropylphenyl group, a butylphenyl group, a dibutylphenyl group, a cyclohexylphenyl group, a naphthyl group, a naphthylphenyl group, a phenylnaphthyl group, a biphenyl group, a terphenyl group, a fluorenyl group, a 9,9-dimethylfluorenyl group, a phenanthryl group, a 9,9-diphenylfluorenyl group, a spirofluorenyl group, a triphenylenyl group, a pyrenyl group, an anthryl group, and a 9-phenylanthryl group. Specific examples are Structural Formulae (Ar²-1) to (Ar²-49).

[Chemical Formula 8]

(Ar²-1)
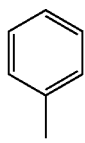

(Ar²-2)
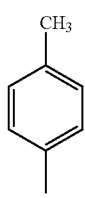

(Ar²-3)
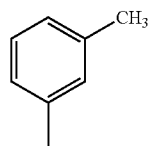

(Ar²-4)
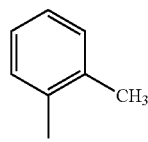

(Ar²-5)
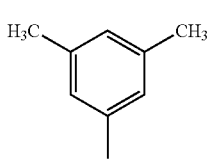

(Ar²-6)
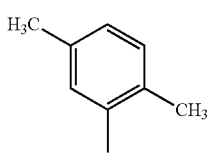

(Ar²-7)
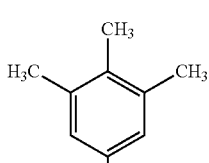

(Ar²-8)
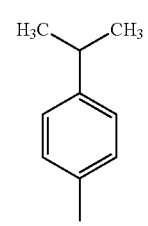

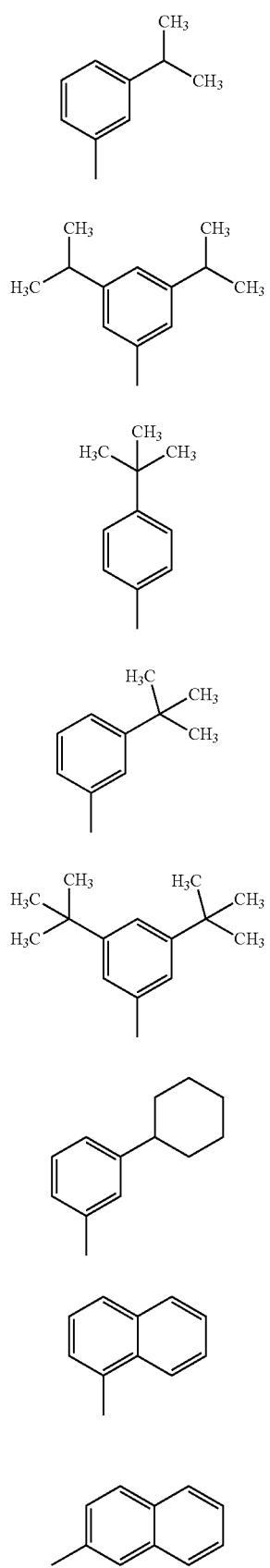
(Ar²-9)
(Ar²-10)
(Ar²-11)
(Ar²-12)
(Ar²-13)
(Ar²-14)
(Ar²-15)
(Ar²-16)
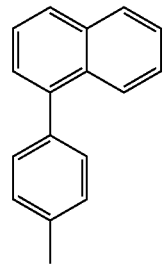
(Ar²-17)
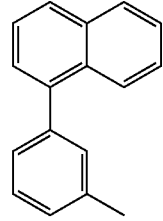
(Ar²-18)
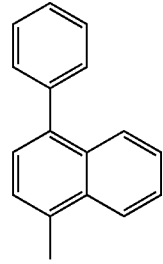
(Ar²-19)
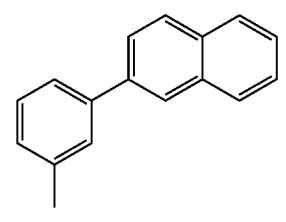
(Ar²-20)
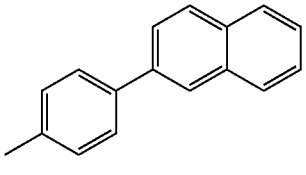
(Ar²-21)
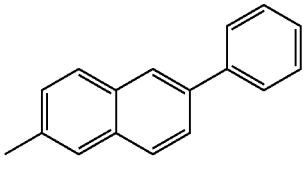
(Ar²-22)
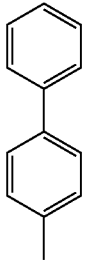
(Ar²-23)

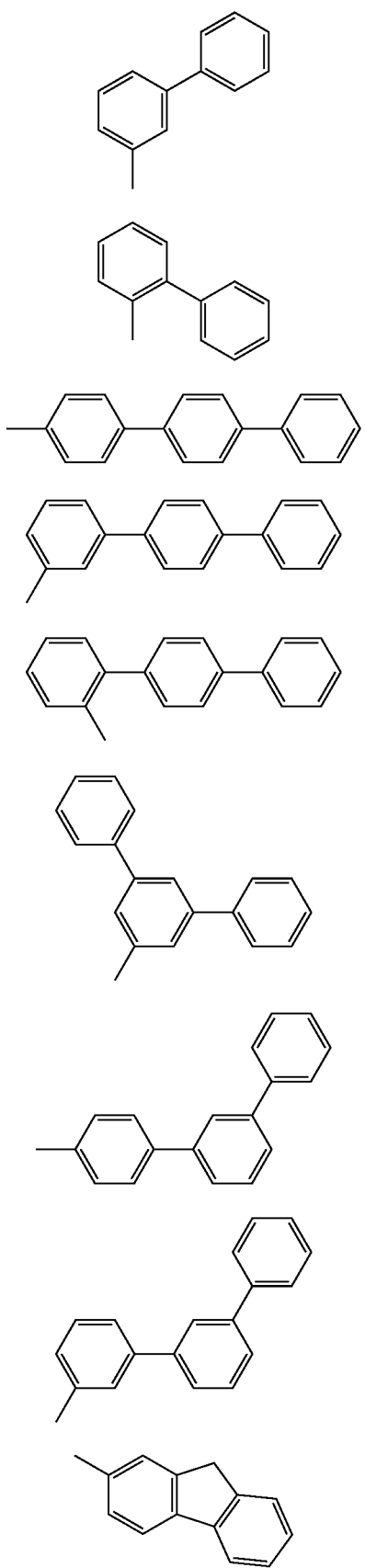
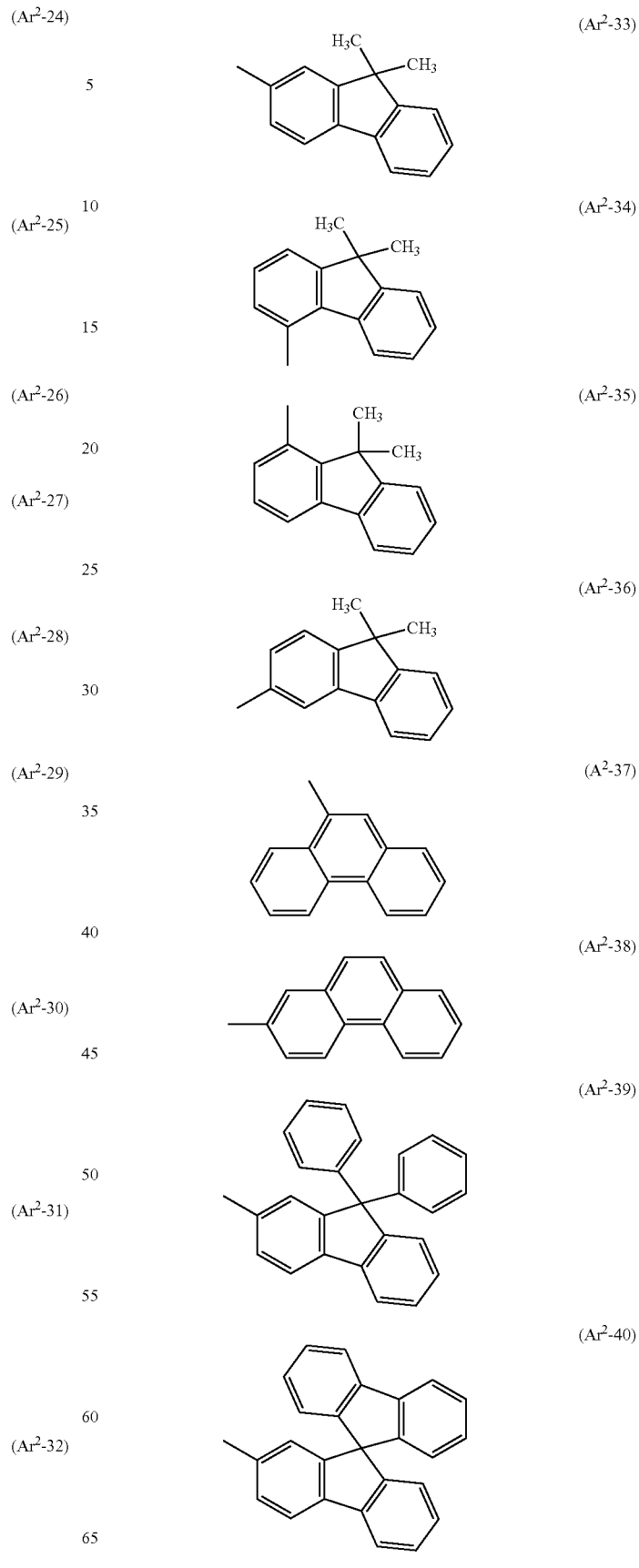

-continued

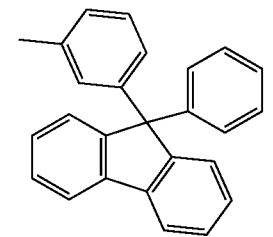
(Ar²-41)

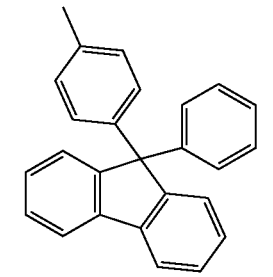
(Ar²-42)

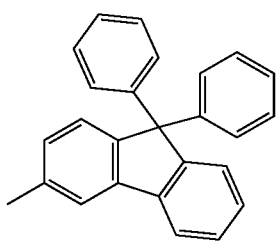
(Ar²-43)

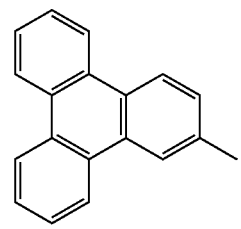
(Ar²-44)

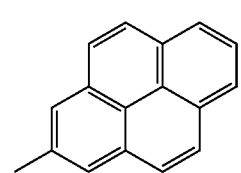
(Ar²-45)

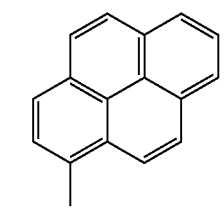
(Ar²-46)

-continued

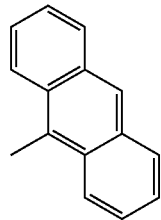
(Ar²-47)

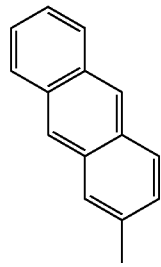
(Ar²-48)

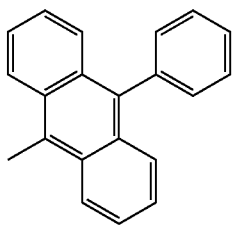
(Ar²-49)

Note that $Ar^1$ is preferably a substituted or unsubstituted condensed heteroaromatic ring skeleton having 8 to 60 carbon atoms and composed of 3 to 9 aromatic rings because of its high sublimation property, and further preferably a substituted or unsubstituted condensed heteroaromatic ring skeleton having 8 to 60 carbon atoms and composed of 3 to 7 aromatic rings because of its high heat resistance.

In particular, an organic compound in which $Ar^1$ is any of heteroaromatic ring skeletons represented by General Formulae (B31) to (B34) is further preferable because it exhibits favorable blue light emission.

[Chemical Formula 10]

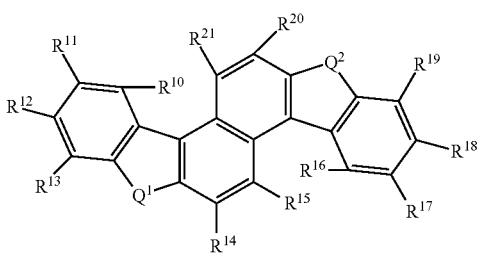
(B1)

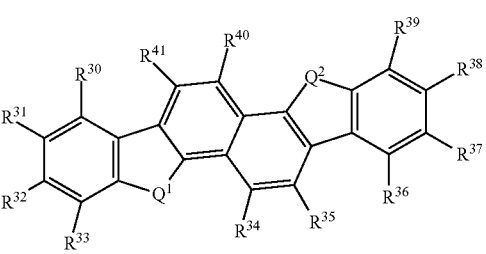
(B2)

(B3)

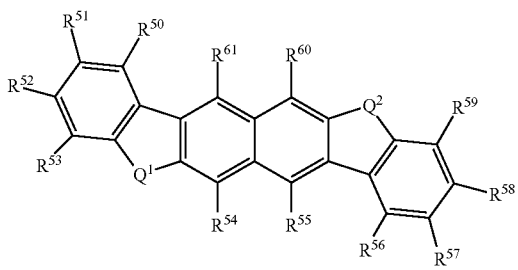

(B4)

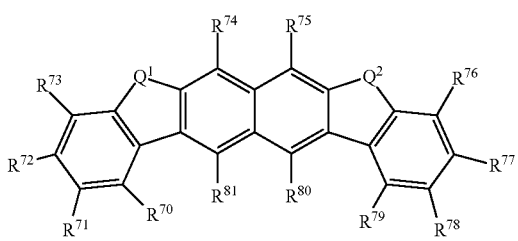

In General Formulae (B1) to (B4), each of $Q^1$ and $Q^2$ independently represents an oxygen atom or a sulfur atom. In General Formula (B1), anyone or two of $R^{10}$ to $R^{21}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms. In General Formula (B2), any one or two of $R^{30}$ to $R^{41}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms. In General Formula (B3), any one or two of $R^{50}$ to $R^{61}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms. In General Formula (B4), any one or two of $R^{70}$ to $R^{81}$ represent a single bond, and each of the others independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms.

Note that among General Formulae (B1) to (B4), the heteroaromatic ring skeleton represented by General Formula (B1) or (B3) is preferable because it exhibits blue emission, and a heteroaromatic ring skeleton represented by General Formula (B1-1) or (B3-1) is further preferable because it can improve the luminescence quantum yield. Note that in General Formulae (B1-1) and (B3-1), each of $Q^1$ and $Q^2$ independently represents an oxygen atom or a sulfur atom. Furthermore, each of $R^{12}$, $R^{18}$, $R^{52}$, and $R^{58}$ represents a single bond.

[Chemical Formula 11]

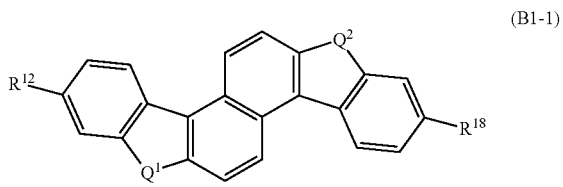

(B1-1)

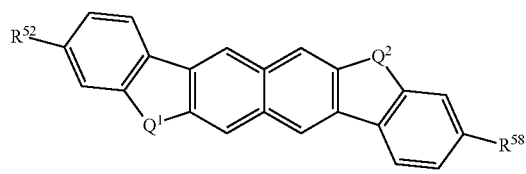

(B3-1)

In the organic compound represented by General Formula (G1), $Ar^1$ is preferably the heteroaromatic ring skeleton represented by General Formula (B3-1), in which case the organic compound can have high color purity and favorable blue light emission, and $R^1$ to $R^7$ are each preferably hydrogen for easy synthesis. That is, the organic compound of one embodiment of the present invention is preferably an organic compound represented by General Formula (G1-1).

[Chemical Formula 12]

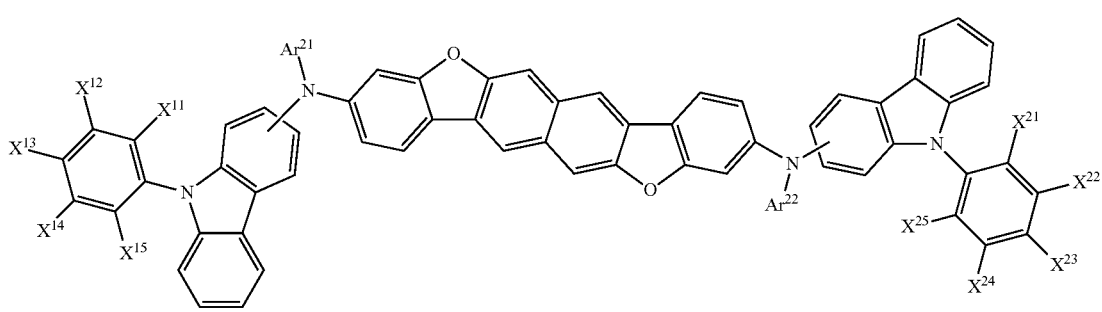

(G1-1)

In General Formula (G1-1), at least one of $X^{11}$ to $X^{15}$ is a secondary or tertiary alkyl group having 3 to 6 carbon atoms in which a carbon atom bonded to a phenyl group branches, and each of the others is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms. Furthermore, at least one of $X^{21}$ to $X^{25}$ is a secondary or tertiary alkyl group having 3 to 6 carbon atoms in which a carbon atom bonded to a phenyl group branches, and each of the others is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms. In addition, each of $Ar^{21}$ and $Ar^{22}$ independently represents a substituted or unsubstituted aryl group having 6 to 25 carbon atoms.

The organic compound represented by General Formula (GT-1) exhibits favorable blue light emission. Furthermore, when at least one of $X^{11}$ to $X^{15}$ and at least one of $X^{21}$ to $X^{25}$ are each a secondary or tertiary alkyl group having 3 to 6 carbon atoms in which a carbon atom bonded to a phenyl group branches, the sublimation property is improved.

When $X^{11}$ to $X^{15}$ and $X^{21}$ to $X^{25}$ are all hydrogen in the organic compound represented by General Formula (G1-1), the organic compound has a relatively high molecular weight and includes a plurality of amine skeletons and furan rings in the molecule; thus, the temperature for purification by sublimation is as high as around 400° C. When heated at around 400° C., the organic compound might be burnt before sublimated. In contrast, in the organic compound of one embodiment of the present invention, at least one of $X^{11}$ to $X^{15}$ and at least one of $X^{21}$ to $X^{25}$ are each a secondary or tertiary alkyl group having 3 to 6 carbon atoms in which a carbon atom bonded to a phenyl group branches; thus, intermolecular interaction can be reduced despite of a high molecular weight, leading to a lower sublimation temperature. Accordingly, the occurrence of burning in purification by sublimation can be reduced. In addition, the evaporation temperature is also reduced and thus the productivity is improved. Furthermore, the reliability of a light-emitting device using the organic compound is improved.

Note that in the above description, when the substituted or unsubstituted group or ring includes a substituent, the substituent can be selected from the following groups: an alkyl group having 1 to 6 carbon atoms; a cycloalkyl group having 3 to 12 carbon atoms; and an unsubstituted or alkyl-substituted aryl group having 6 to 13 carbon atoms. Note that the substituent is preferably an alkyl group having 1 to 6 carbon atoms or a cycloalkyl group having 3 to 12 carbon atoms, further preferably an alkyl group having 1 to 6 carbon atoms. Furthermore, an unsubstituted group or ring is preferable in terms of easy synthesis and easy availability of the raw materials.

Examples of the above-described alkyl group having 1 to 6 carbon atoms include a methyl group, an ethyl group, a propyl group, an isopropyl group, a butyl group, a tert-butyl group, a pentyl group, and a hexyl group. The cycloalkyl group having 3 to 12 carbon atoms is preferably a cyclopropyl group, a cyclohexyl group, a norbornyl group, a decahydronaphthyl group, an adamantyl group, or the like. The aryl group having 6 to 13 carbon atoms is preferably a phenyl group, a biphenyl group, a naphthyl group, a fluorenyl group, or the like.

Specific examples of the organic compound having the above structure are shown below.

[Chemical Formula 13]

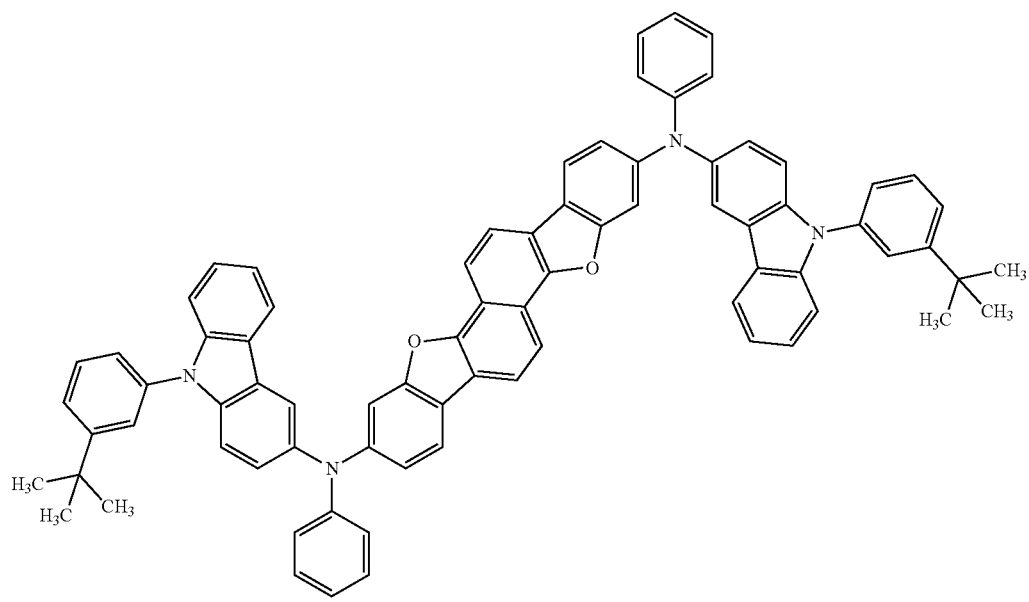

(100)

(101)
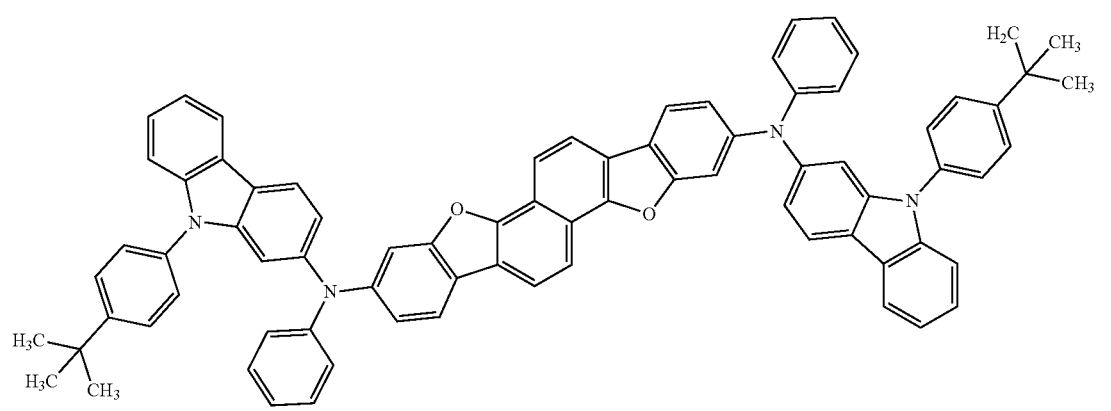
(102)
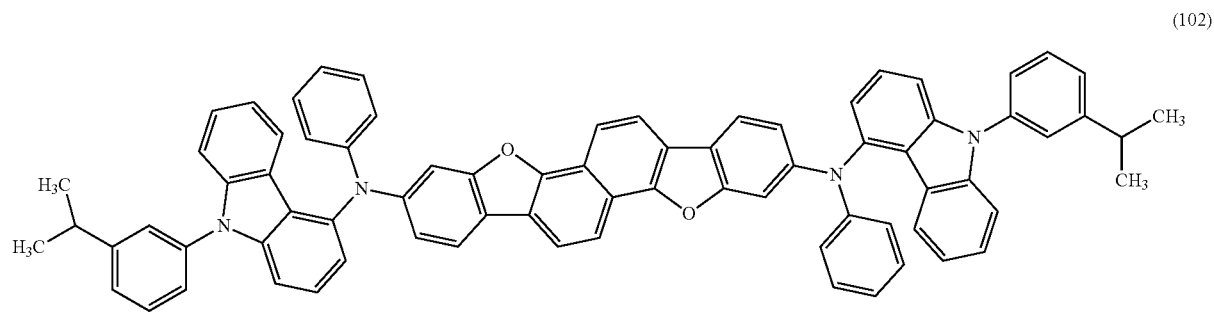
(103)
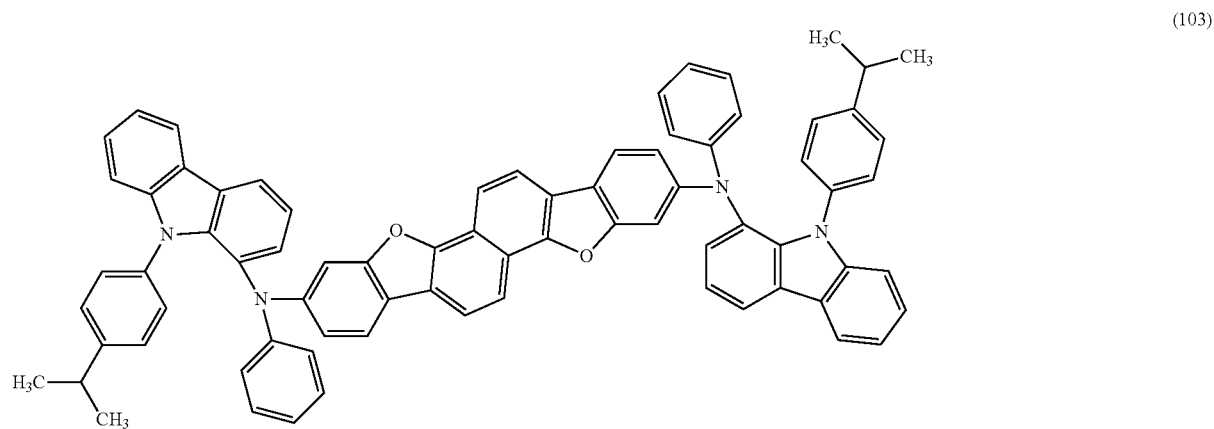
(104)
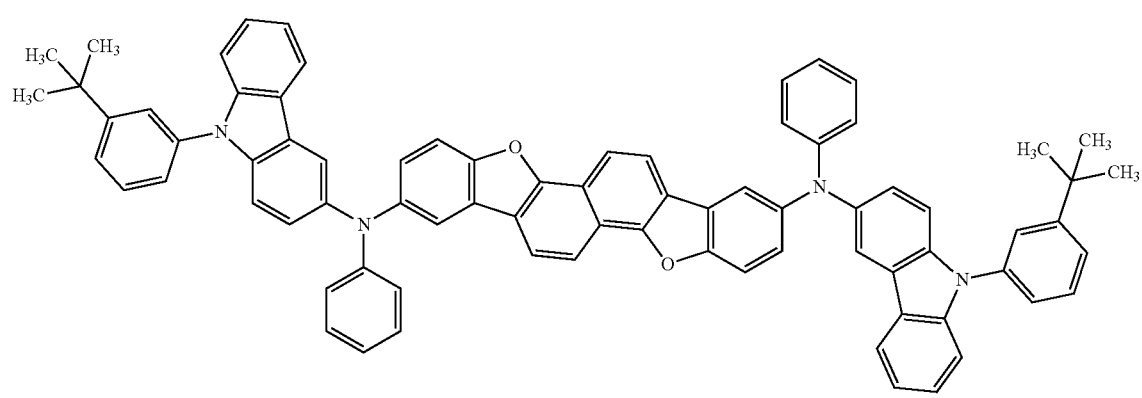

(105)
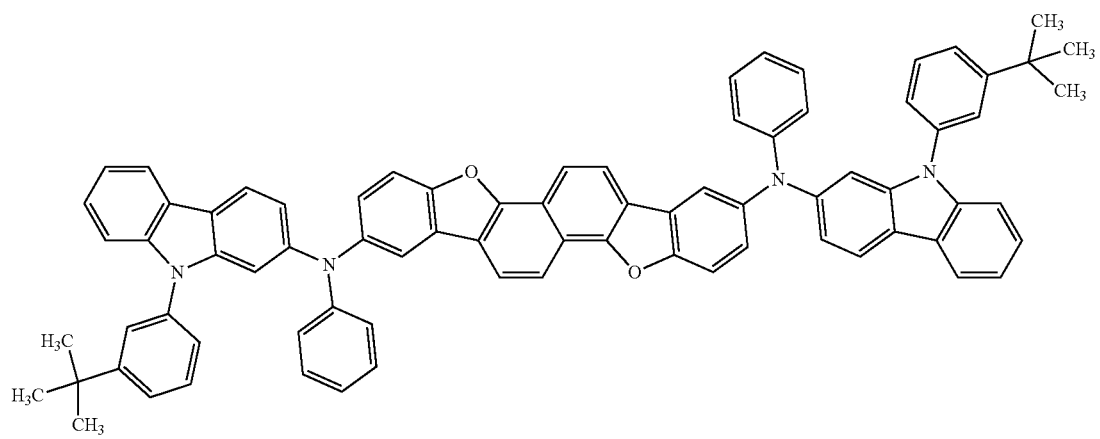
[Chemical Formula 14]
(106)
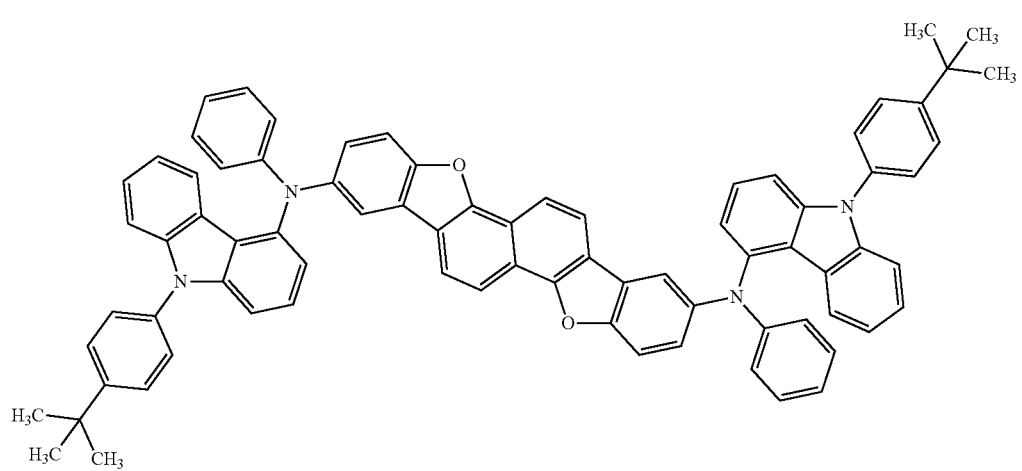
(107)
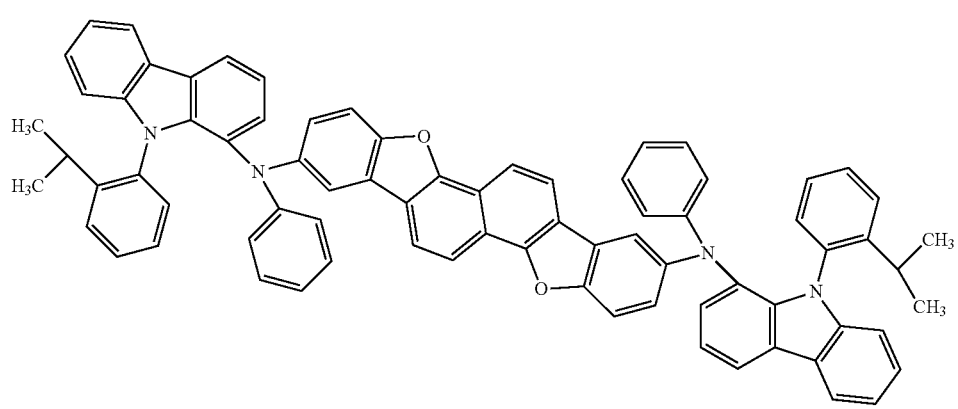

(108)
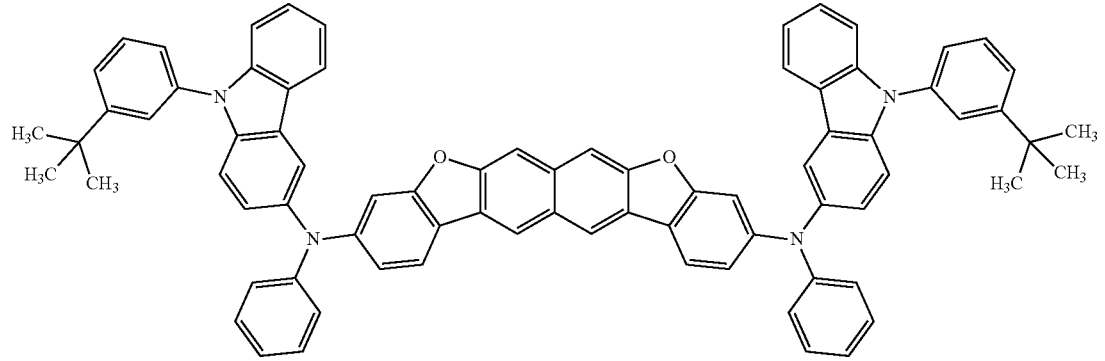
(109)
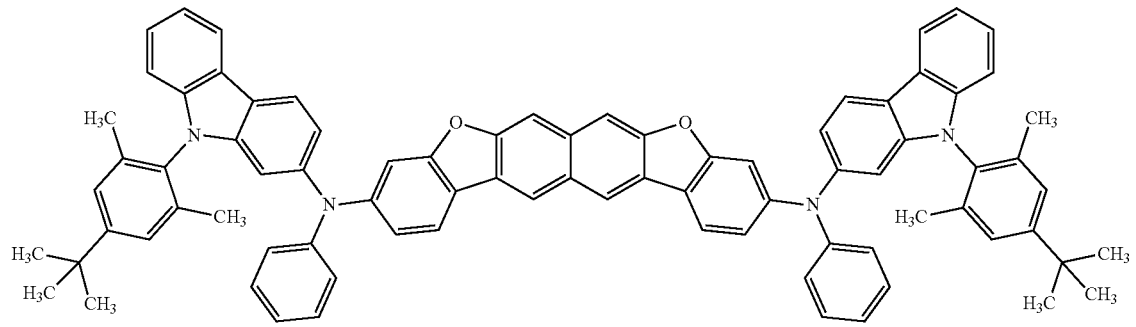
(110)
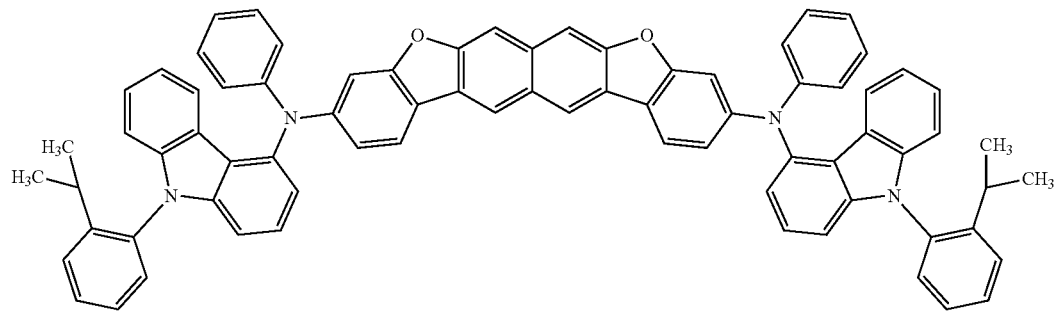
(111)
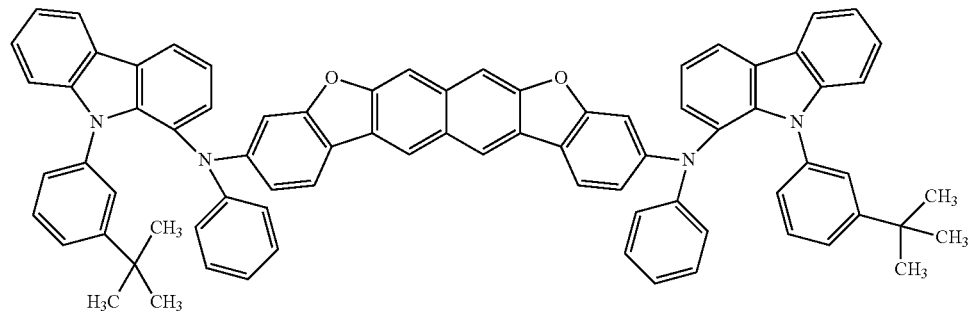

[Chemical Formula 15]
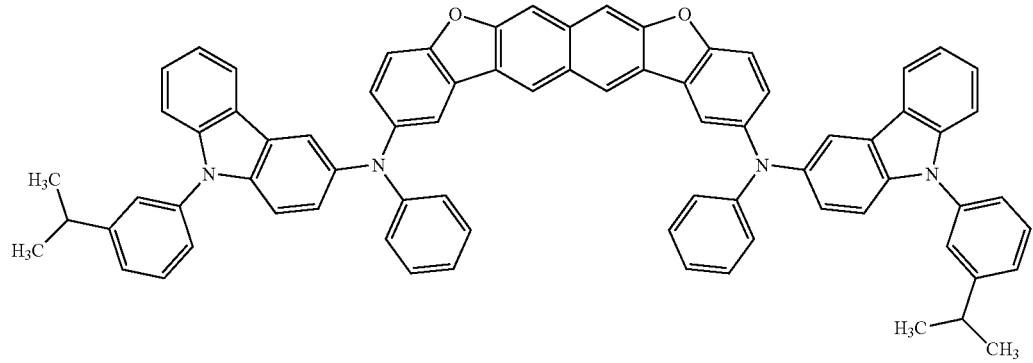
(112)
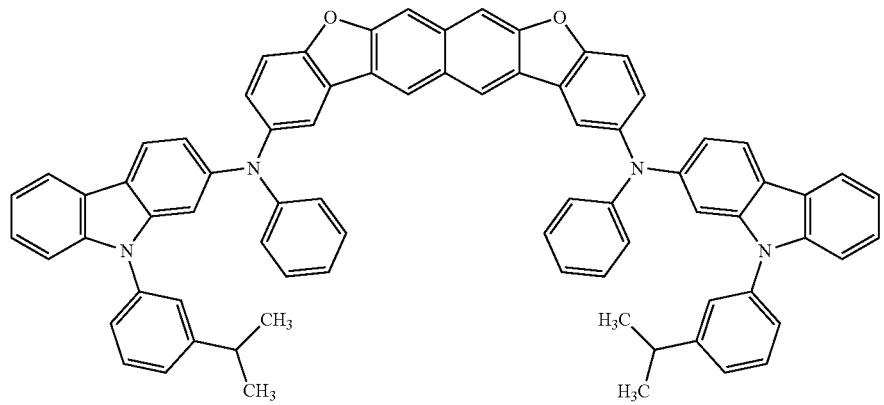
(113)
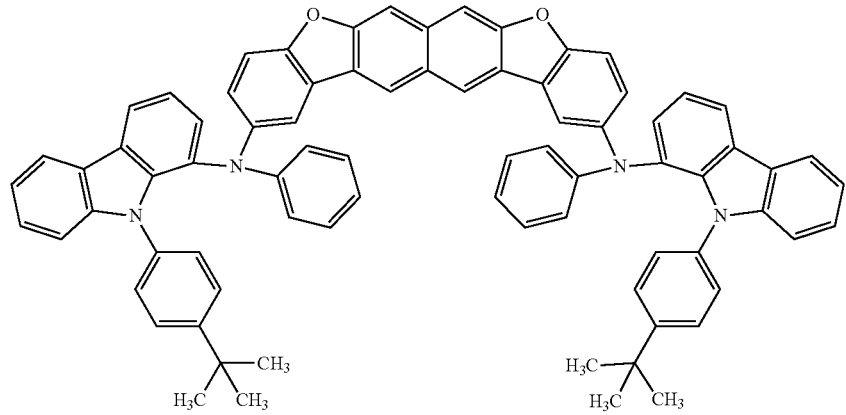
(114)
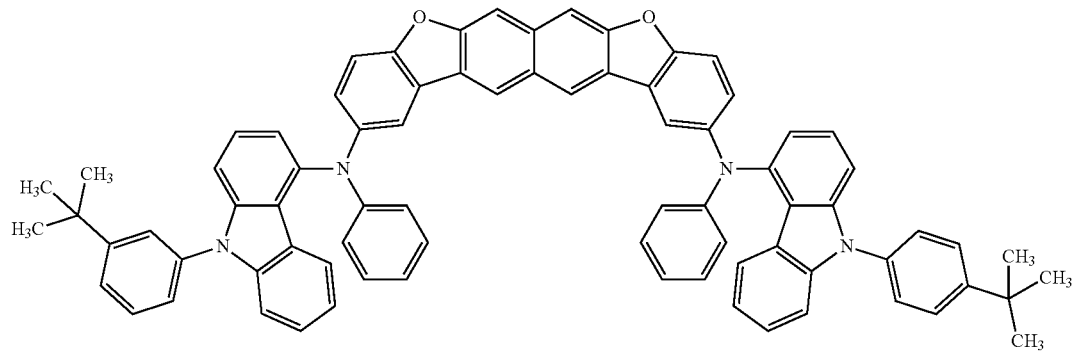
(115)

(116)
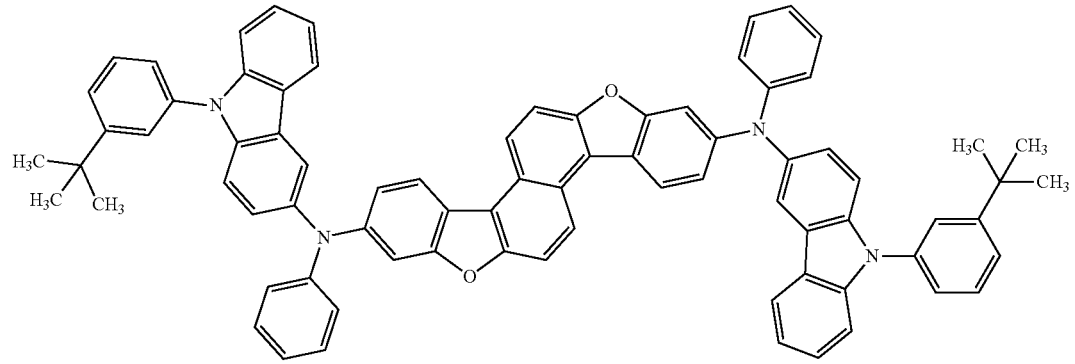
(117)
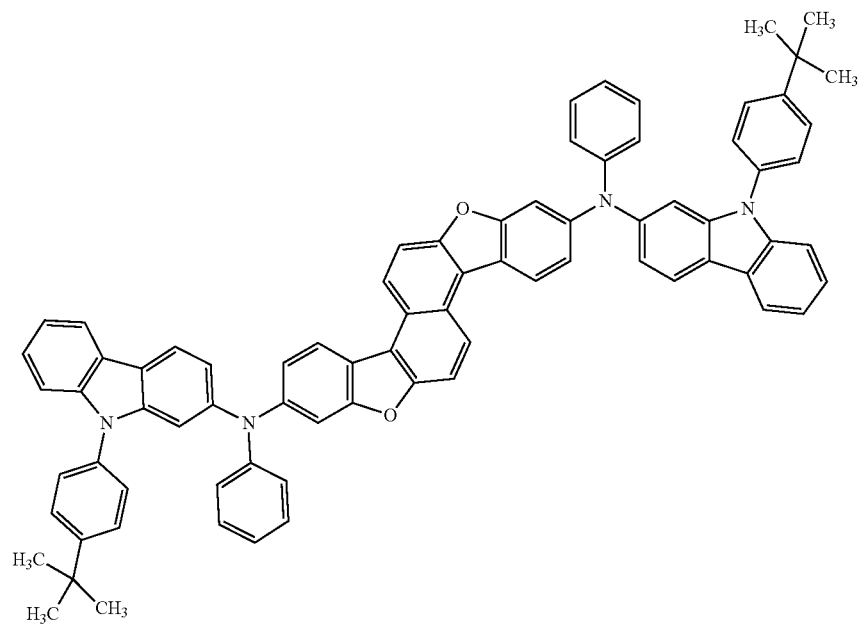
[Chemical Formula 16]
(118)
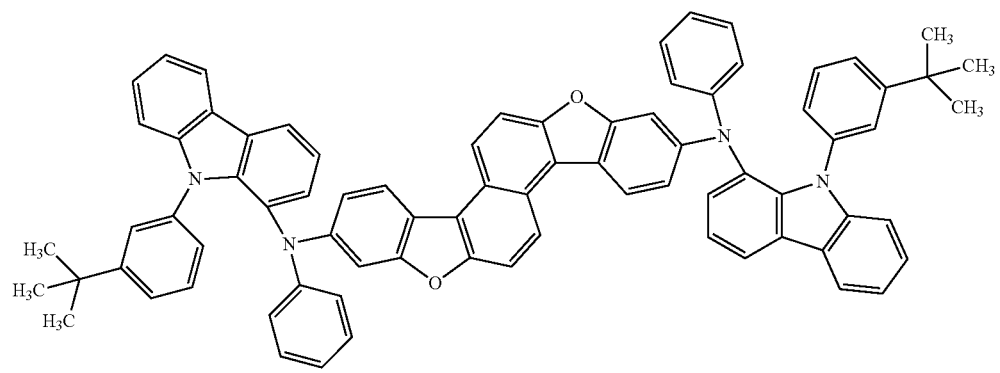

(119)
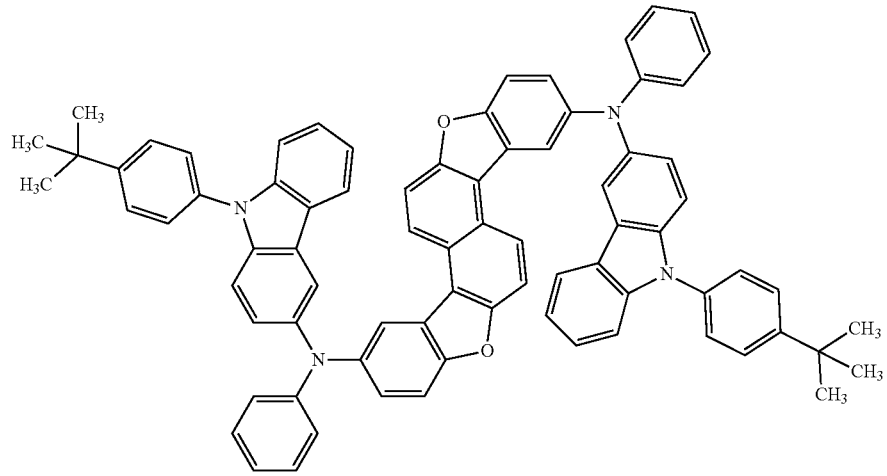
(120)
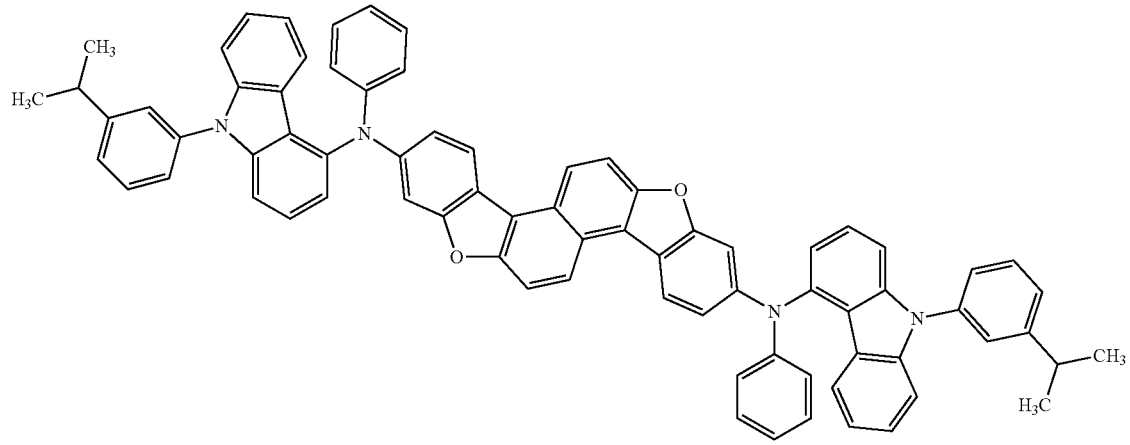
(121)
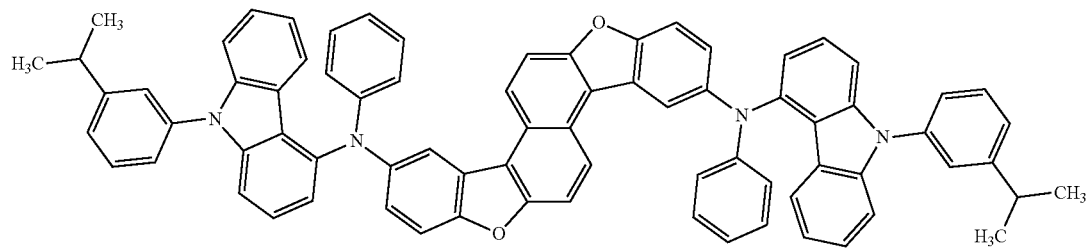
(122)
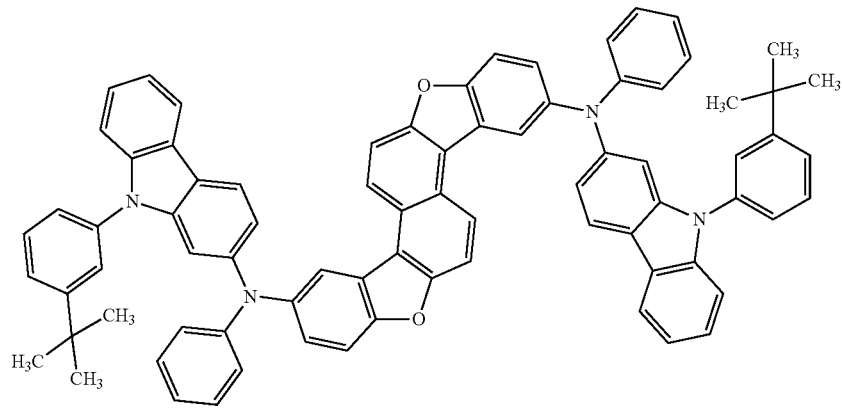

-continued
(123)
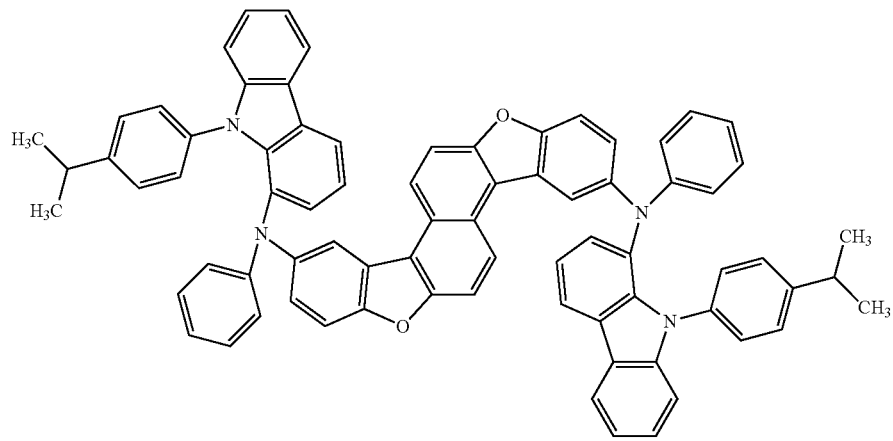
[Chemical Formula 17]
(124)
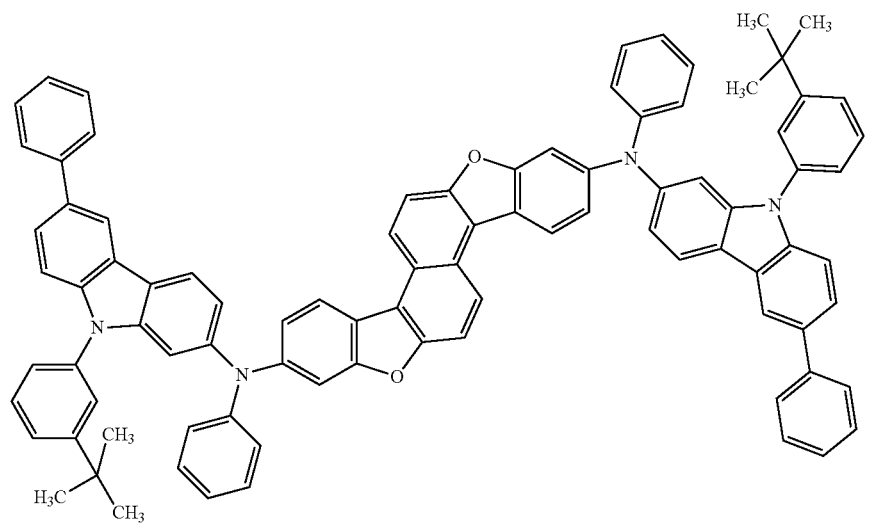
(125)
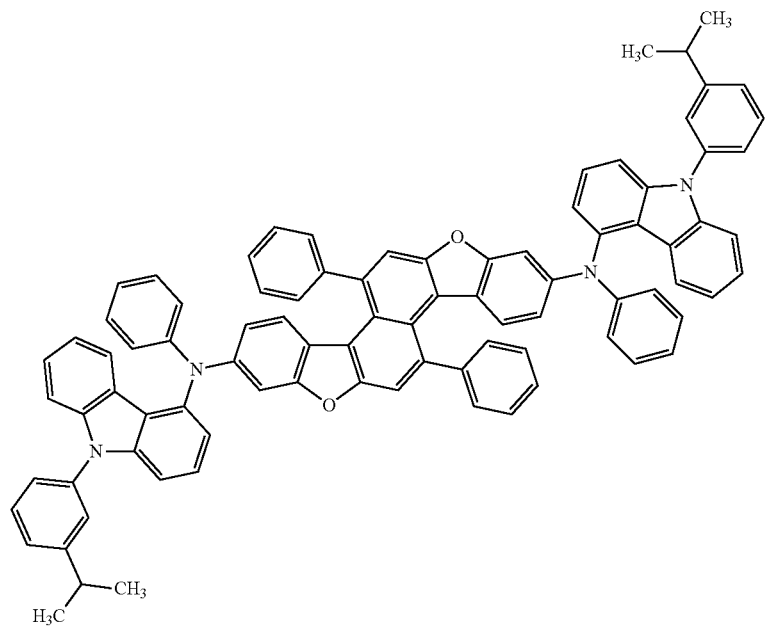

(126)
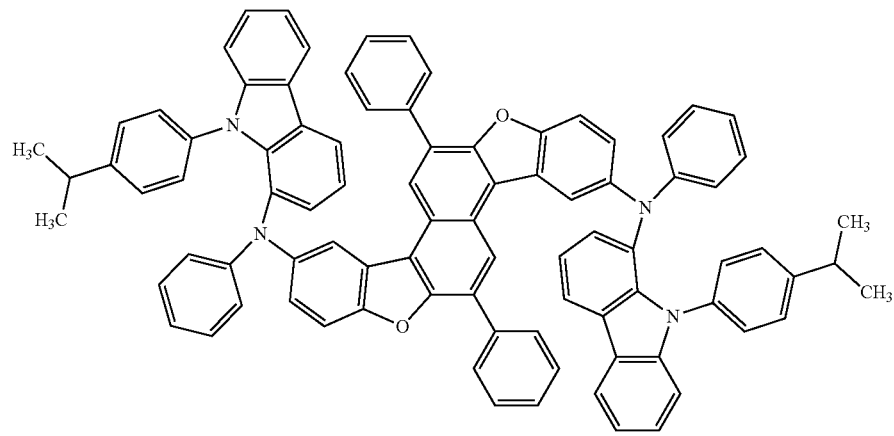
(127)
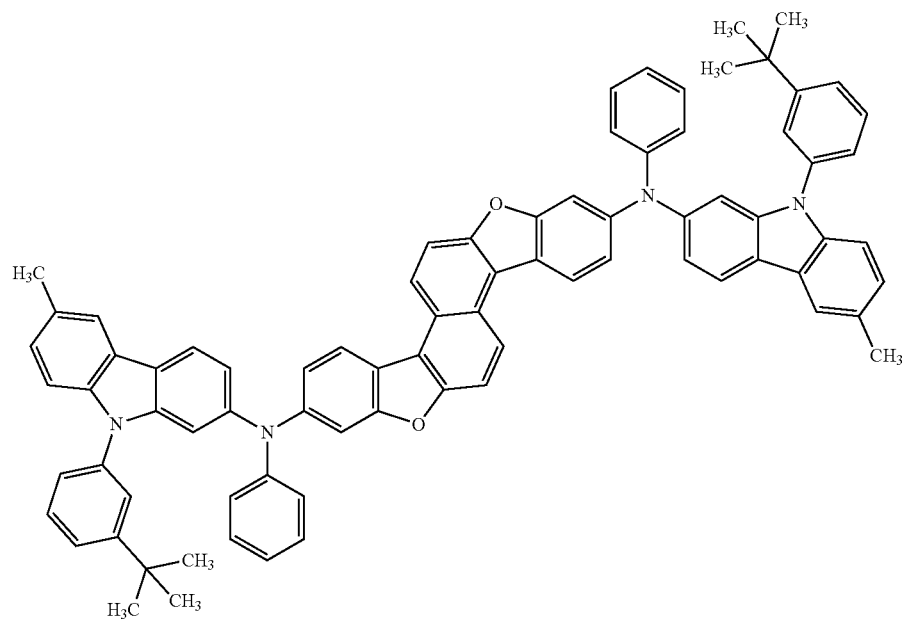
(128)
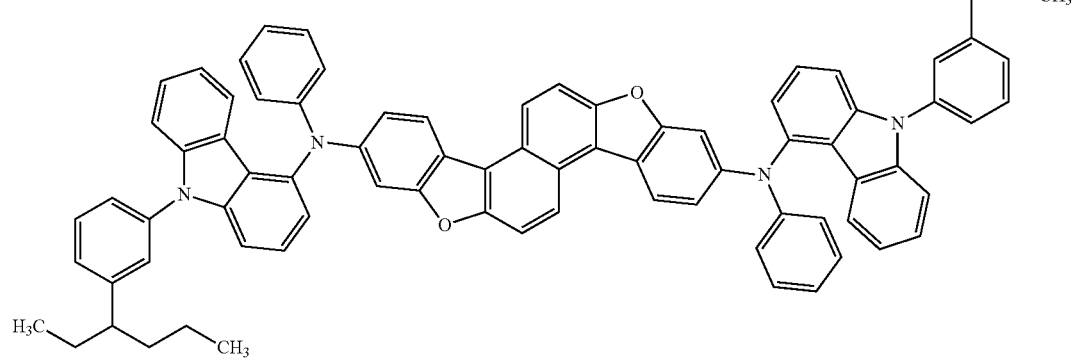

(129)
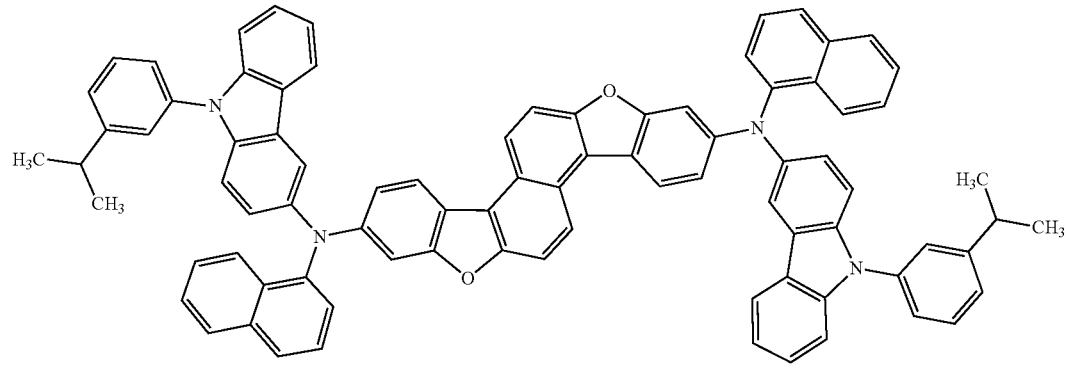
[Chemical Formula 18]
(130)
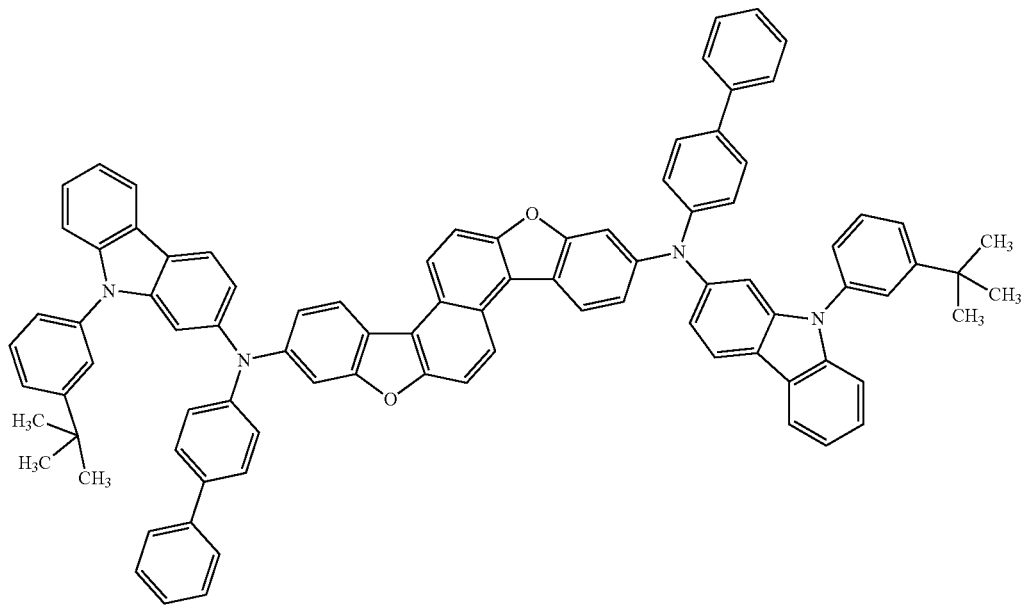
(131)
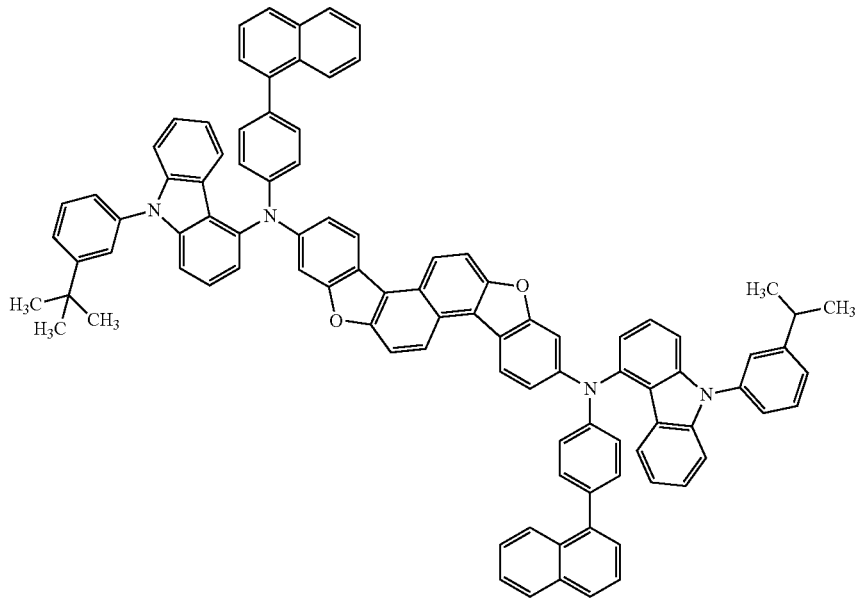

(132)
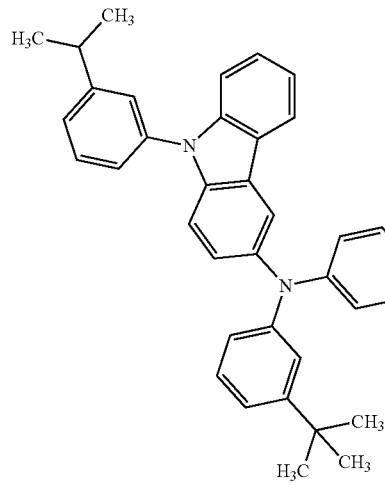
(133)
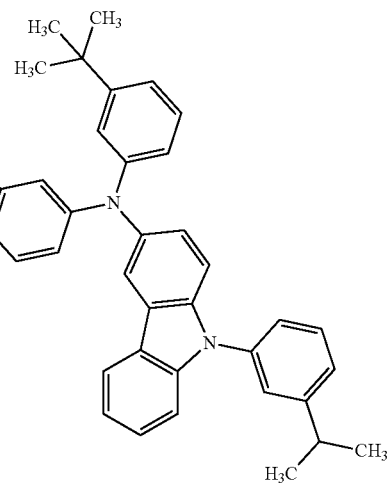
[Chemical Formula 19]
(134)
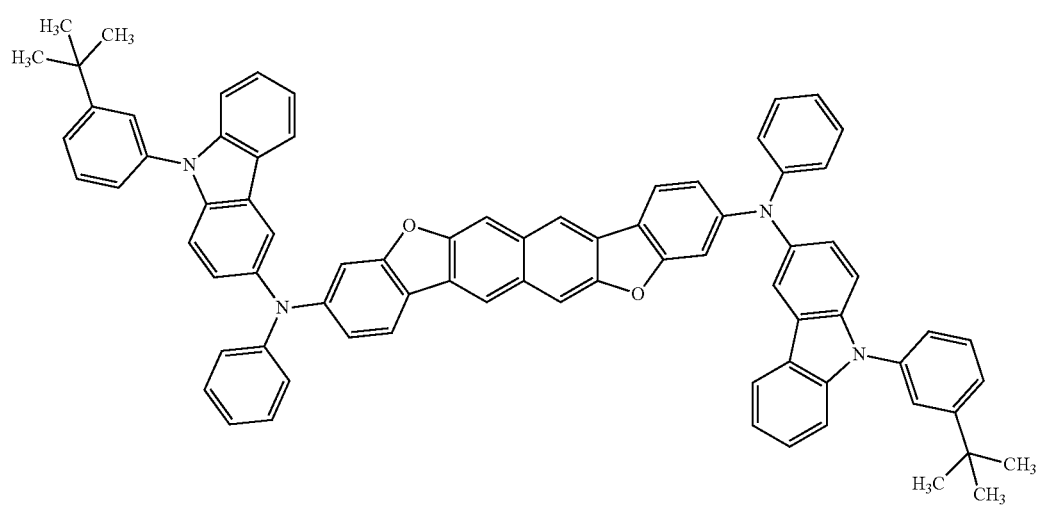

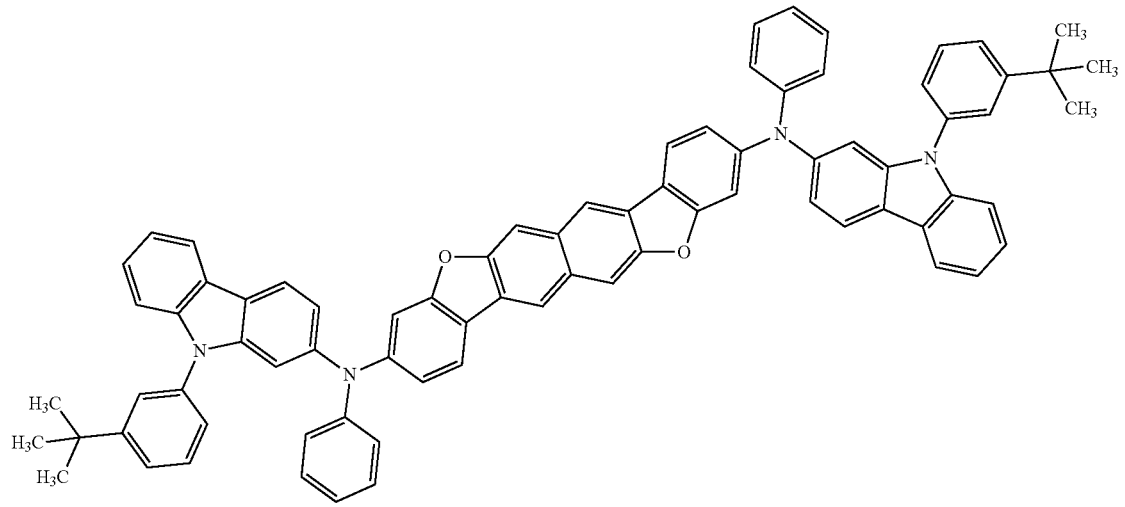
(135)
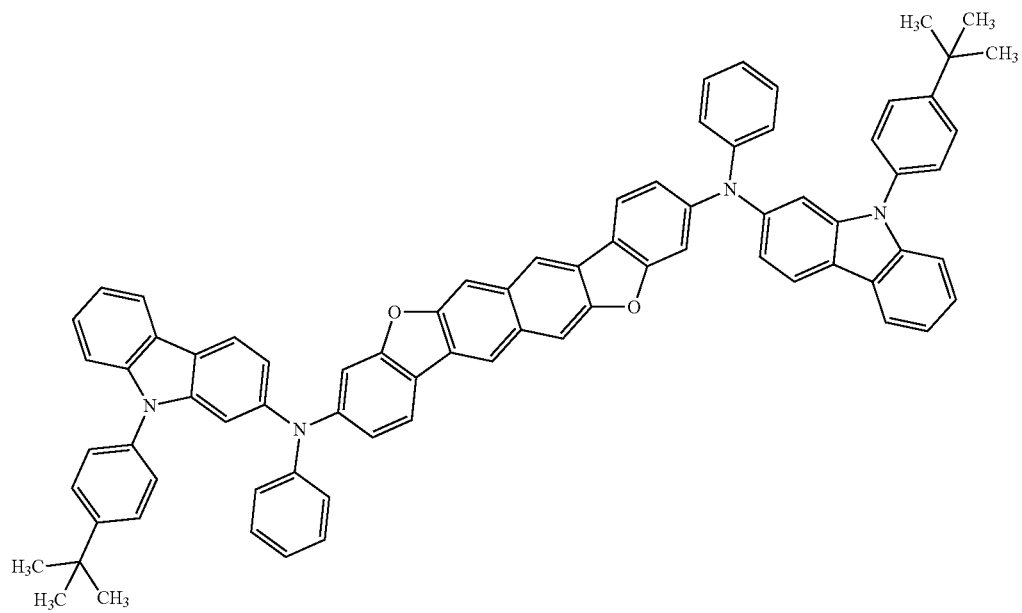
(136)
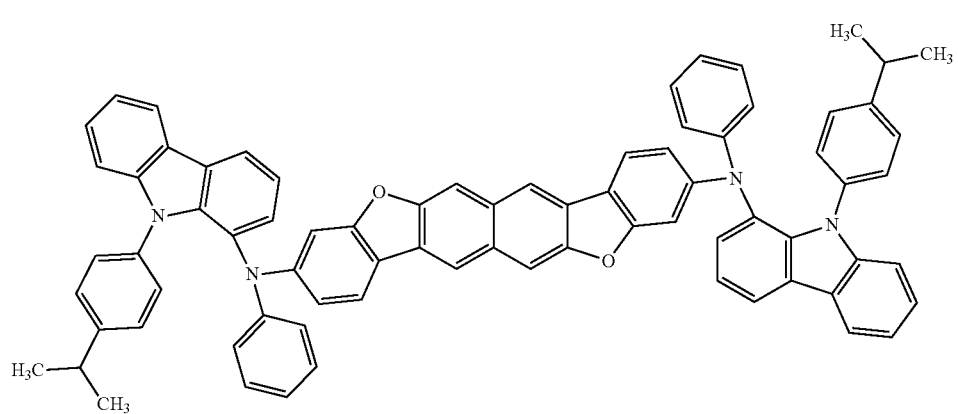
(137)

-continued
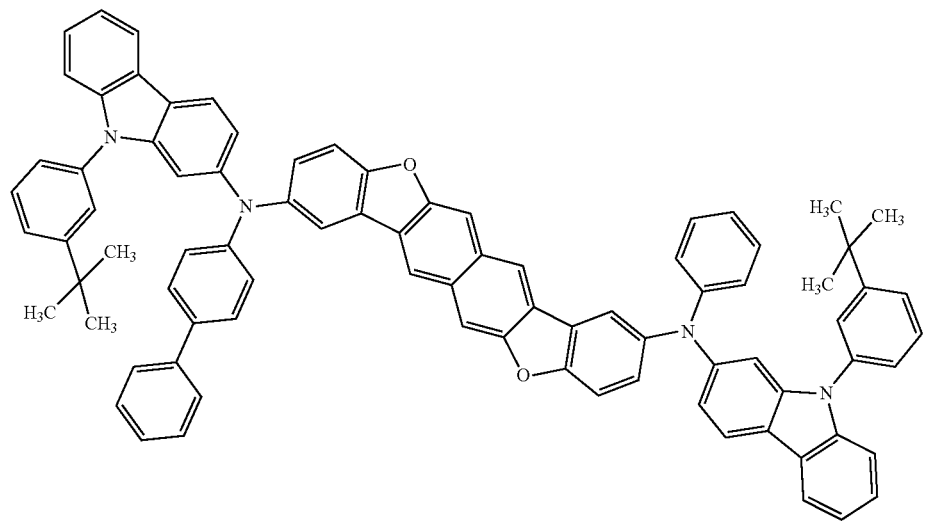
(138)
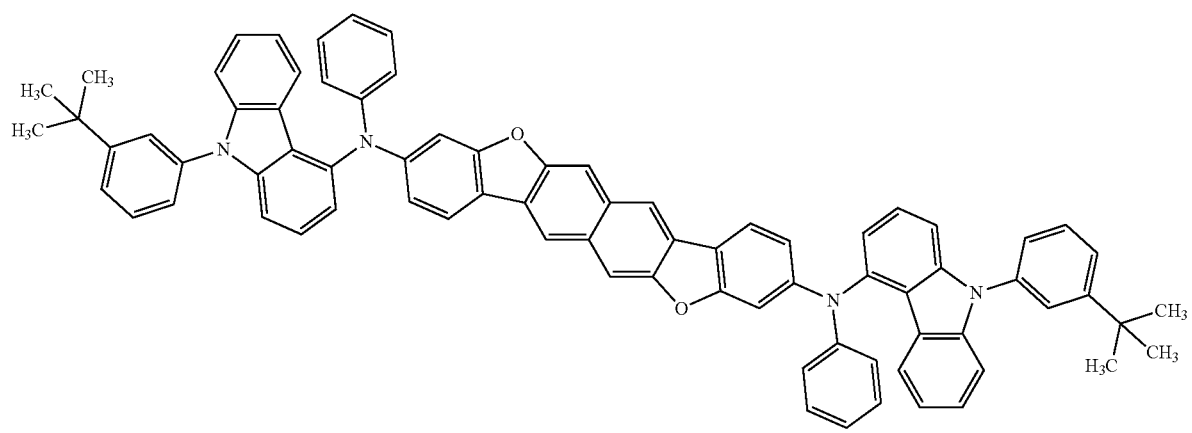
(139)
[Chemical Formula 20]
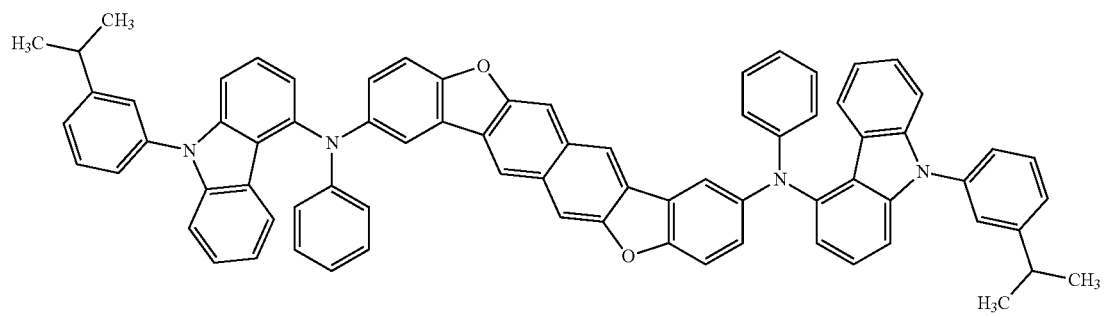
(140)

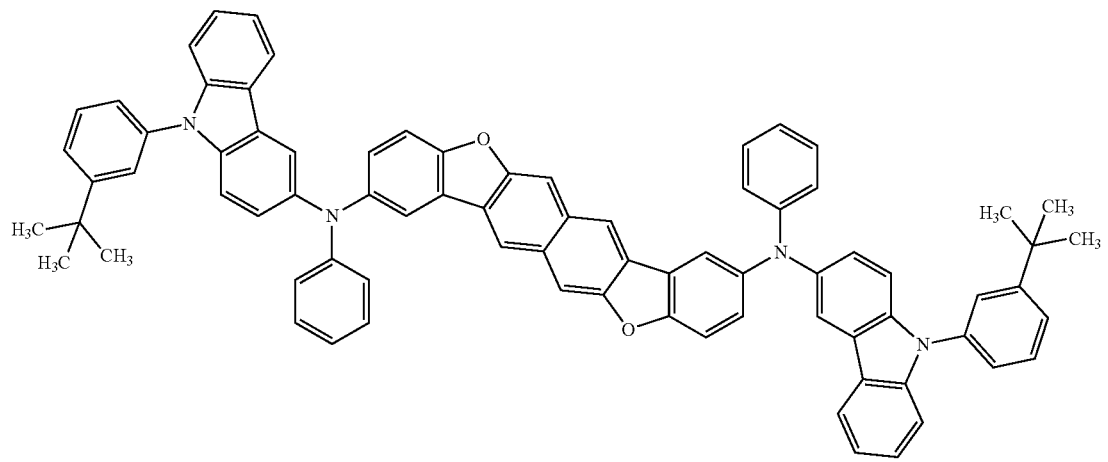
(141)
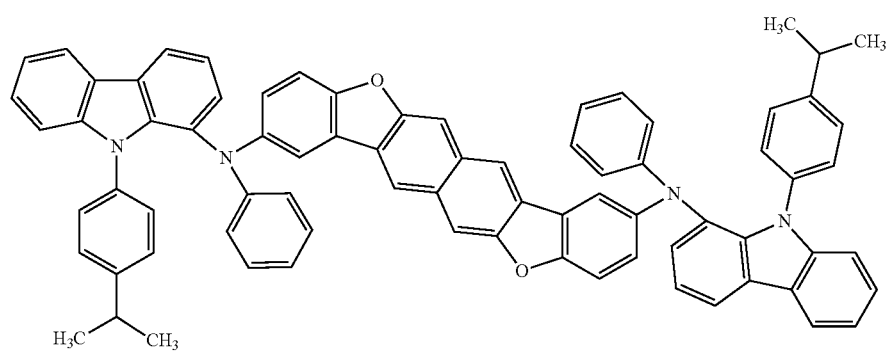
(142)
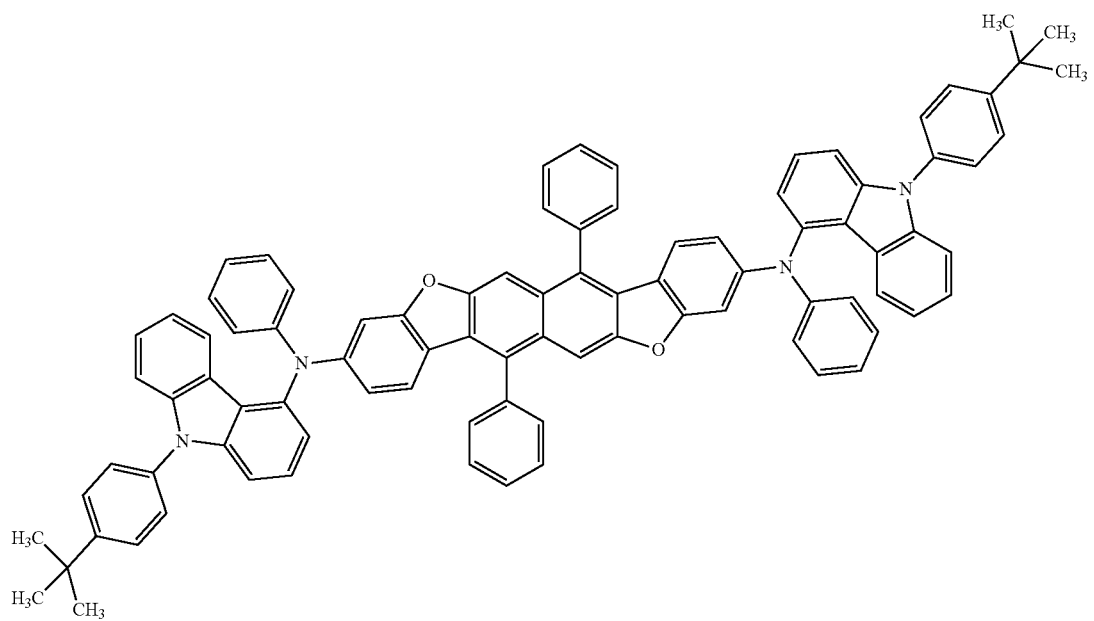
(143)

(144)
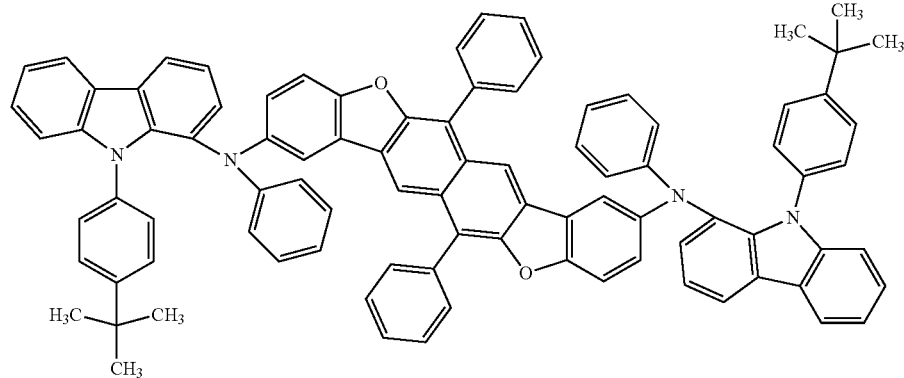
[Chemical Formula 21]
(145)
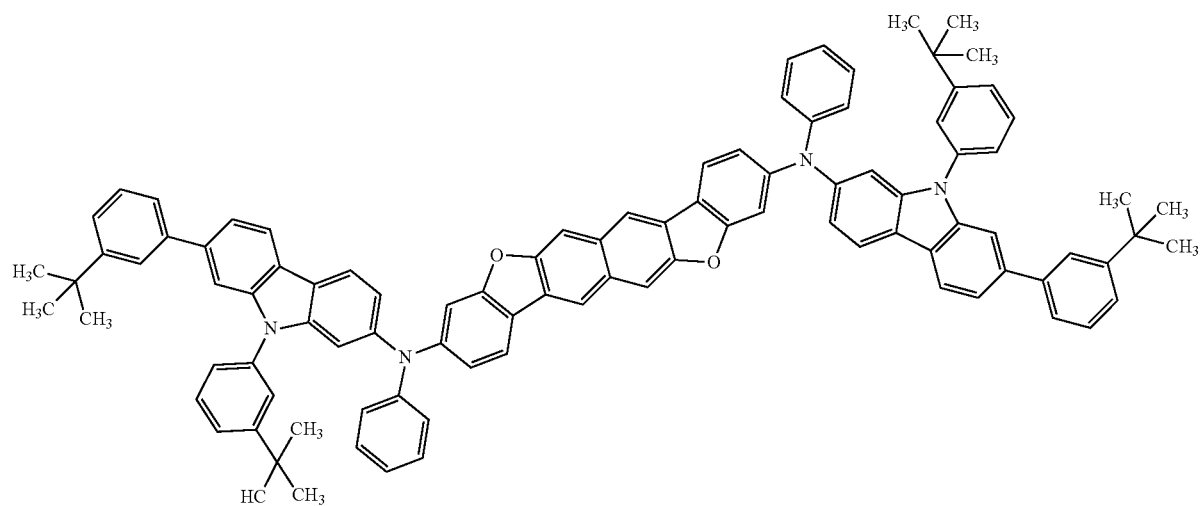
(146)
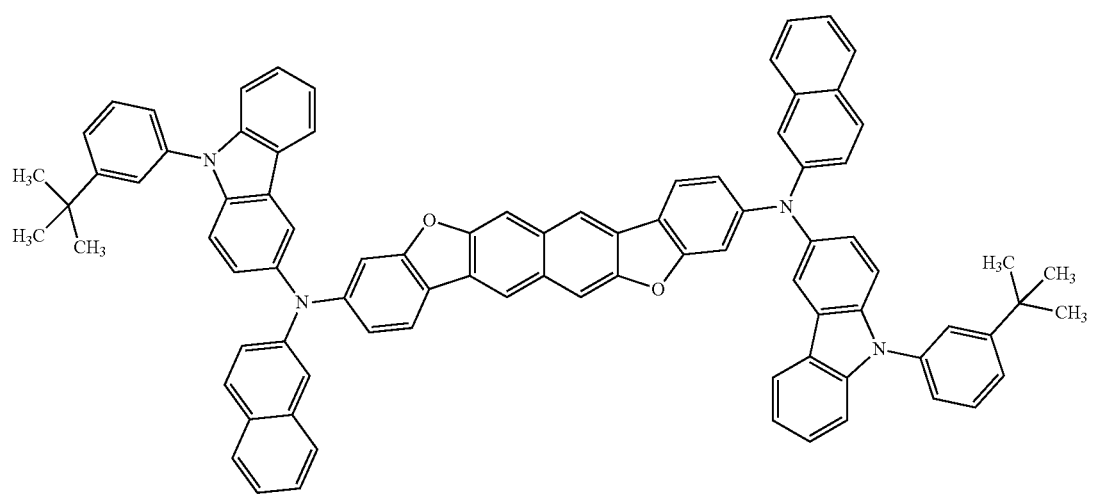

(147)
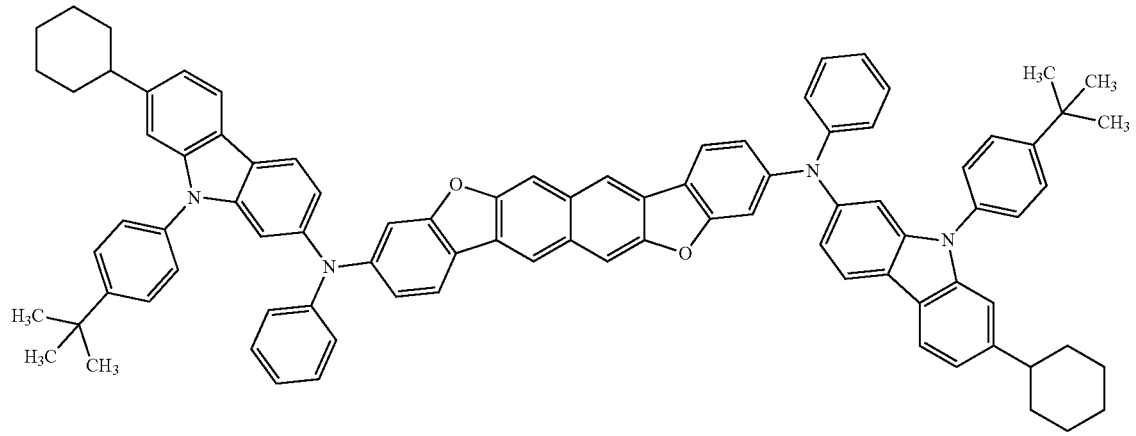
(148)
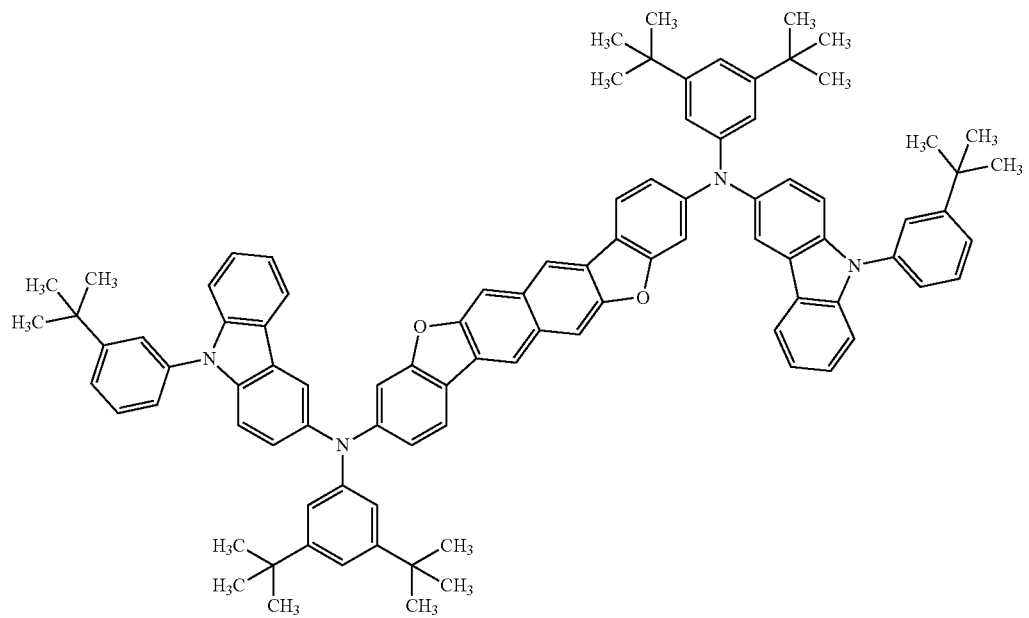
[Chemical Formula 22]
(149)
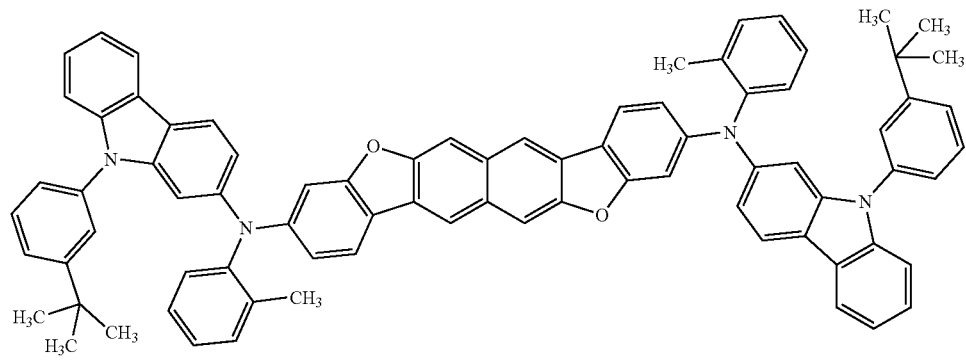

(150)
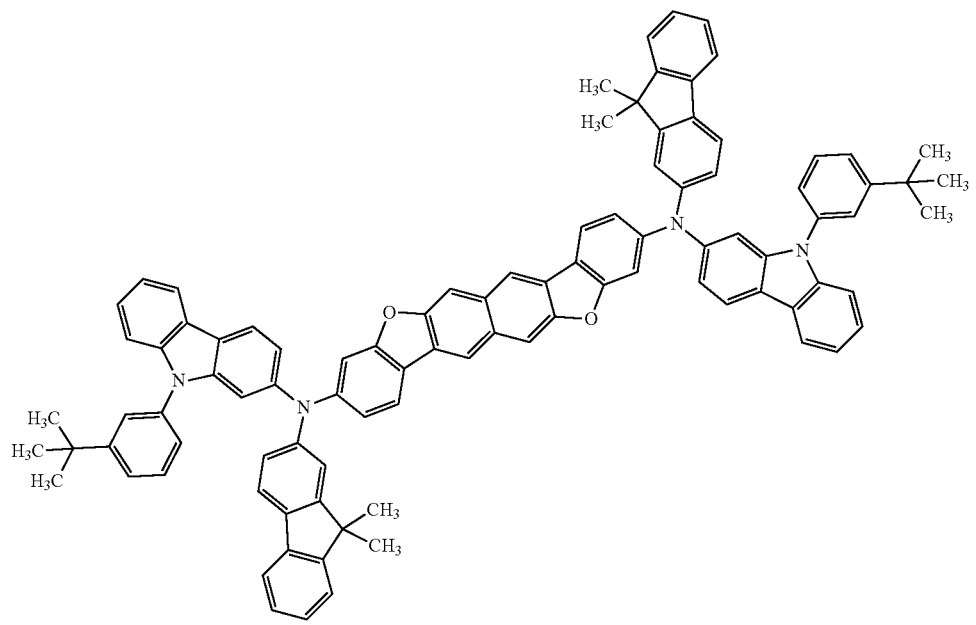
(151)
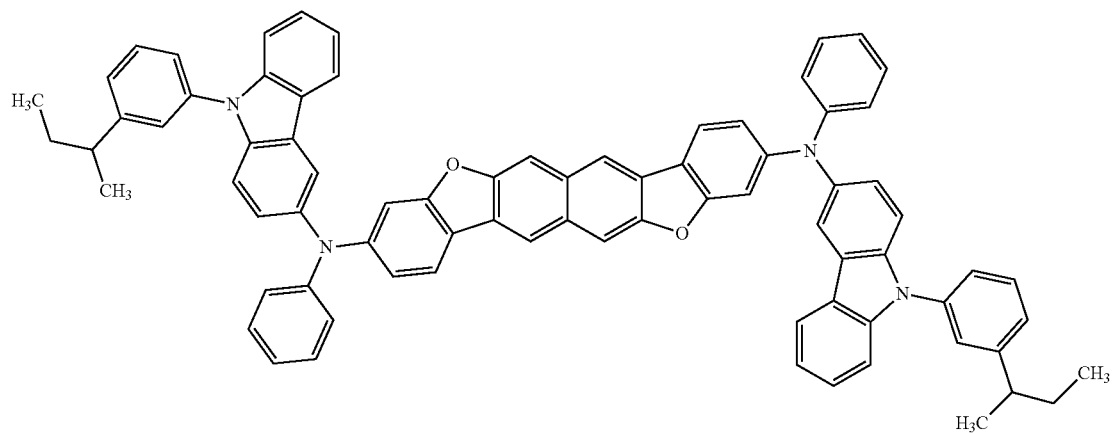
(152)
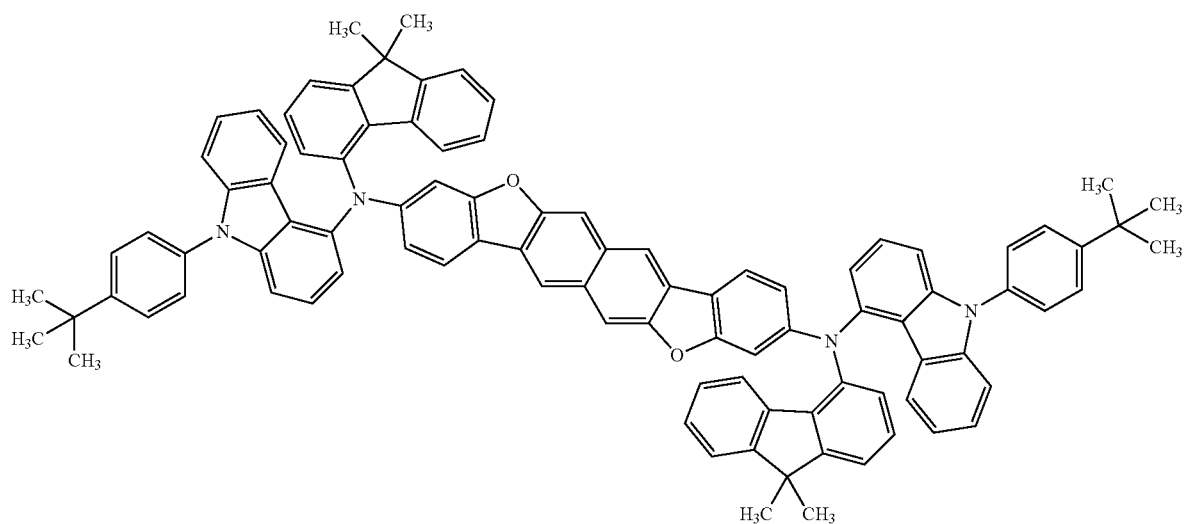

-continued
[Chemical Formula 23]
(153)
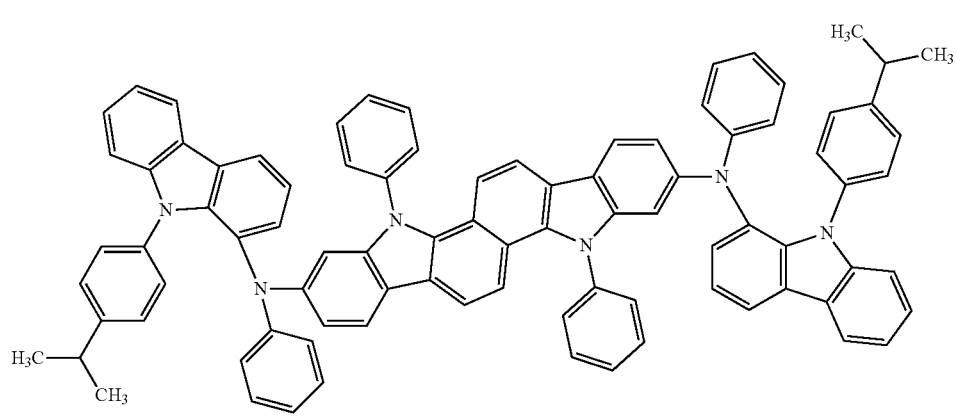
(154)
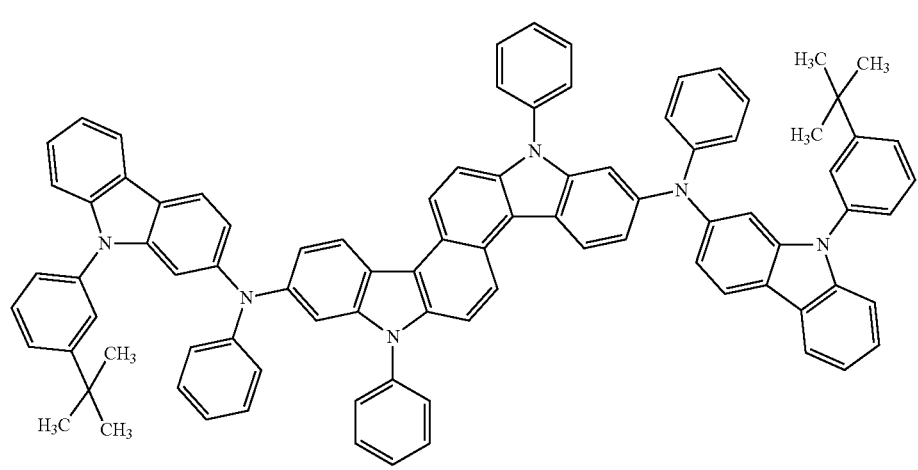
(155)
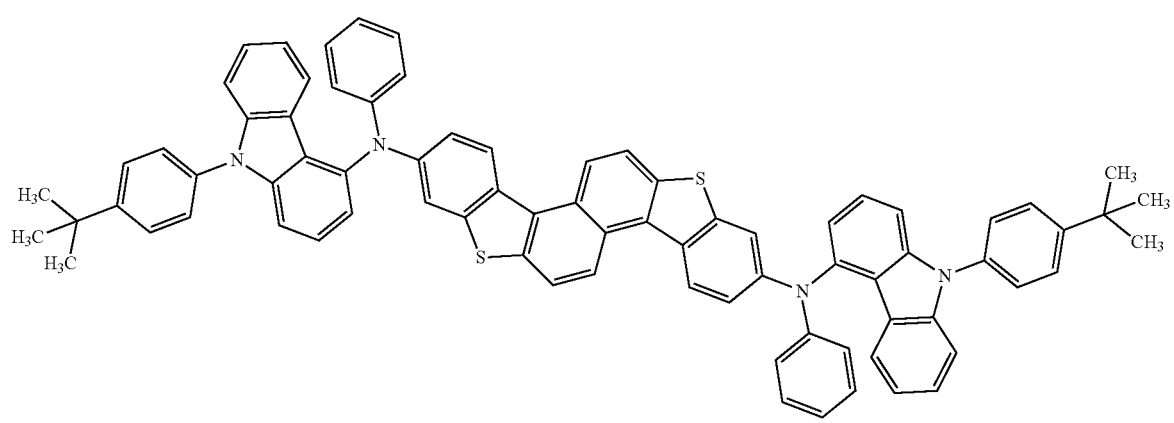

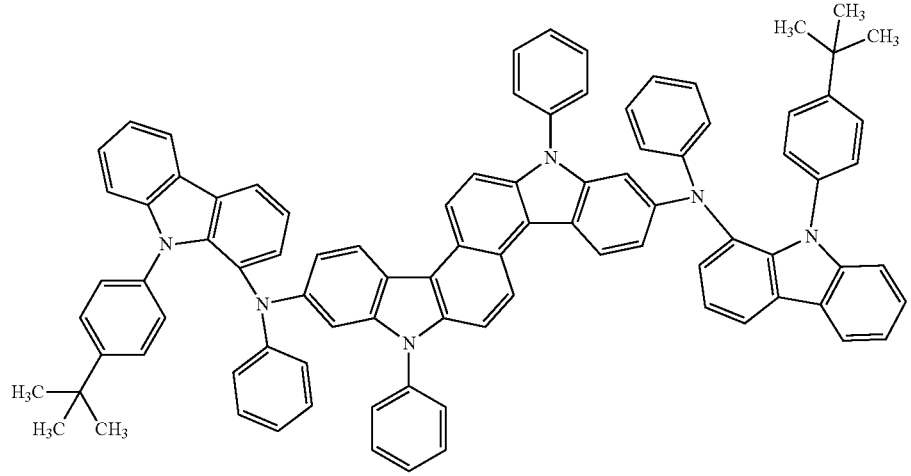
(156)
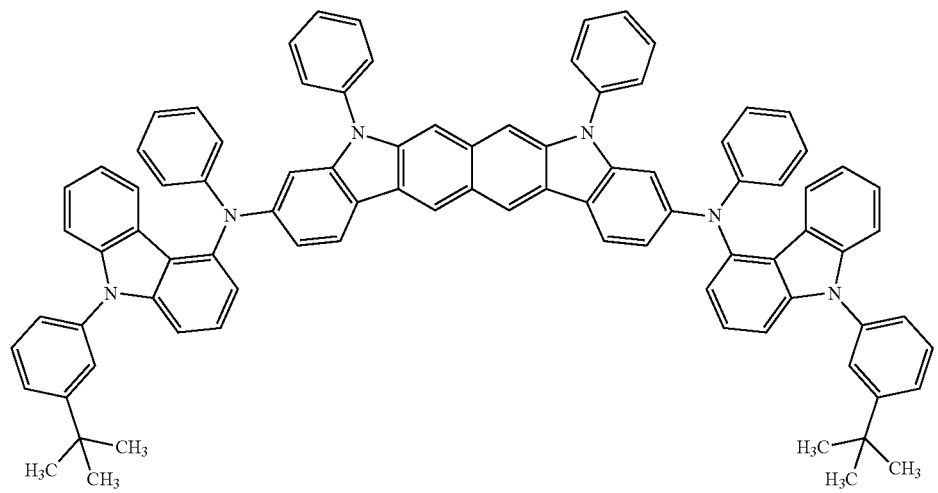
(157)
[Chemical Formula 24]
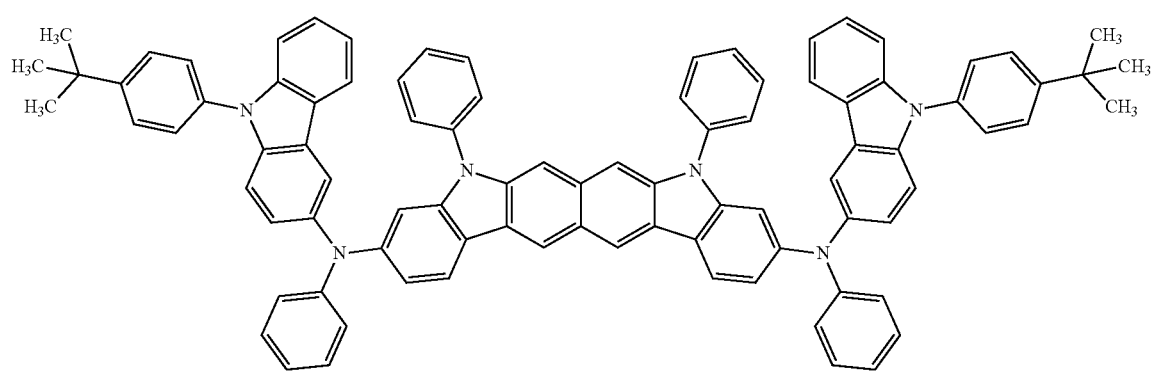
(158)

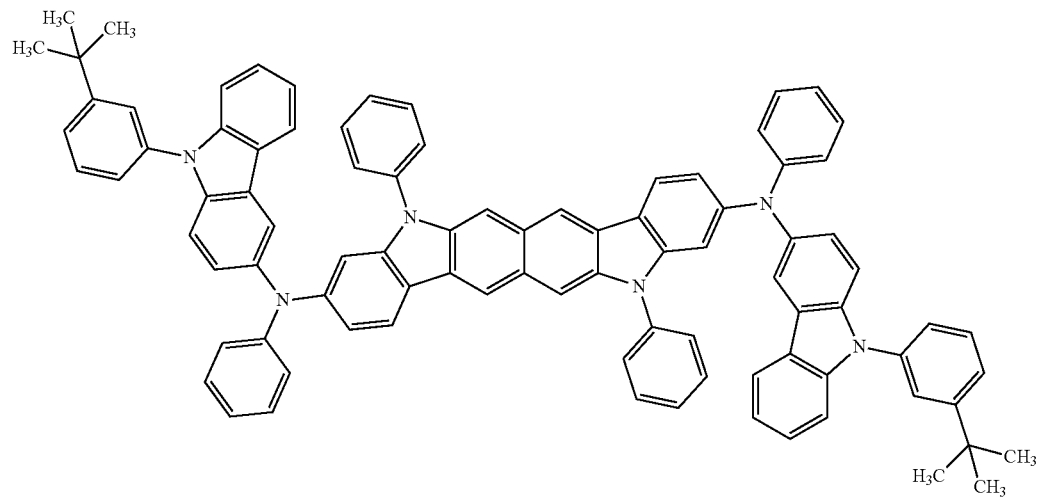
(159)
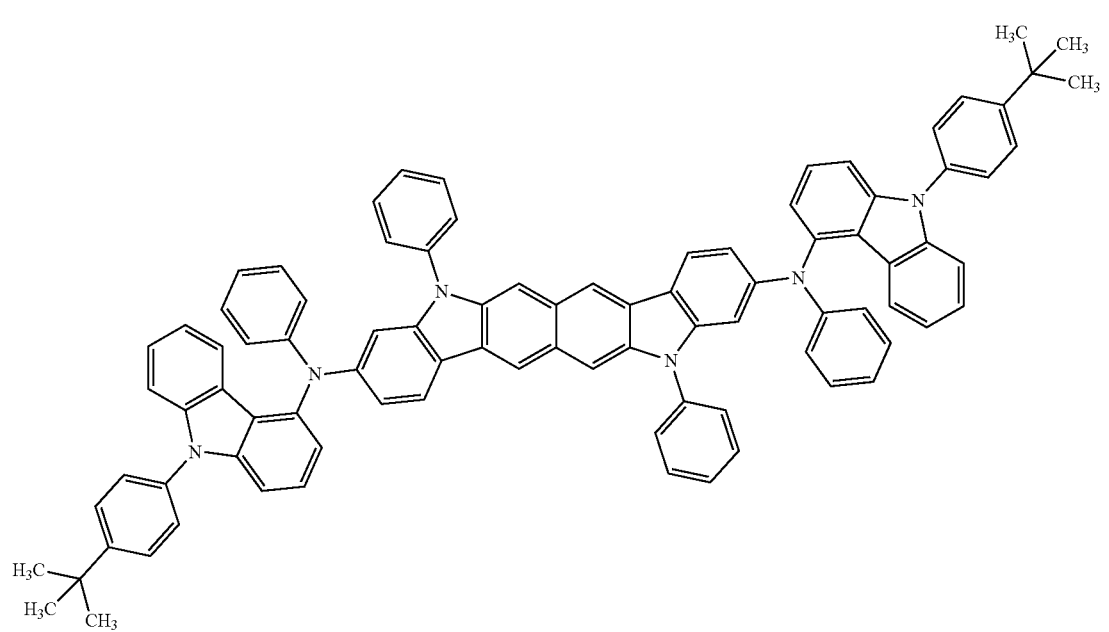
(160)

[Chemical Formula 25]
(161)
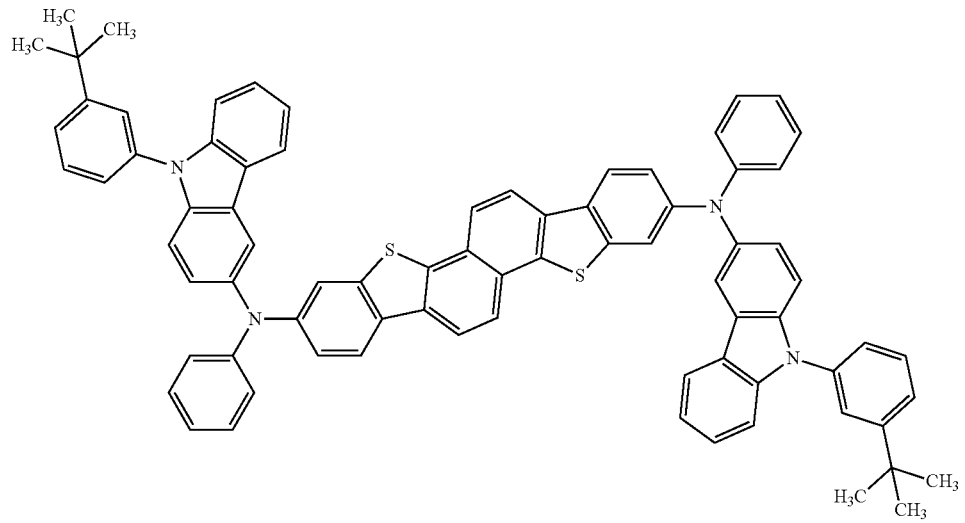
(162)
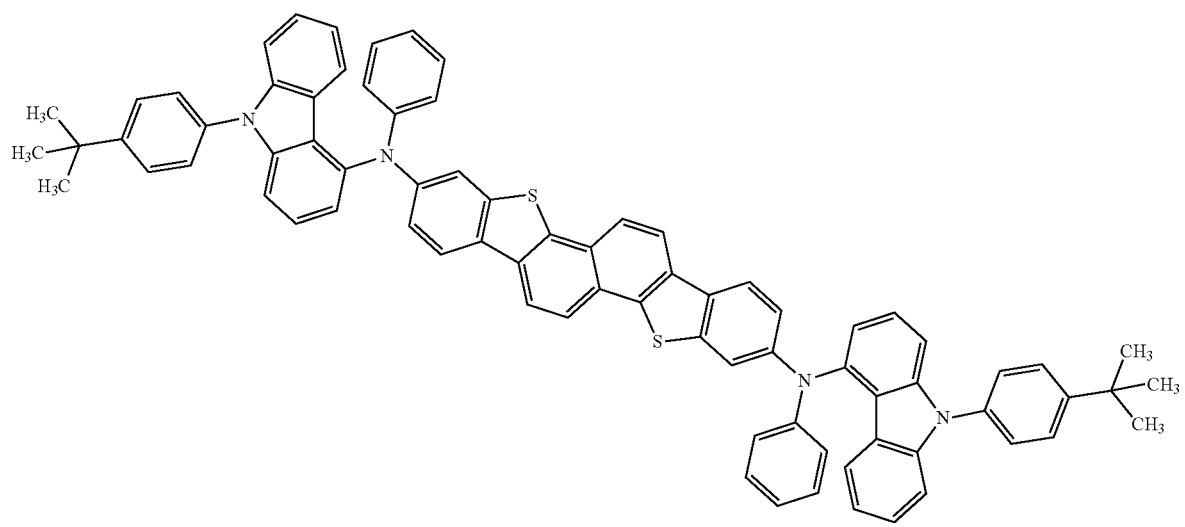
(163)
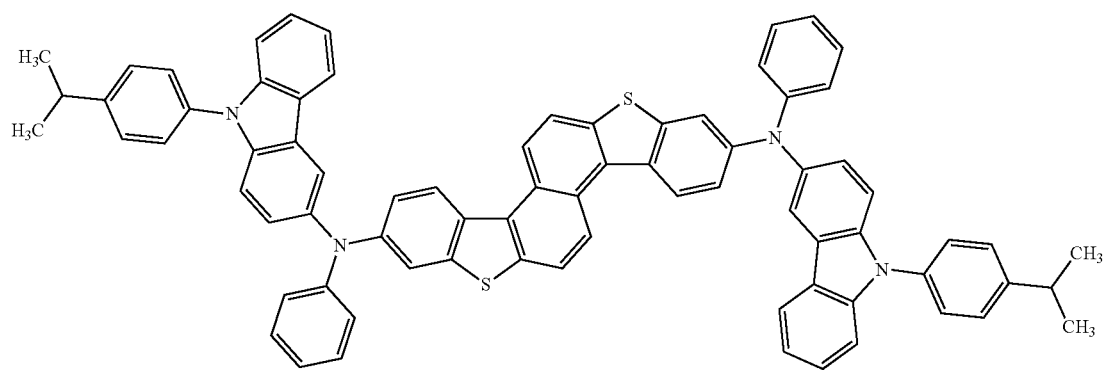

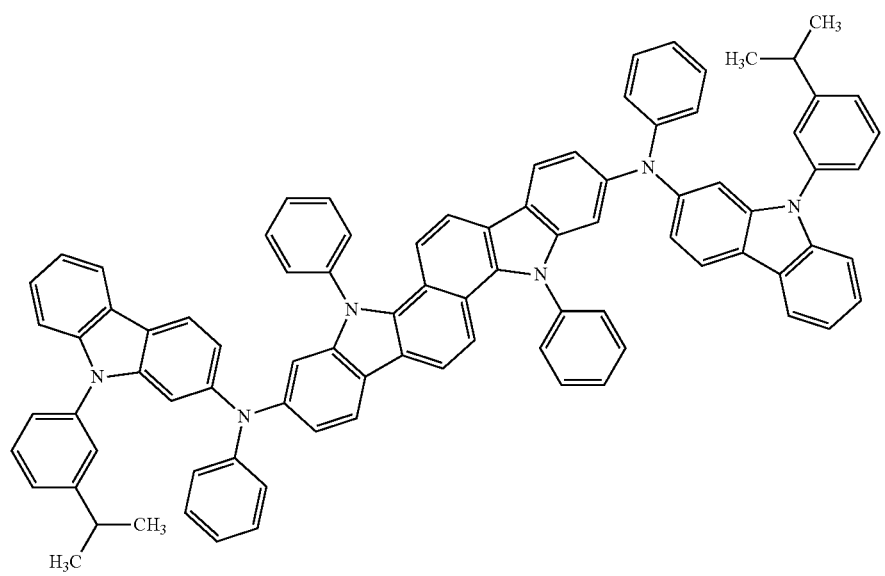
(164)
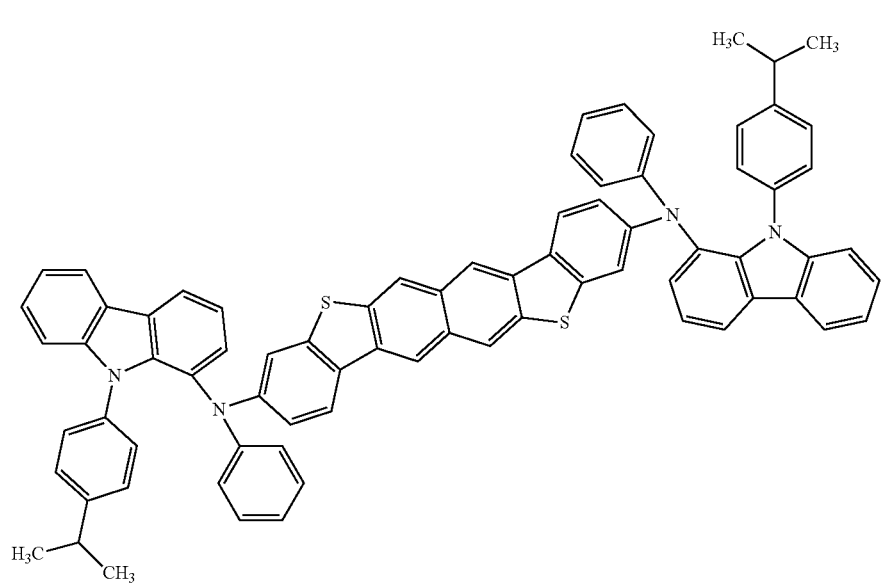
(165)
[Chemical Formula 26]
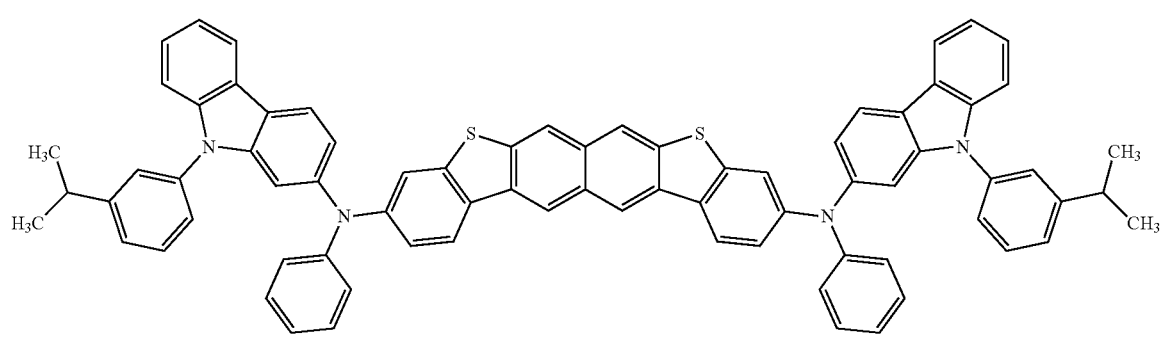
(166)

(167)
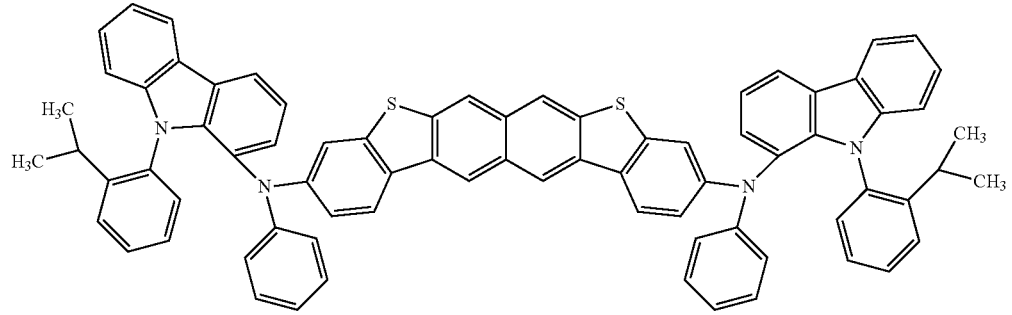
(168)
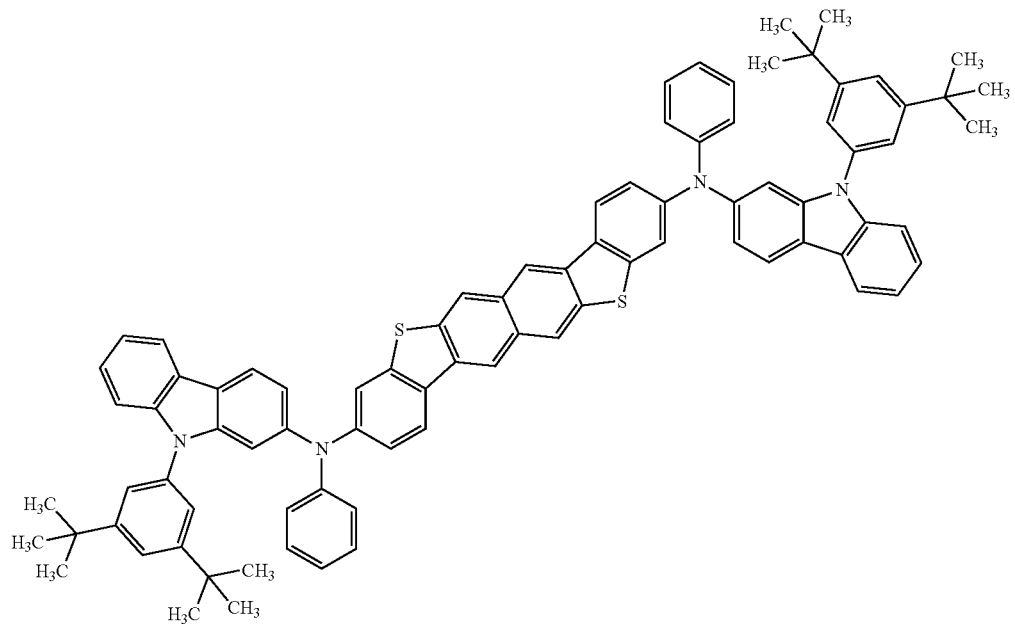
[Chemical Formula 27]
(169)
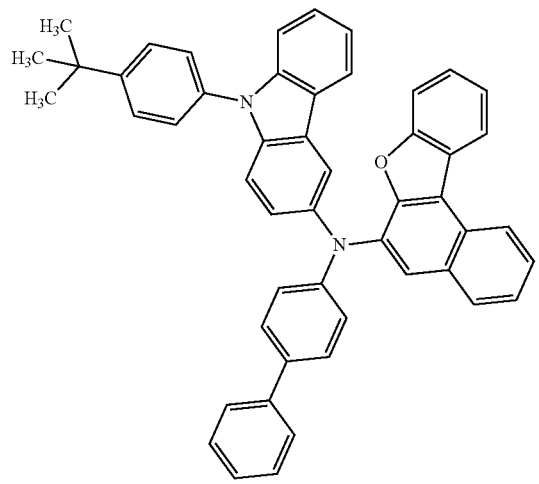
(170)
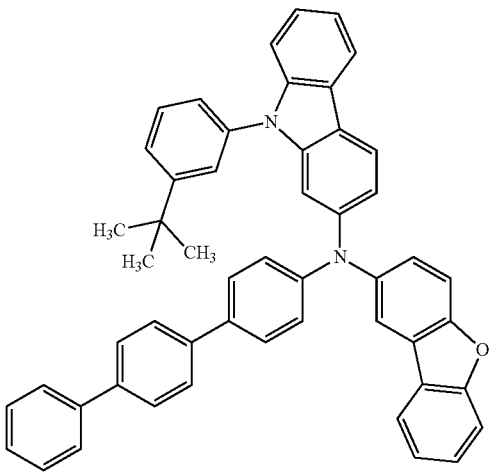

-continued
(171)
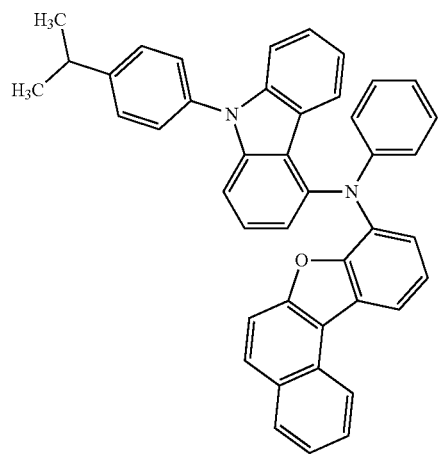
(172)
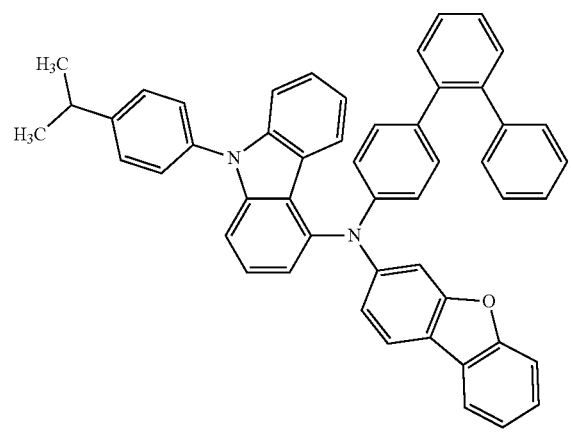
(173)
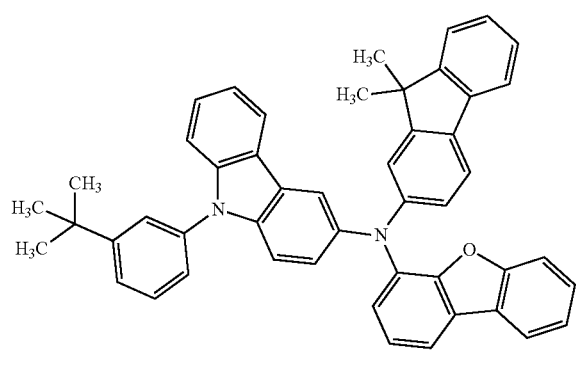
(174)
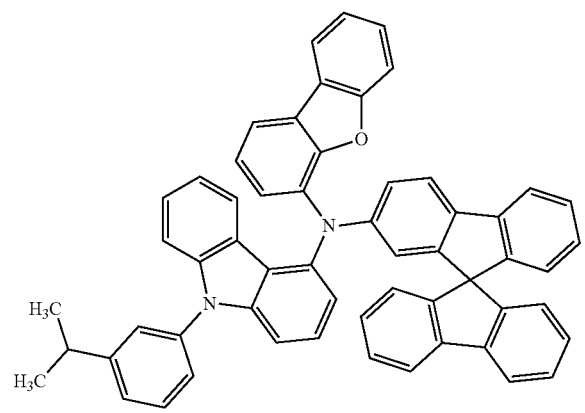
(175)
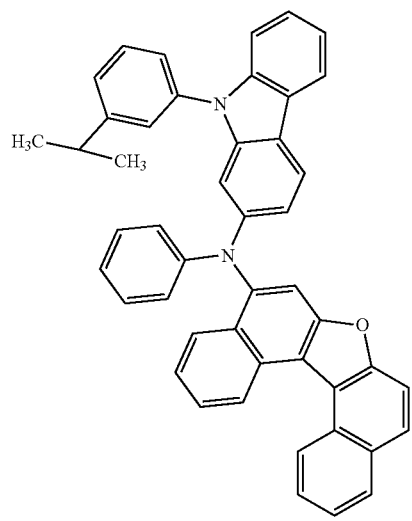
(176)
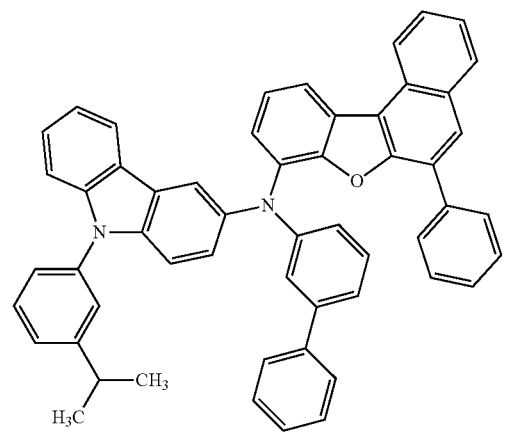

[Chemical Formula 28]
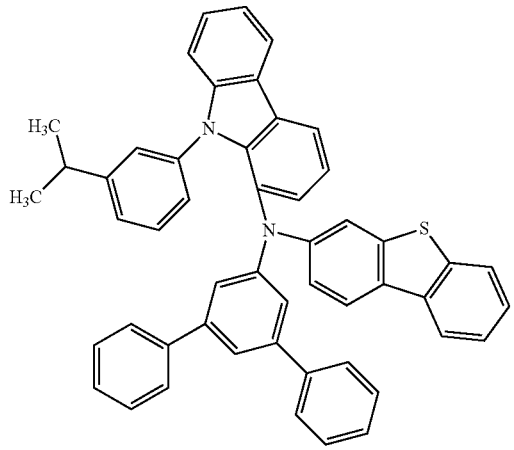
(177)
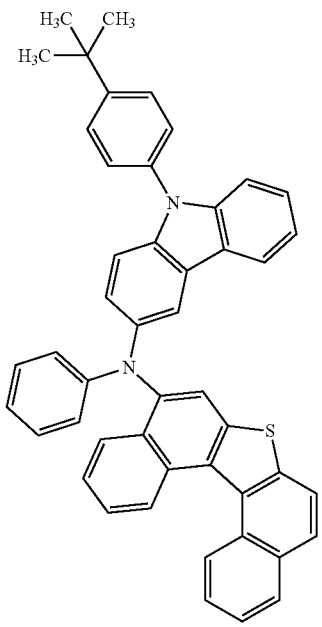
(178)
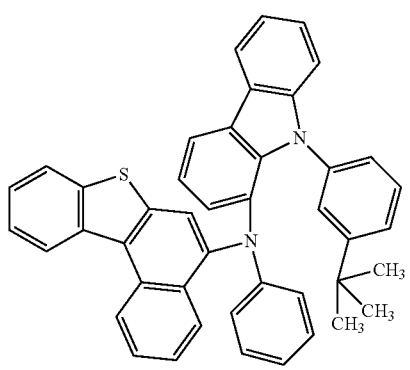
(179)
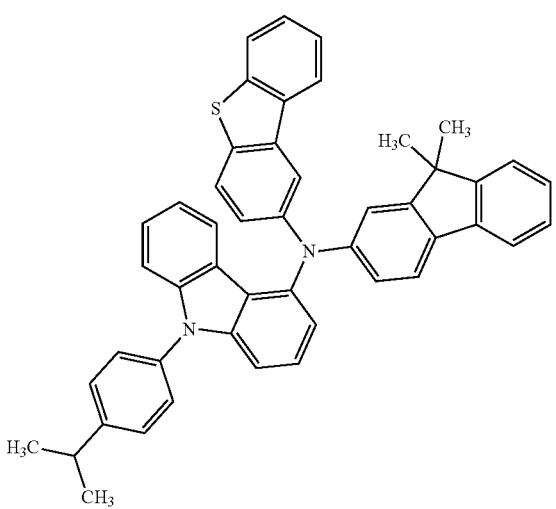
(180)

(181)
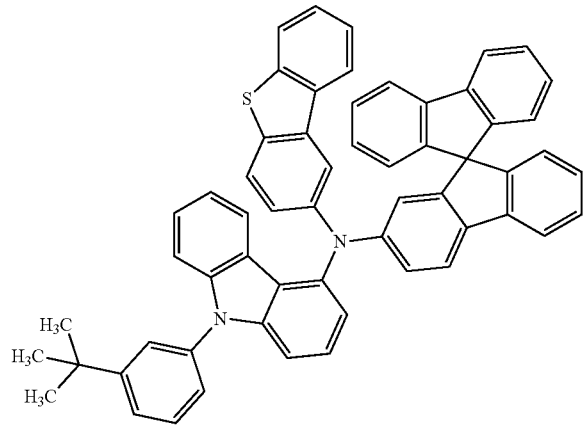
(182)
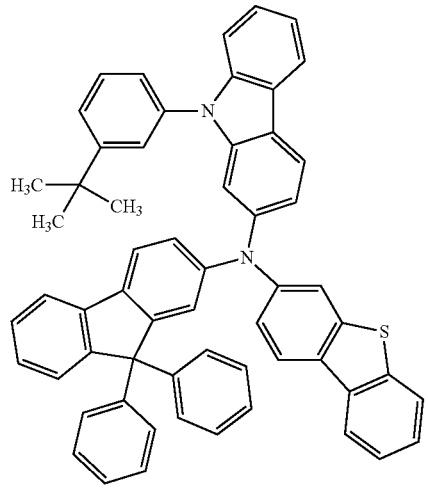
(183)
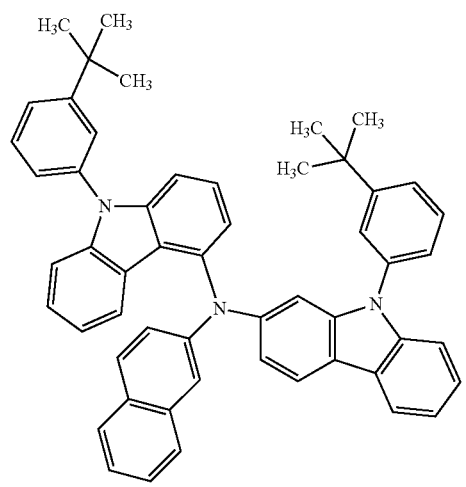
(184)
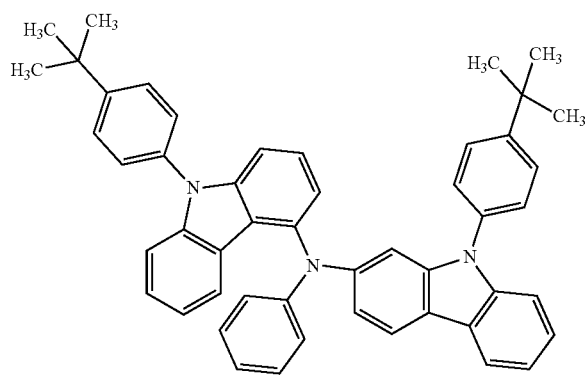

[Chemical Formula 29]
(185) 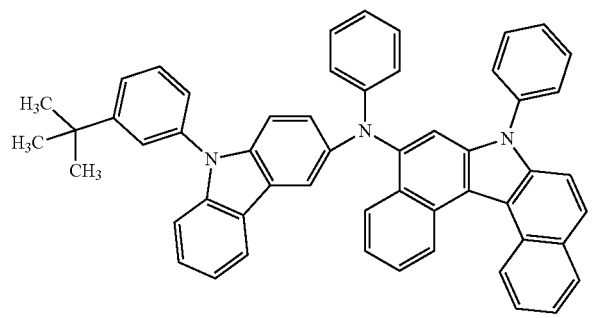
(186) 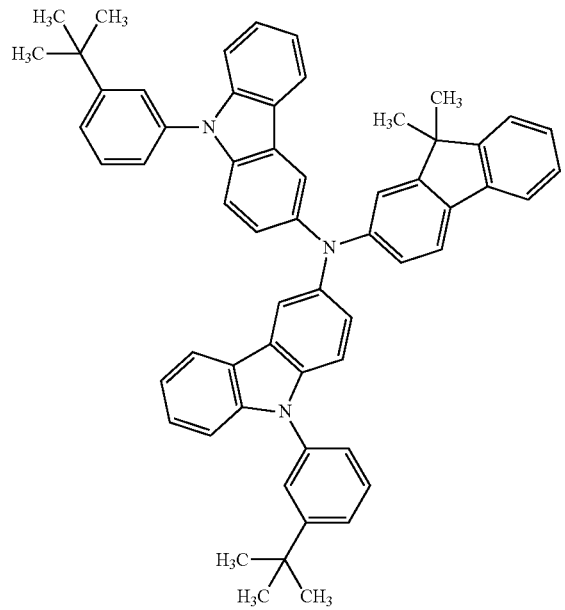
(187) 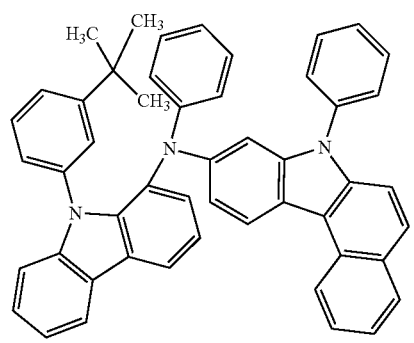
(188) 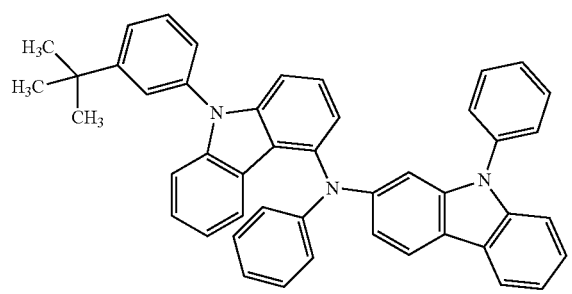
(189) 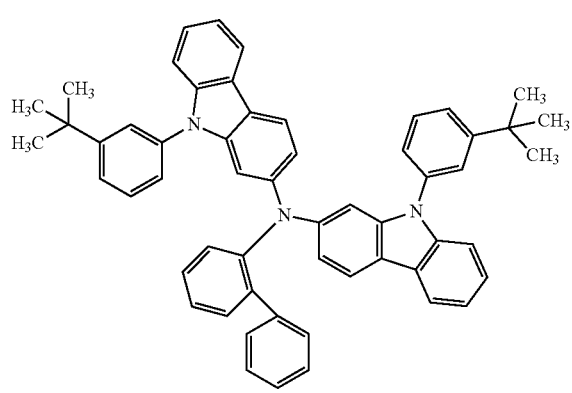
(190) 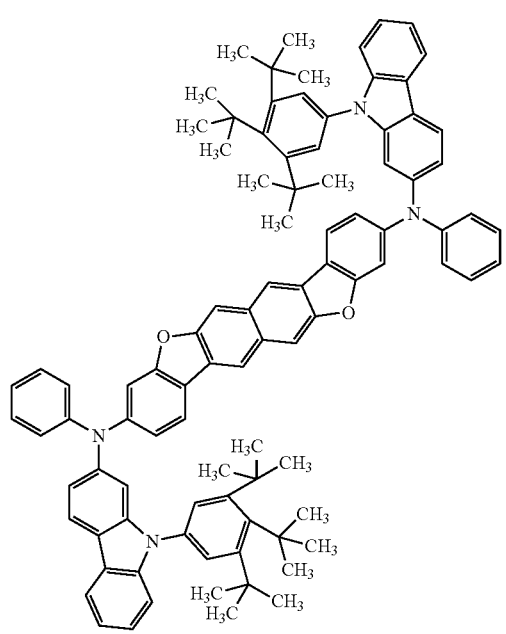

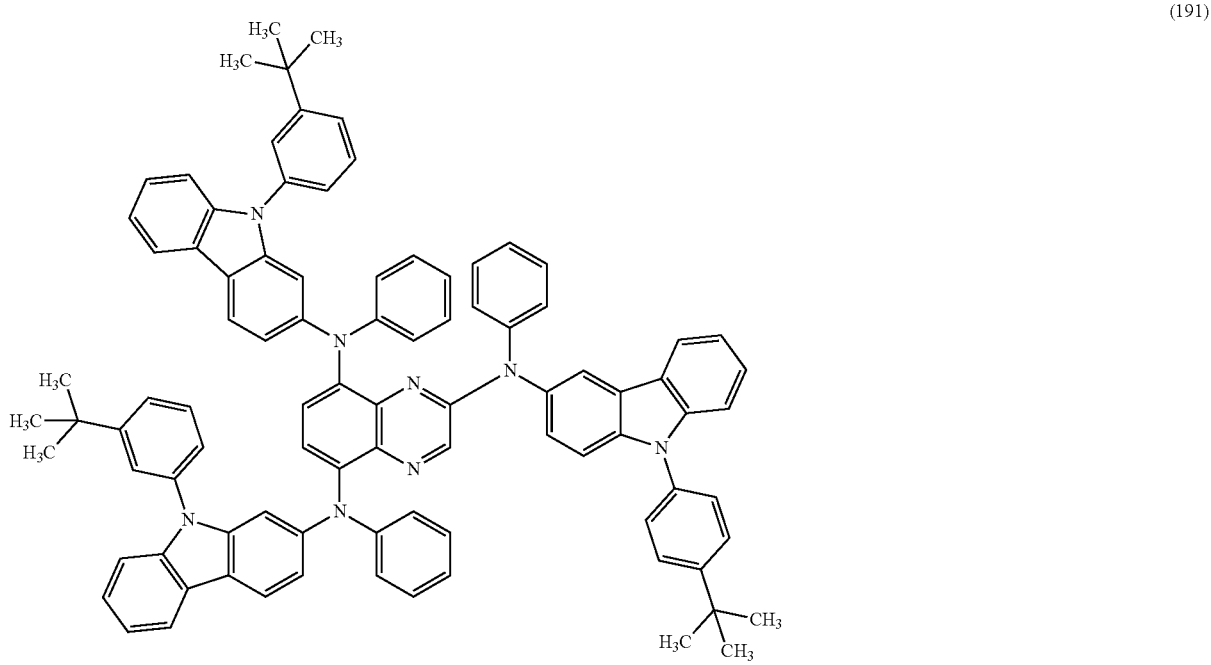

(191)

Then, one example of a method for synthesizing the above-described organic compound of the present invention will be described. The organic compound represented by General Formula (G1) is shown below. Note that $X^1$ to $X^5$, $R^1$ to $R^7$, $Ar^1$, $Ar^2$, and n in the following general formulae are the same as those described above, and thus are not described repeatedly.

[Chemical Formula 30]

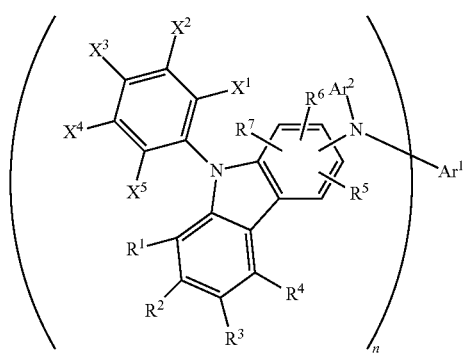

(G1)

The organic compound represented by General Formula (G1) can be obtained through a cross coupling reaction of a compound (a1) and an arylamine compound (a2) as shown in the following synthesis scheme. Examples of $B^1$ include a halogen group such as chlorine, bromine, or iodine, and a triflate group. Examples of $B^2$ include hydrogen and an organotin group.

[Chemical Formula 30]

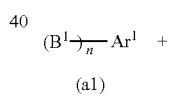

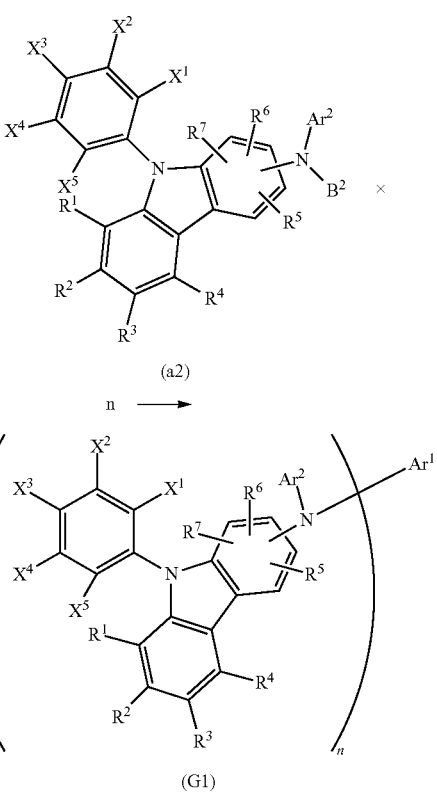

This reaction can proceed under a variety of conditions; for example, a synthesis method using a metal catalyst in the presence of a base can be employed. For example, the Ullmann coupling or the Buchwald-Hartwig reaction can be used.

Note that n equivalents of the compound (a2) are reacted with the compound (a1) here; however, in the case where n is 2 or more, that is, two or more substituents shown in parentheses in the compound (G1) are bonded to each other and when the substituents are not the same, the different kinds of compounds (a2) may be reacted with the compounds (a1) separately.

When n is 1, an organic compound represented by General Formula (g1) can be obtained through a cross coupling reaction between a compound (a3) and an arylamine compound (a4) or a cross coupling reaction between a compound (a5) and an arylamine compound (a6) as shown in the following synthesis scheme. Examples of B include a halogen group such as chlorine, bromine, or iodine, and a triflate group. Examples of $B^2$ include hydrogen and an organotin group.

[Chemical Formula 32]

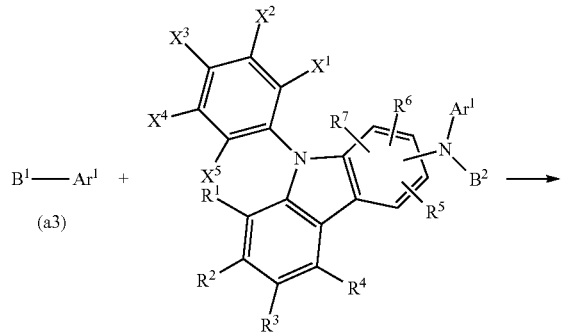

(a3)

(a4)

(g1)

[Chemical Formula 33]

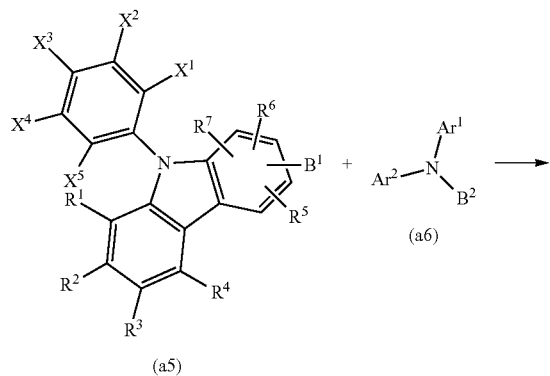

(a5)

(a6)

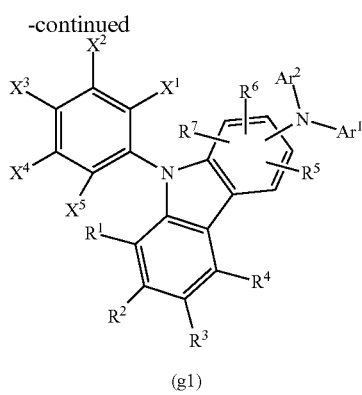

(g1)

The organic compound of one embodiment of the present invention can be synthesized in the above-described manner.

Embodiment 2

In this embodiment, a light-emitting device of one embodiment of the present invention is described.

FIG. 1A illustrates a light-emitting device of one embodiment of the present invention. The light-emitting device of one embodiment of the present invention includes a first electrode 101, a second electrode 102, and an EL layer 103. The EL layer 103 includes the organic compound described in Embodiment 1.

The EL layer 103 includes a light-emitting layer 113, and the light-emitting layer 113 contains alight-emitting material. A hole-injection layer 111 and/or a hole-transport layer 112 are/is provided between the light-emitting layer 113 and the first electrode 101. The organic compound represented by General Formula (G1-1) in Embodiment 1 is preferably used as the light-emitting material because it exhibits blue fluorescence efficiently.

The light-emitting layer 113 may contain a host material in addition to the light-emitting material. The host material is an organic compound having a carrier-transport property. The light-emitting layer 113 may contain one or more kinds of host materials. When a plurality of kinds of host materials are contained, the plurality of organic compounds are preferably an organic compound having an electron-transport property and an organic compound having a hole-transport property, in which case the carrier balance in the light-emitting layer 113 can be adjusted. Alternatively, the plurality of organic compounds may be organic compounds having an electron-transport property, and when the electron-transport properties are different, the electron-transport property of the light-emitting layer 113 can also be adjusted. Proper adjustment of the carrier balance enables a long-life light-emitting device to be provided. In addition, the plurality of organic compounds that are host materials may form an exciplex, or the host material and the light-emitting material may form an exciplex. The exciplex having an appropriate emission wavelength allows efficient energy transfer to the light-emitting material, achieving a light-emitting device with a high efficiency and a long lifetime.

Note that in FIG. 1A, the EL layer 103 includes an electron-transport layer 114 and an electron-injection layer 115 in addition to the light-emitting layer 113, the hole-injection layer 111, and the hole-transport layer 112; however, the structure of the light-emitting device is not limited thereto. Any of these layers may be omitted or a layer having another function may be included.

Next, examples of specific structures and materials of the above-described light-emitting device will be described. As described above, the light-emitting device of one embodiment of the present invention includes, between the pair of electrodes of the first electrode 101 and the second electrode 102, the EL layer 103 including a plurality of layers any of which contains the organic compound disclosed in Embodiment 1.

The first electrode 101 is preferably formed using any of metals, alloys, and conductive compounds with a high work function (specifically, higher than or equal to 4.0 eV), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the first electrode 101 in the EL layer 103, an electrode material can be selected regardless of its work function.

Although the EL layer 103 preferably has a stacked-layer structure, there is no particular limitation on the stacked-layer structure, and various layers such as a hole-injection layer, a hole-transport layer, a light-emitting layer, an electron-transport layer, an electron-injection layer, a carrier-blocking layer, an exciton-blocking layer, and a charge-generation layer can be employed. In this embodiment, two kinds of stacked-layer structure of the EL layer 103 are described: the structure illustrated in FIG. 1A, which includes the electron-transport layer 114 and the electron-injection layer 115 in addition to the hole-injection layer 111, the hole-transport layer 112, and the light-emitting layer 113; and the structure illustrated in FIG. 1B, which includes the electron-transport layer 114 and a charge-generation layer 116 in addition to the hole-injection layer 111, the hole-transport layer 112, and the light-emitting layer 113. Materials for forming each layer will be specifically described below.

The hole-injection layer 111 contains a substance having an acceptor property. Either an organic compound or an inorganic compound can be used as the substance having an acceptor property.

As the substance having an acceptor property, it is possible to use a compound having an electron-withdrawing group (a halogen group or a cyano group); for example, 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), or 2-(7-dicyanomethylene-1,3,4,5,6,8,9,10-octafluoro-7H-pyren-2-ylidene)malononitrile can be used. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group or a halogen group such as a fluoro group) has a very high electron-accepting property and thus is preferable. Specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α',α''-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and 4,4'-bis(N-{4-[N'-(3-methylphenyl)-N'-phenylamino]phenyl}-N-phenylamino)biphenyl (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) by the application of an electric field.

Alternatively, a composite material in which a material having a hole-transport property contains any of the above-described acceptor substances can be used for the hole-injection layer 111. With the use of a composite material in which a material having a hole-transport property contains an acceptor substance, a material used to form an electrode can be selected regardless of its work function. In other words, besides a material having a high work function, a material having a low work function can be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of $1 \times 10^{-6}$ cm$^2$/Vs or higher. Organic compounds which can be used as the material having a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N- carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis (4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9, 10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra (tert-butyl)perylene. Other examples include pentacene and coronene. The aromatic hydrocarbon may have a vinyl skeleton. Examples of the aromatic hydrocarbon having a vinyl skeleton include 4,4'-bis(2,2-diphenylvinyl)biphenyl (abbreviation: DPVBi) and 9,10-bis[4-(2,2-diphenylvinyl) phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide] (abbreviation: PTPDMA), and poly[N,N'-bis(4-butylphenyl)-N,N'-bis (phenyl)benzidine] (abbreviation: poly-TPD).

The material having a hole-transport property that is used in the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used. Note that these organic compound having an N,N-bis(4-biphenyl)amino group is preferable because a light-emitting device having a long lifetime can be fabricated. Specific examples of the organic compound include N-(4-biphenyl)-6,N-diphenylbenzo[b]naphtho[1,2-d]furan-8-amine (abbreviation: BnfABP), N,N-bis(4-biphenyl)-6-phenylbenzo[b] naphtho[1,2-d]furan-8-amine (abbreviation: BBABnf),4,4'-bis(6-phenylbenzo[b]naphtho[1,2-d]furan-8-yl)-4"-phenyltriphenylamine (abbreviation: BnfBB1BP), N,N-bis (4-biphenyl)benzo[b]naphtho[1,2-d]furan-6-amine (abbreviation: BBABnf(6)), N,N-bis(4-biphenyl)benzo[b] naphtho[1,2-d]furan-8-amine (abbreviation: BBABnf(8)), N,N-bis(4-biphenyl)benzo[b]naphtho[2,3-d]furan-4-amine (abbreviation: BBABnf(II) (4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6; 1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2-binaphthyl-2-yl)triphenylamine (abbreviation: BBA(βN2)B), 4,4'-diphenyl-4"-(7;2'-binaphthyl-2-yl)triphenylamine (abbreviation: BBA (βN2)B-03), 4,4'-diphenyl-4"-(4;2'-binaphthyl-1-yl) triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris (1,1'-biphenyl-4-yl)amine (abbreviation: YGTBi1BP-02), 4-[4'-(carbazole-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis ([1,1'-biphenyl]-4-yl)-9,9'-spirobi[9H-fluoren]-2-amine (abbreviation: BBASF), N,N-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]-9,9'-spirobi[9H-fluoren]-2-amine (abbreviation: PCBASF), N-(1,1'-biphenyl-4-yl)-9, 9-dimethyl-N-[4-(9-phenyl-9H-carbazol-3-yl)phenyl]-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)9,9'-spirobi-9H-fluoren-2-amine, and N,N-bis(9,9-dimehtyl-9H-fluoren-2-yl)-9,9'-spirobi-9H-fluoren-1-amine.

Note that it is further preferable that the material having a hole-transport property to be used in the composite material have a relatively deep HOMO level of greater than or equal to −5.7 eV and lower than or equal to −5.4 eV Using the material having a hole-transport property which has a relatively deep HOMO level in the composite material makes it easy to inject holes into the hole-transport layer 112 and to obtain a light-emitting device having a long lifetime.

Note that mixing the above composite material with a fluoride of an alkali metal or an alkaline earth metal (the proportion of fluorine atoms in a layer using the mixed material is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, which allows the light-emitting device to be driven at a low voltage. In addition, the organic compound having an acceptor property is easy to use because it is easily deposited by vapor deposition.

The hole-transport layer 112 is formed using a material having a hole-transport property. The material having a hole-transport property preferably has a hole mobility higher than or equal to $1 \times 10^{-6}$ cm$^2$Vs. Examples of the material having a hole-transport property include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-9,9'-spirobi[9H-fluoren]-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the material having a hole-transport property which is used in the composite material for the hole-injection layer 111 can also be suitably used as the material for the hole-transport layer 112. The organic compound described in Embodiment 1 has a hole-transport property, and thus can be used as a material for the hole-transport layer 112.

Since the organic compounds described in Embodiment 1 each have a low refractive index and include a bulky alkyl group, a film with a low refractive index can be obtained. Thus, a light-emitting device including the organic compound can have high light extraction efficiency and high emission efficiency.

The light-emitting layer 113 contains a light-emitting substance and a host material. The light-emitting layer 113 may additionally include other materials. Alternatively, the light-emitting layer 113 may be a stack of two layers with different compositions.

As the light-emitting substance, fluorescent substances, phosphorescent substances, substances exhibiting thermally activated delayed fluorescence (TADF), or other light-emitting substances may be used.

Examples of the material that can be used as a fluorescent substance in the light-emitting layer 113 include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPm), N,N'-bis(3-methylphenyl)-N,N'-bis[3-(9-phenyl-9H-fluoren-9-yl)phenyl]pyrene-1,6-diamine (abbreviation: 1,6mMemFLPAPm), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[j]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[j]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-(pyrene-1,6-diyl)bis[(6,N-diphenylbenzo[b]naphtho[1,2-d]furan)-8-amine] (abbreviation: 1,6BnfAPm-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino] naphtho[2,3-b;6,7-b']bisbenzofuran (abbreviation: 3,10FrA2Nbf(IV)-02). Condensed aromatic diamine compounds typified by pyrenediamine compounds such as 1,6FLPAPm, 1,6mMemFLPAPm, and 1,6BnfAPm-03 are particularly preferable because of their high hole-trapping properties, high emission efficiency, and high reliability. Other fluorescent substances can also be used. The organic compound represented by General Formula (G1-1) in Embodiment 1 can also be used as the fluorescent substance.

The light-emitting device of one embodiment of the present invention preferably includes any of the organic compounds described in Embodiment 1. The organic compounds described in Embodiment 1 are easy to purify and evaporate, and thus enable a highly reliable light-emitting device to be provided. Furthermore, the organic compounds can have higher thermophysical properties while keeping high color purity, and thus enable a light-emitting device with high color purity and high reliability to be provided.

Examples of the material that can be used when a phosphorescent substance is used as the light-emitting substance in the light-emitting layer 113 are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These compounds exhibit blue phosphorescence and have an emission spectrum peak at 440 nm to 520 nm.

Other examples include an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), [2-d3-methyl-8-(2-pyridinyl-κN)benzofuro[2,3-b]pyridine-κC]bis[2-(5-d3-methyl-2-pyridinyl-κN)phenyl-κC]iridium(III) (abbreviation: [Ir(5mppy-d3)$_2$(mbfpypy-d3)]), [2-d3-methyl-(2-pyridinyl-κN)benzofuro[2,3-b]pyridine-κC]bis[2-(2-pyridinyl-κN)phenyl-κC]iridium(III) (abbreviation: [Ir(ppy)$_2$(mbfpypy-d3)]); and a rare earth metal complex such as tris(acetylacetonato) (monophenanthroline)terbium(III) (abbreviation: [Tb(acac)$_3$(Phen)]). These are mainly compounds that exhibit green phosphorescence and have an emission spectrum peak at 500 nm to 600 nm. Note that an organometallic iridium complex having a pyrimidine skeleton has distinctively high reliability and emission efficiency and thus is particularly preferable.

Other examples include organometallic iridium complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato(dipivaloylmethanato)iridium(III) (abbreviation: [Ir(d1npm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato(monophenanthroline)europium(III) (abbreviation: [Eu(TTA)$_3$(Phen)]). These compounds exhibit red phosphorescence having an emission spectrum peak at 600 nm to 700 nm. Furthermore, the organometallic iridium complexes having a pyrazine skeleton can provide red light emission with favorable chromaticity.

Besides the above phosphorescent compounds, known phosphorescent substances may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl₂OEP), which are represented by the following structural formulae.
[Chemical Formula 34]
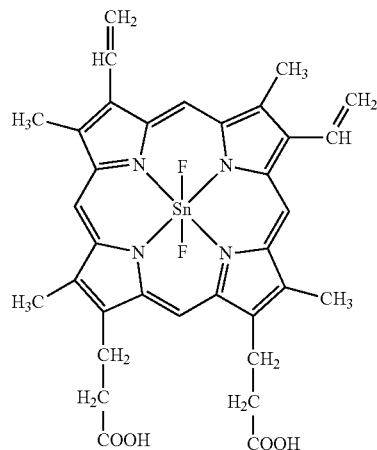
SnF₂(Proto IX)
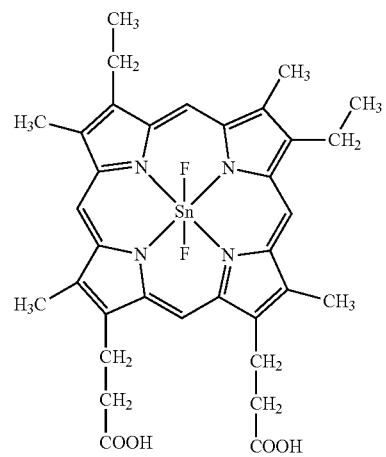
SnF₂(Meso IX)
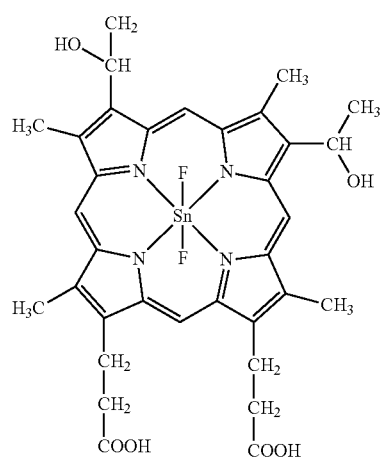
SnF₂(Hemato IX)
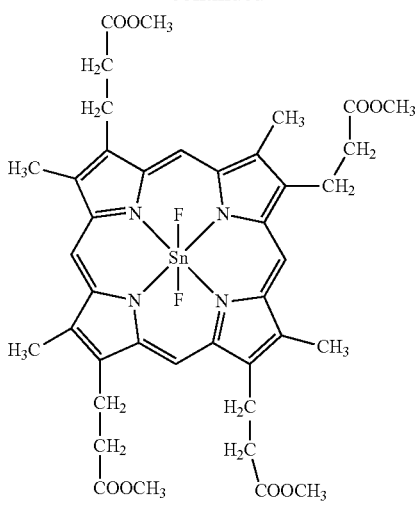
SnF₂(Copro III-4Me)
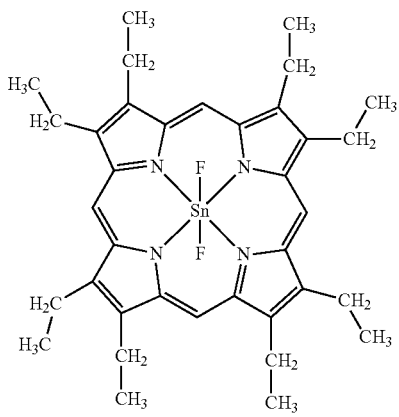
SnF₂(OEP)
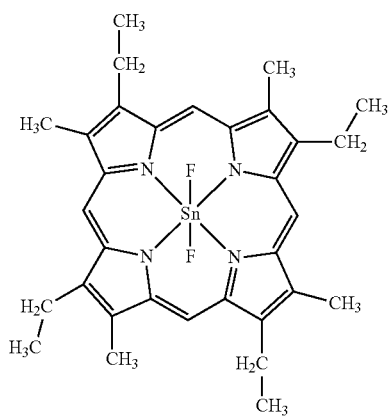
SnF₂(Etio I)

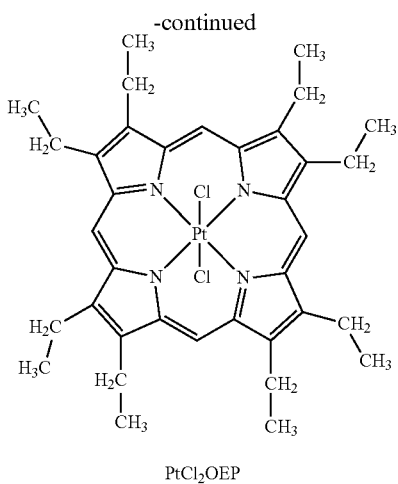

PtCl₂OEP

Alternatively, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Such a heterocyclic compound is preferable because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high accepting properties and high reliability. Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. A dibenzofuran skeleton is preferable as a furan skeleton, and a dibenzothiophene skeleton is preferable as a thiophene skeleton. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 35]

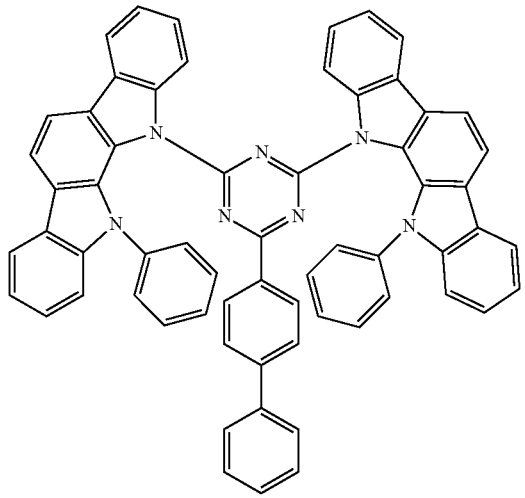

PIC-TRZ

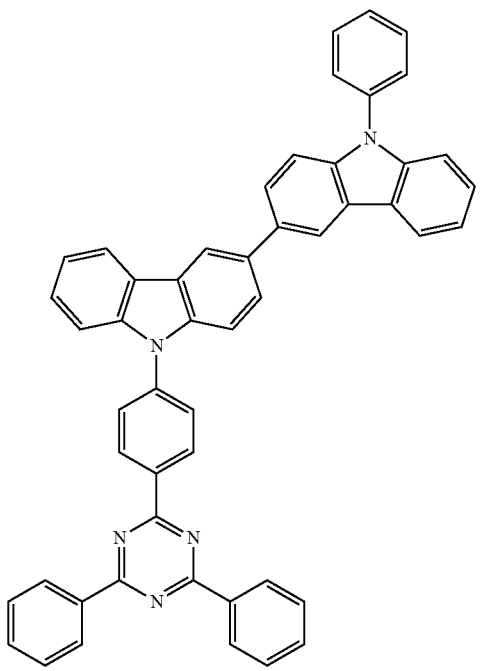

PCCzPTzn

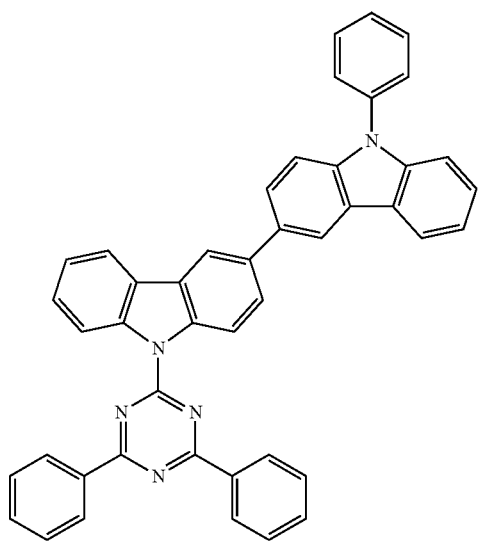

PCCzTzn

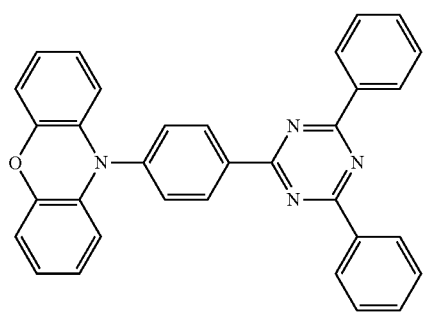

PXZ-TRZ

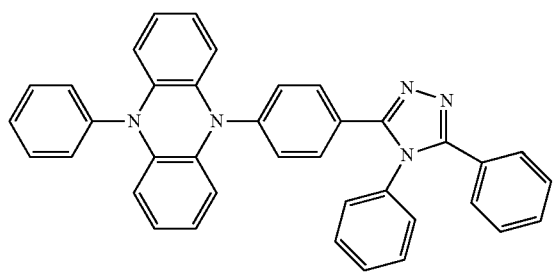

PPZ-3TPT

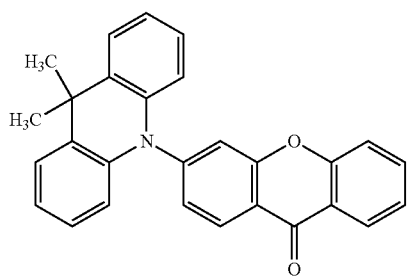

ACRXTN

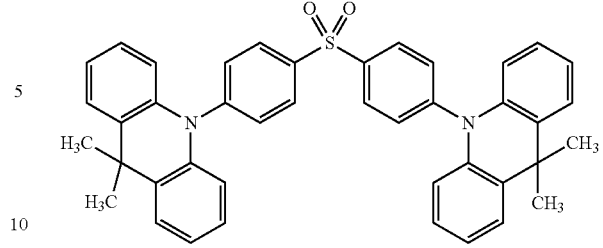

DMAC-DPS

ACRSA

Note that a TADF material is a material having a small difference between the S1 level and the T1 level and a function of converting triplet excitation energy into singlet excitation energy by reverse intersystem crossing. Thus, a TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy.

A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When a TADF material is used as the light-emitting substance, the S1 level of the host material is preferably higher than that of the TADF material. In addition, the T1 level of the host material is preferably higher than that of the TADF material.

As the host material in the light-emitting layer, various carrier-transport materials such as materials having an electron-transport property, materials having a hole-transport property, and the TADF materials can be used.

The material having a hole-transport property is preferably an organic compound having an aromatic amine skeleton or a π-electron rich heteroaromatic ring skeleton. Examples of the material include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-9,9'-spirobi[9H-fluoren]-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage.

As the material having an electron-transport property, metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); or an organic compound having a π-electron deficient heteroaromatic ring skeleton is preferable. Examples of the organic compound having a π-electron deficient heteroaromatic ring skeleton include 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-TH-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,8-Bis[3-(dibenzothiophen-4-yl)phenyl]-benzo[h]quinazoline (abbreviation: 4,8mDBtP2Bqn); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton and the heterocyclic compound having a pyridine skeleton have high reliability and thus are preferable. In particular, the heterocyclic compound having a diazine (pyrimidine or pyrazine) skeleton has a high electron-transport property to contribute to a reduction in driving voltage.

As the TADF material that can be used as the host material, the above materials mentioned as the TADF material can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. Here, the TADF material functions as an energy donor, and the light-emitting substance functions as an energy acceptor.

This is very effective in the case where the light-emitting substance is a fluorescent substance. In that case, the S level of the TADF material is preferably higher than that of the fluorescent substance in order that high emission efficiency be achieved. Furthermore, the T1 level of the TADF material is preferably higher than the S1 level of the fluorescent substance. Therefore, the T1 level of the TADF material is preferably higher than that of the fluorescent substance.

It is also preferable to use a TADF material that emits light whose wavelength overlaps with the wavelength on a lowest-energy-side absorption band of the fluorescent substance. This enables smooth transfer of excitation energy from the TADF material to the fluorescent substance and accordingly enables efficient light emission, which is preferable.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no 7 bond and a saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituents having no 7 bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a 7 bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the light-emitting substance, a material having an anthracene skeleton is favorably used as the host material. The use of a substance having an anthracene skeleton as the host material for the fluorescent substance makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-βNPAnth). Note that CzPA, cgDBCzPA, 2mBnfPPA, and PCzPA have excellent characteristics and thus are preferably selected.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1. Note that the organic compounds described in Embodiment 1 can be used as a material having a hole-transport property in the mixed host material.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed of these mixed materials. When these mixed materials are selected so as to form an exciplex that exhibits light emission whose wavelength overlaps with the wavelength on a lowest-energy-side absorption band of the light-emitting substance, energy can be transferred smoothly and light emission can be obtained efficiently, which is preferable. The use of such a structure is preferable because the driving voltage can also be reduced.

Note that at least one of the materials forming an exciplex may be a phosphorescent substance. In this case, triplet excitation energy can be efficiently converted into singlet excitation energy by reverse intersystem crossing.

Combination of a material having an electron-transport property and a material having a hole-transport property whose HOMO level is higher than or equal to that of the material having an electron-transport property is preferable for forming an exciplex efficiently. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the material having a hole-transport property and the material having an electron-transport property are mixed is shifted to the longer wavelength side than the emission spectra of each of the materials (or has another peak on the longer wavelength side) observed by comparison of the emission spectra of the material having a hole-transport property, the material having an electron-transport property, and the mixed film of these materials, for example. Alternatively, the formation of an exciplex can be confirmed by a difference in transient response, such as a phenomenon in which the transient PL lifetime of the mixed film has more long lifetime components or has a larger proportion of delayed components than that of each of the materials, observed by comparison of transient photoluminescence (PL) of the material having a hole-transport property, the material having an electron-transport property, and the mixed film of the materials. The transient PL can be rephrased as transient electroluminescence (EL). That is, the formation of an exciplex can also be confirmed by a difference in transient response observed by comparison of the transient EL of the material having a hole-transport property, the material having an electron-transport property, and the mixed film of the materials.

An electron-transport layer 114 contains a substance having an electron-transport property. As the substance having an electron-transport property, it is possible to use any of the above-listed substances having electron-transport properties that can be used as the host material.

Note that the electron mobility of the material included in the electron-transport layer 114 in the case where the square root of the electric field strength [V/cm] is 600 is preferably higher than or equal to $1\times10^{-7}$ cm$^2$/Vs and lower than or equal to $5\times10^{-5}$ cm$^2$/Vs. The amount of electrons injected into the light-emitting layer can be controlled by the reduction in the electron-transport property of the electron-transport layer 114, whereby the light-emitting layer can be prevented from having excess electrons. The electron-transport layer 114 preferably includes a material having an electron-transport property and an alkali metal, an alkaline earth metal, a compound thereof, or a complex thereof. It is particularly preferable that these structures be employed when the hole-injection layer is formed using a composite material that includes a material having a hole-transport property with a relatively deep HOMO level of −5.7 eV or higher and −5.4 eV or lower, in which case the light-emitting device can have a long lifetime. In this case, the material having an electron-transport property preferably has a HOMO level of −6.0 eV or higher. The material having an electron-transport property is preferably an organic compound having an anthracene skeleton and further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal, the alkaline earth metal, the compound thereof, or the complex thereof have an 8-hydroxyquinolinato structure. Specific examples include 8-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) of the alkali metal, the alkaline earth metal, the compound thereof, or the complex thereof can also be used. There is preferably a difference in the concentration (including 0) of the alkali metal, the alkaline earth metal, the compound thereof, or the complex thereof in the electron-transport layer in the thickness direction.

A layer containing an alkali metal, an alkaline earth metal, or a compound thereof such as lithium fluoride (LiF), cesium fluoride (CsF), calcium fluoride ($CaF_2$), or 8-hydroxyquinolinatolithium (Liq) may be provided as the electron-injection layer 115 between the electron-transport layer 114 and the second electrode 102. For example, an electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer containing a substance that has an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, a light-emitting device including the layer can have high external quantum efficiency.

Figure 1B:
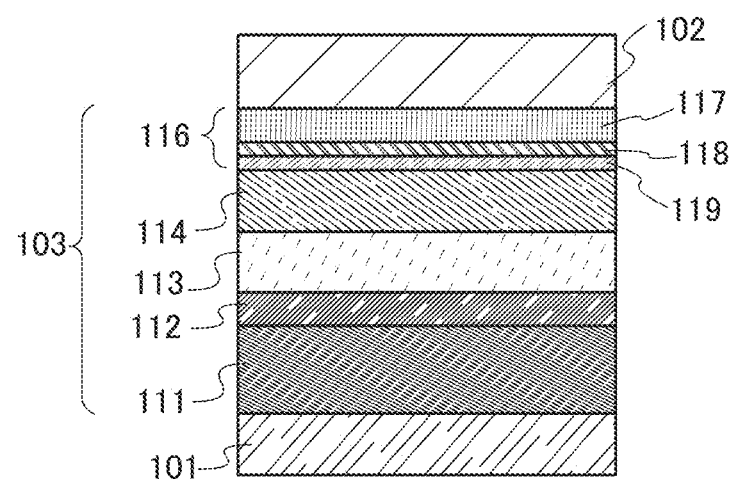

Instead of the electron-injection layer 115, the charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a material having a hole-transport property. When a potential is applied to the p-type layer 117, electrons are injected into the electron-transport layer 114 and holes are injected into the second electrode 102 serving as a cathode; thus, the light-emitting device operates. Since the organic compound of one embodiment of the present invention has a low refractive index, using the organic compound for the p-type layer 117 enables the light-emitting device to have high external quantum efficiency.

Note that the charge-generation layer 116 preferably includes an electron-relay layer 118 and/or an electron-injection buffer layer 119 in addition to the p-type layer 117.

The electron-relay layer 118 includes at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the substance having an acceptor property in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the second electrode 102, a metal, an alloy, an electrically conductive compound, or a mixture thereof each having a low work function (specifically, lower than or equal to 3.8 eV) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys containing these elements (e.g., MgAg and AlLi) and alkali metals such as europium (Eu) and ytterbium (Yb), and alloys containing these rare earth metals. However, when the electron-injection layer is provided between the second electrode 102 and the electron-transport layer, for the second electrode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be used.

Different methods may be used to form the electrodes or the layers described above.

The structure of the layers provided between the first electrode 101 and the second electrode 102 is not limited to the above-described structure. Preferably, a light-emitting region where holes and electrons recombine is positioned away from the first electrode 101 and the second electrode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of a light-emitting device with a structure in which a plurality of light-emitting units are stacked (this type of light-emitting device is also referred to as a stacked or tandem light-emitting device) is described with reference to FIG. 1C. This light-emitting device includes a plurality of light-emitting units between an anode and a cathode. One light-emitting unit has substantially the same structure as the EL layer 103 illustrated in FIG. 1A. In other words, the light-emitting device illustrated in FIG. 1A or 1B includes a single light-emitting unit, and the light-emitting device illustrated in FIG. 1C includes a plurality of light-emitting units.

Figure 1C:
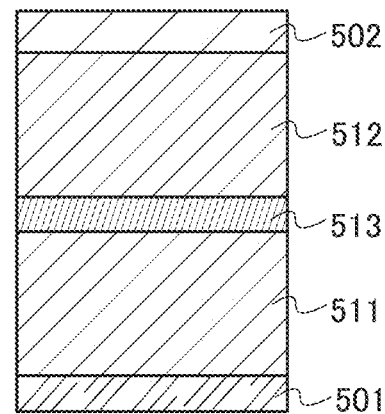

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 1C, the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The light-emitting device having two light-emitting units is described with reference to FIG. 1C; however, one embodiment of the present invention can also be applied to a light-emitting device in which three or more light-emitting units are stacked. With a plurality of light-emitting units partitioned by the charge-generation layer 513 between a pair of electrodes as in the light-emitting device of this embodiment, it is possible to provide a long-life device which can emit light with high luminance at a low current density. A light-emitting apparatus which can be driven at a low voltage and has low power consumption can be provided.

When the emission colors of the light-emitting units are different, light emission of a desired color can be obtained from the light-emitting device as a whole. For example, in a light-emitting device having two light-emitting units, the emission colors of the first light-emitting unit may be red and green and the emission color of the second light-emitting unit may be blue, so that the light-emitting device can emit white light as the whole.

The above-described layers and electrodes such as the EL layer 103, the first light-emitting unit 511, the second light-emitting unit 512, and the charge-generation layer 513 can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus including the light-emitting device described in Embodiment 2 is described.

In this embodiment, the light-emitting apparatus fabricated using the light-emitting device described in Embodiment 2 is described with reference to FIGS. 2A and 2B. Note that FIG. 2A is a top view of the light-emitting apparatus and FIG. 2B is a cross-sectional view taken along the lines A-B and C-D in FIG. 2A. This light-emitting apparatus includes a driver circuit portion (source line driver circuit) 601, a pixel portion 602, and a driver circuit portion (gate line driver circuit) 603, which are to control light emission of a light-emitting device and illustrated with dotted lines. Reference numeral 604 denotes a sealing substrate; 605, a sealing material; and 607, a space surrounded by the sealing material 605.

A lead wiring 608 is a wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting apparatus in the present specification includes, in its category, not only the light-emitting apparatus itself but also the light-emitting apparatus provided with the FPC or the PWB.

Next, a cross-sectional structure is described with reference to FIG. 2B. The driver circuit portions and the pixel portion are formed over an element substrate 610; here, the source line driver circuit 601, which is a driver circuit portion, and one pixel in the pixel portion 602 are illustrated.

The element substrate 610 may be a substrate containing glass, quartz, an organic resin, a metal, an alloy, or a semiconductor or a plastic substrate formed of fiber reinforced plastic (FRP), poly(vinyl fluoride) (PVF), polyester, or acrylic resin.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic device with extremely low power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that to cover an end portion of the first electrode 613, an insulator 614 is formed, for which a positive photosensitive acrylic resin film is used here.

In order to improve coverage with an EL layer or the like which is formed later, the insulator 614 is formed to have a curved surface with curvature at its upper or lower end portion. For example, in the case where positive photosensitive acrylic resin is used as a material of the insulator 614, only the upper end portion of the insulator 614 preferably has a curved surface with a curvature radius (0.2 m to 3 m). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting device is formed with the first electrode 613, the EL layer 616, and the second electrode 617. The light-emitting device is the light-emitting device described in Embodiment 2. In the light-emitting apparatus of this embodiment, the pixel portion, which includes a plurality of light-emitting devices, may include both the light-emitting device described in Embodiment 2 and a light-emitting device having a different structure.

The sealing substrate 604 is attached to the element substrate 610 with the sealing material 605, so that a light-emitting device 618 is provided in a space 607 surrounded by the element substrate 610, the sealing substrate 604, and the sealing material 605. The space 607 may be filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastic (FRP), poly(vinyl fluoride) (PVF), polyester, and acrylic resin can be used.

Although not illustrated in FIGS. 2A and 2B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting apparatus fabricated using the light-emitting device described in Embodiment 2 can be obtained.

The light-emitting apparatus in this embodiment is fabricated using the light-emitting device described in Embodiment 2 and thus can have favorable characteristics. Specifically, since the light-emitting device described in Embodiment 2 has high emission efficiency, the light-emitting apparatus can achieve low power consumption.

FIGS. 3A and 3B each illustrate an example of a light-emitting apparatus that includes a light-emitting device exhibiting white light emission and coloring layers (color filters) and the like to display a full-color image. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition 1025, an EL layer 1028, a second electrode 1029 of the light-emitting devices, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, green, or blue, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
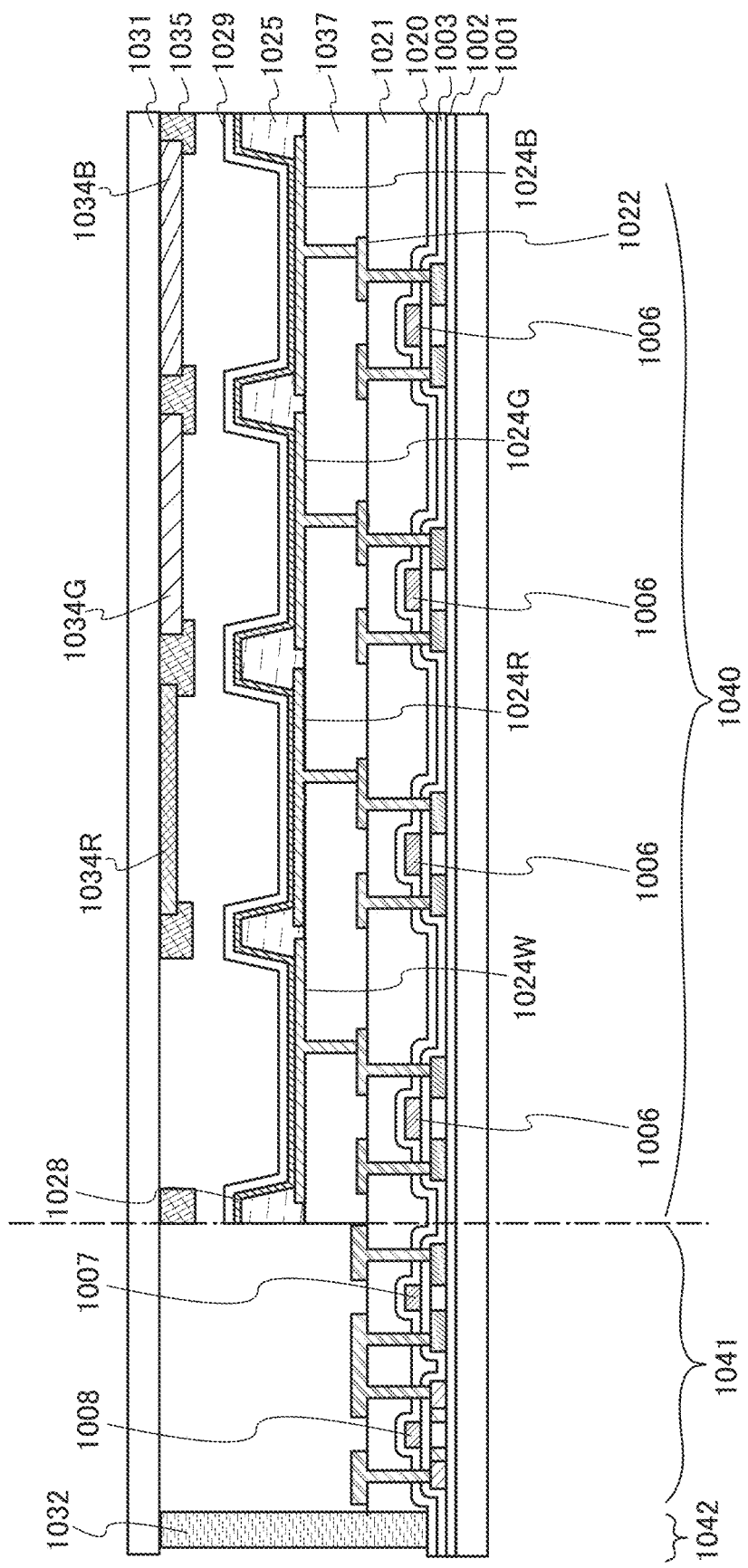
FIG. 4 is a conceptual view of an active matrix light-emitting apparatus.

The above-described light-emitting apparatus has a structure in which light is extracted from the substrate 1001 side where FETs are formed (a bottom emission structure), but may have a structure in which light is extracted from the sealing substrate 1031 side (atop emission structure). FIG. 4 is across-sectional view of a light-emitting apparatus having a top emission structure. In this case, a substrate which does not transmit light can be used as the substrate 1001. The process up to the step of forming a connection electrode which connects the FET and the anode of the light-emitting device is performed in a manner similar to that of the light-emitting apparatus having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting devices each serve as an anode here, but may serve as a cathode. Furthermore, in the case of a light-emitting apparatus having a top emission structure as illustrated in FIG. 4, the first electrodes are preferably reflective electrodes. The EL layer 1028 is formed to have a structure similar to the structure of the EL layer 103, which is described in Embodiment 2, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix 1035 may be covered with the overcoat layer 1036. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting apparatus having a top emission structure, a microcavity structure can be favorably employed. A light-emitting device with a microcavity structure is formed with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode has a visible light reflectivity of 40% to 100%, preferably 70% to 100%, and a resistivity of $1\times10^{-2}$ Ωcm or lower. In addition, the semi-transmissive and semi-reflective electrode has a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of color to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting device described above may be combined with a plurality of EL layers; for example, a light-emitting device may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because the luminance can be increased owing to yellow light emission and each subpixel can employ a microcavity structure suitable for wavelengths of the corresponding color.

The light-emitting apparatus in this embodiment is fabricated using the light-emitting device described in Embodiment 2 and thus can have favorable characteristics. Specifically, since the light-emitting device described in Embodiment 2 has high emission efficiency, the light-emitting apparatus can achieve low power consumption.

Figure 5A:
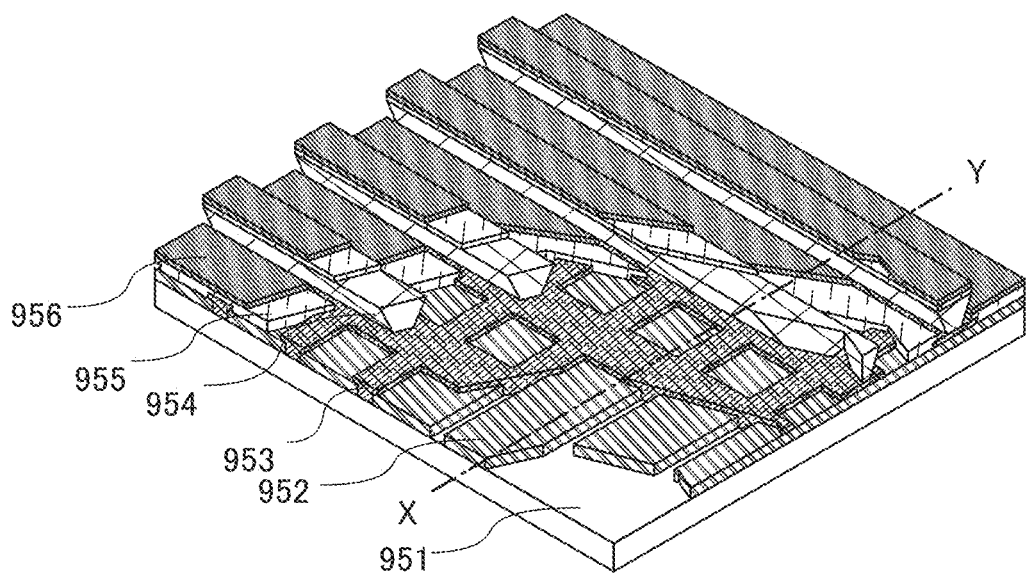
FIGS. 5A and 5B are conceptual views of a passive matrix light-emitting apparatus.
Figure 5B:
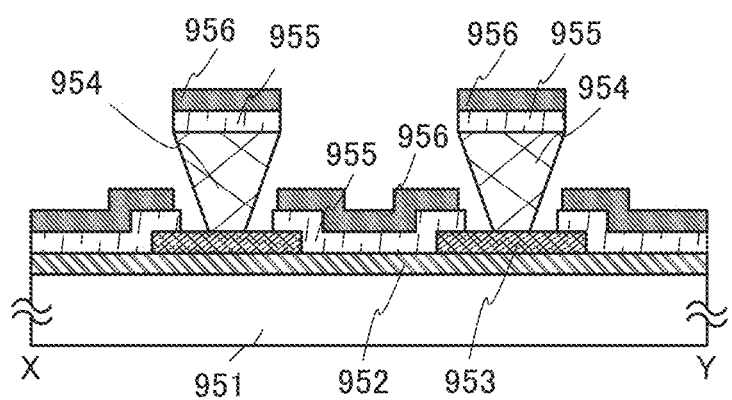

An active matrix light-emitting apparatus is described above, whereas a passive matrix light-emitting apparatus is described below. FIGS. 5A and 5B illustrate a passive matrix light-emitting apparatus fabricated using the present invention. Note that FIG. 5A is a perspective view of the light-emitting apparatus, and FIG. 5B is a cross-sectional view taken along the line X-Y in FIG. 5A. In FIGS. 5A and 5B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid which is parallel to the surface of the insulating layer 953 and is in contact with the insulating layer 953) is shorter than the upper side (a side of the trapezoid which is parallel to the surface of the insulating layer 953 and is not in contact with the insulating layer 953). The partition layer 954 thus provided can prevent defects in the light-emitting device due to static electricity or others. The passive-matrix light-emitting apparatus also includes the light-emitting device described in Embodiment 2; thus, the light-emitting apparatus can have high reliability or low power consumption.

Since many minute light-emitting devices arranged in a matrix in the light-emitting apparatus described above can each be controlled, the light-emitting apparatus can be suitably used as a display device for displaying images.

This embodiment can be freely combined with any of the other embodiments.

Embodiment 4

Figure 6A:
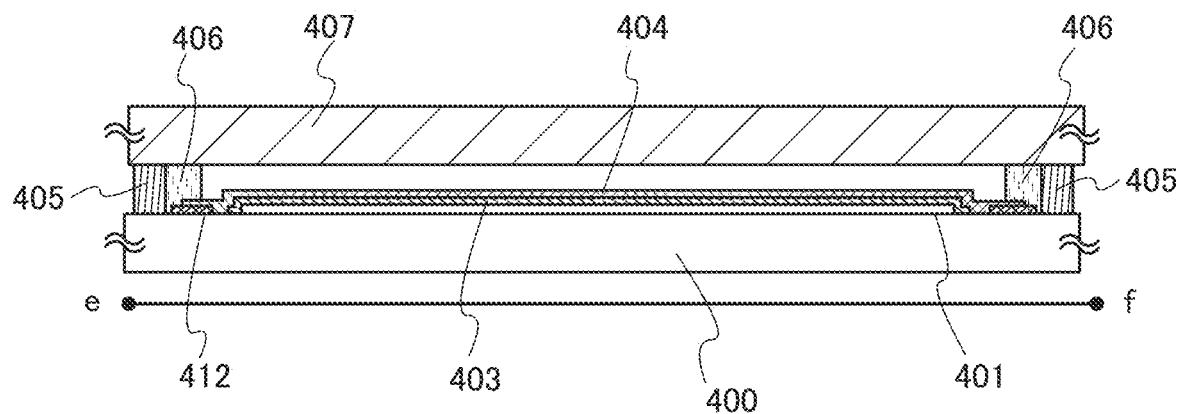
FIGS. 6A and 6B illustrate a lighting device.
Figure 6B:
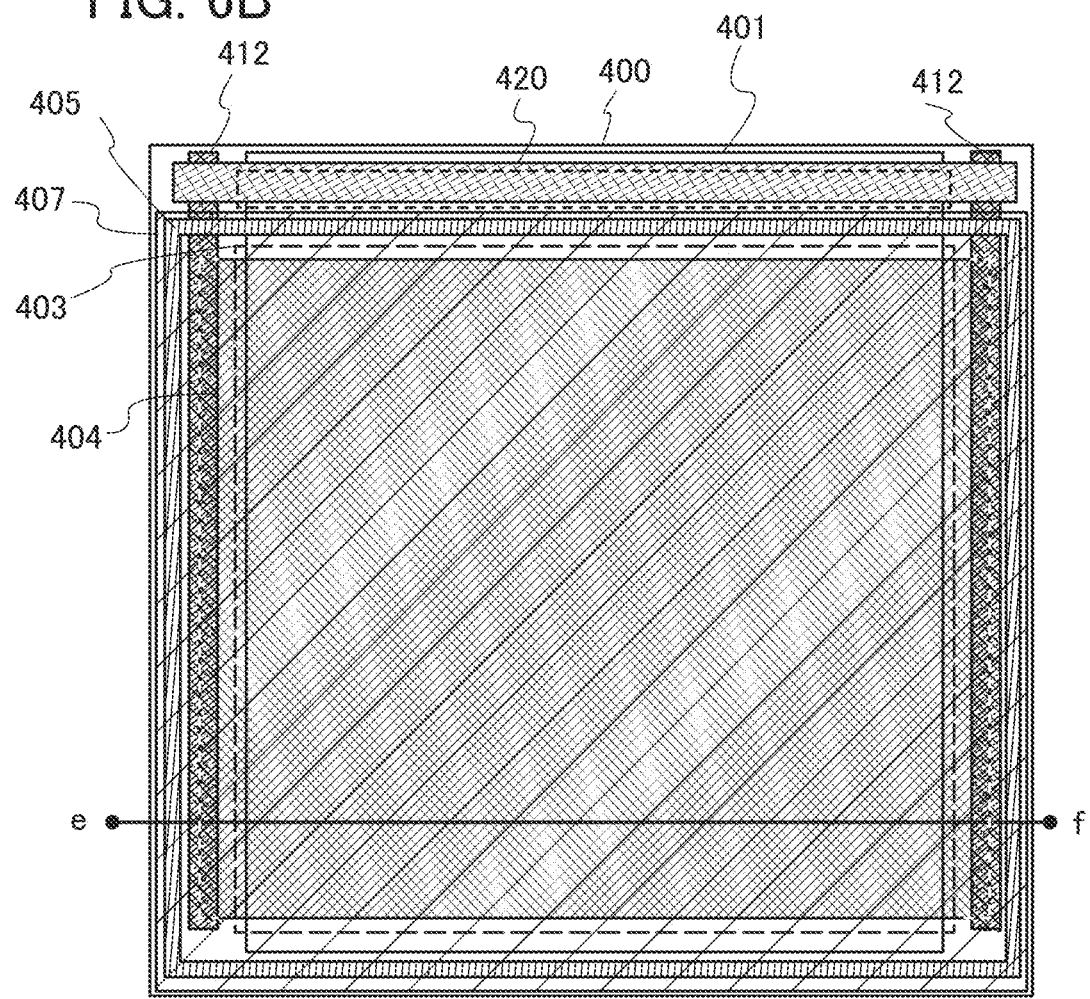

In this embodiment, an example in which the light-emitting device described in Embodiment 2 is used for a lighting device will be described with reference to FIGS. 6A and 6B. FIG. 6B is a top view of the lighting device, and FIG. 6A is a cross-sectional view taken along the line e-f in FIG. 6B.

In the lighting device in this embodiment, a first electrode 401 is formed over a substrate 400 which is a support and has a light-transmitting property. The first electrode 401 corresponds to the first electrode 101 in Embodiment 2. When light is extracted from the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiment 2, or the structure in which the light-emitting units 511 and 512 and the charge-generation layer 513 are combined. Refer to the descriptions for the structure.

The second electrode 404 is formed to cover the EL layer 403. The second electrode 404 corresponds to the second electrode 102 in Embodiment 2. The second electrode 404 is formed using a material having high reflectance when light is extracted from the first electrode 401 side. The second electrode 404 is connected to the pad 412, whereby voltage is applied.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device having low power consumption.

The substrate 400 provided with the light-emitting device having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 6B) can be mixed with a desiccant which enables moisture to be adsorbed, increasing reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting device described in Embodiment 2; thus, the lighting device can consume less power.

Embodiment 5

In this embodiment, examples of electronic devices each including the light-emitting device described in Embodiment 2 will be described. The light-emitting device described in Embodiment 2 has high emission efficiency and low power consumption. As a result, the electronic devices described in this embodiment can each include a light-emitting portion having low power consumption.

Examples of the electronic device including the above light-emitting device include television devices (also referred to as TV or television receivers), monitors for computers and the like, digital cameras, digital video cameras, digital photo frames, cellular phones (also referred to as mobile phones or mobile phone devices), portable game machines, portable information terminals, audio playback devices, and large game machines such as pachinko machines. Specific examples of these electronic devices are shown below.

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting devices described in Embodiment 2 are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 7B1 illustrates a computer, which includes a main body 7201, a housing 7202, a display portion 7203, a keyboard 7204, an external connection port 7205, a pointing device 7206, and the like. Note that this computer is fabricated using the light-emitting devices that are described in Embodiment 2 and arranged in a matrix in the display portion 7203. The computer illustrated in FIG. 7B1 may have a structure illustrated in FIG. 7B2. A computer illustrated in FIG. 7B2 is provided with a second display portion 7210 instead of the keyboard 7204 and the pointing device 7206. The second display portion 7210 is a touch panel, and input operation can be performed by touching display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

FIG. 7C illustrates an example of a portable terminal. A cellular phone is provided with a display portion 7402 incorporated in a housing 7401, operation buttons 7403, an external connection port 7404, a speaker 7405, a microphone 7406, and the like. Note that the cellular phone has the display portion 7402 including the light-emitting devices described in Embodiment 2 and arranged in a matrix.

When the display portion 7402 of the portable terminal illustrated in FIG. 7C is touched with a finger or the like, data can be input into the portable terminal. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting information such as text. The third mode is a display-and-input mode in which the two modes, the display mode and the input mode, are combined.

For example, in the case of making a call or creating an e-mail, a text input mode mainly for inputting text is selected for the display portion 7402 so that text displayed on the screen can be input. In this case, it is preferable to display a keyboard or number buttons on almost the entire screen of the display portion 7402.

When a sensing device including a sensor such as a gyroscope or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by providing a backlight or a sensing light source which emits near-infrared light in the display portion, an image of a finger vein, a palm vein, or the like can be taken.

Figure 8A:
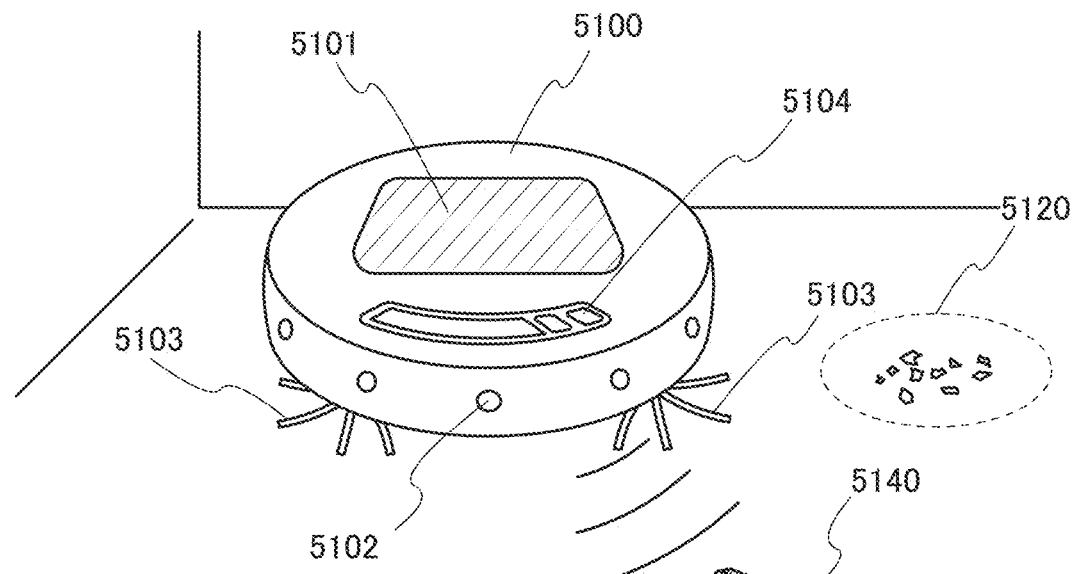
FIGS. 8A to 8C illustrate electronic devices.

FIG. 8A is a schematic view illustrating an example of a cleaning robot.

A cleaning robot 5100 includes a display 5101 on its top surface, a plurality of cameras 5102 on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. The cleaning robot 5100 has a wireless communication means.

The cleaning robot 5100 is self-propelled, detects dust 5120, and sucks up the dust through the inlet provided on the bottom surface.

The cleaning robot 5100 can determine whether there is an obstacle such as a wall, furniture, or a step by analyzing images taken by the cameras 5102. When the cleaning robot 5100 detects an object that is likely to be caught in the brush 5103 (e.g., a wire) by image analysis, the rotation of the brush 5103 can be stopped.

The display 5101 can display the remaining capacity of a battery, the amount of collected dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor his/her room even when the owner is not at home. The owner can also check the display on the display 5101 by the portable electronic device 5140 such as a smartphone.

The light-emitting apparatus of one embodiment of the present invention can be used for the display 5101.

Figure 8B:
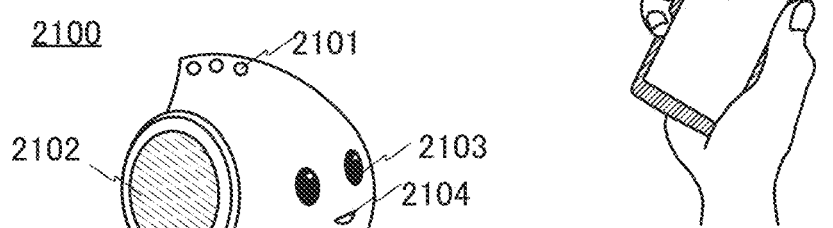

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
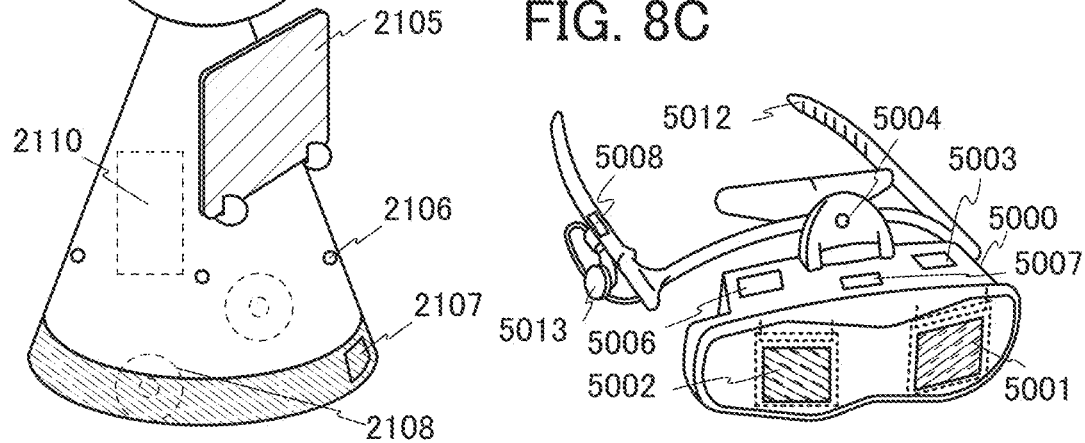

FIG. 8C illustrates an example of a goggles-type display. The goggles-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 9:
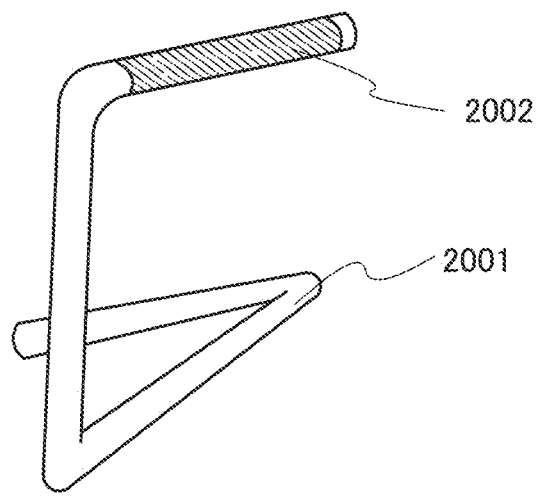
FIG. 9 illustrates a lighting device.

FIG. 9 illustrates an example in which the light-emitting device described in Embodiment 2 is used for a table lamp which is a lighting device. The table lamp illustrated in FIG.

9 includes a housing 2001 and a light source 2002, and the lighting device described in Embodiment 3 may be used for the light source 2002.

Figure 10:
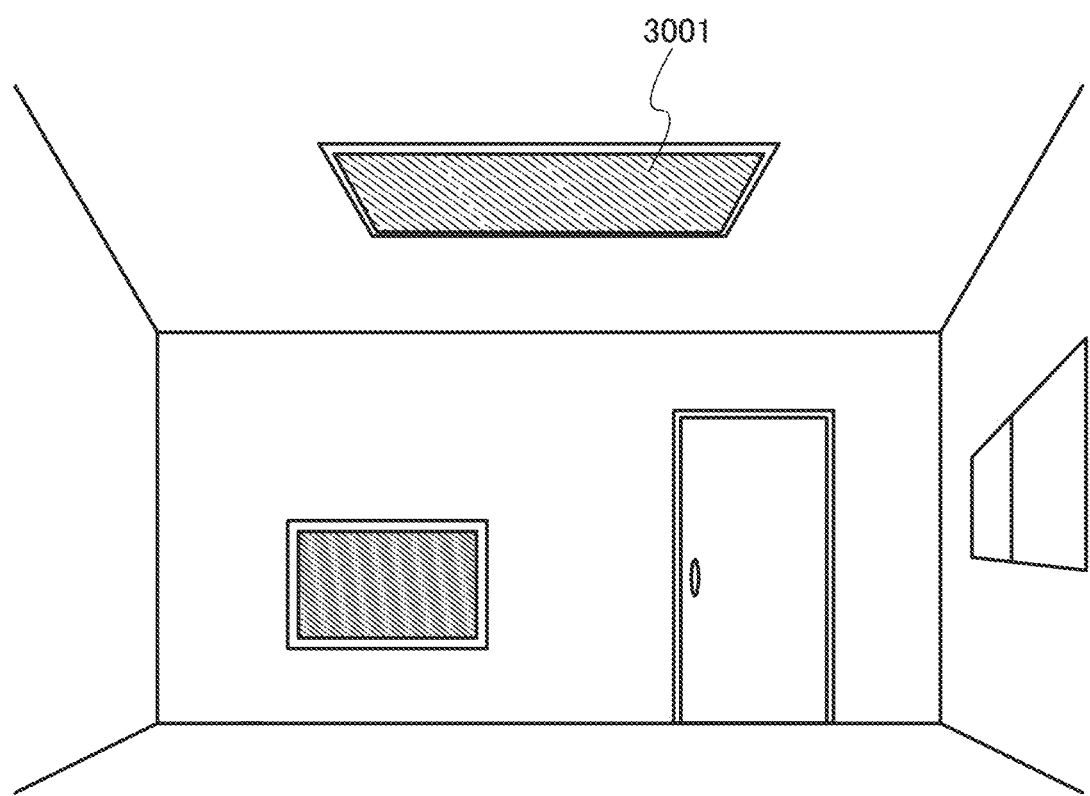
FIG. 10 illustrates alighting device.

FIG. 10 illustrates an example in which the light-emitting device described in Embodiment 2 is used for an indoor lighting device 3001. Since the light-emitting device described in Embodiment 2 has high emission efficiency, the lighting device can have low power consumption. Furthermore, since the light-emitting device described in Embodiment 2 can have a large area, the light-emitting device can be used for a large-area lighting device. Furthermore, since the light-emitting device described in Embodiment 2 is thin, the light-emitting device can be used for a lighting device having a reduced thickness.

Figure 11:
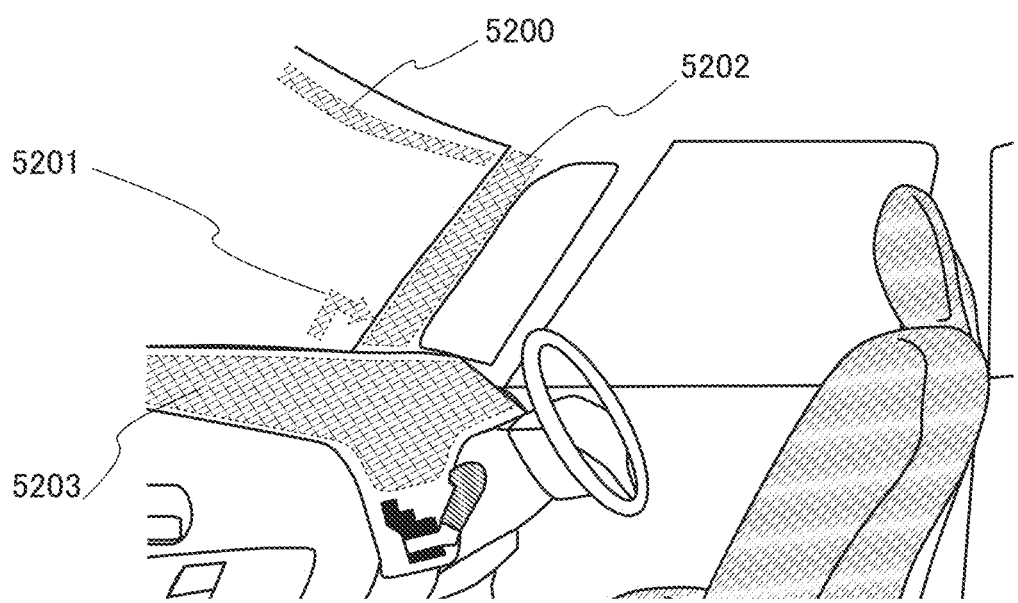
FIG. 11 illustrates in-vehicle display apparatuses and lighting devices.

The light-emitting device described in Embodiment 2 can also be used for an automobile windshield or an automobile dashboard. FIG. 11 illustrates one mode in which the light-emitting devices described in Embodiment 2 are used for an automobile windshield and an automobile dashboard. Display regions 5200 to 5203 each include the light-emitting device described in Embodiment 2.

The display regions 5200 and 5201 are display devices which are provided in the automobile windshield and in which light-emitting devices each of which is described in Embodiment 2 are incorporated. The light-emitting devices described in Embodiment 2 can be formed into what is called a see-through display device, through which the opposite side can be seen, by including a first electrode and a second electrode formed of electrodes having a light-transmitting property. Such see-through display devices can be provided even in the automobile windshield without hindering the view. In the case where a driving transistor or the like is provided, a transistor having a light-transmitting property, such as an organic transistor including an organic semiconductor material or a transistor including an oxide semiconductor, is preferably used.

A display device incorporating the light-emitting device described in Embodiment 2 is provided in the display region 5202 in a pillar portion. The display region 5202 can compensate for the view hindered by the pillar by displaying an image taken by an imaging unit provided in the car body. Similarly, the display region 5203 provided in the dashboard portion can compensate for the view hindered by the car body by displaying an image taken by an imaging unit provided on the outside of the automobile. Thus, blind areas can be eliminated to enhance the safety. Images that compensate for the areas which a driver cannot see enable the driver to ensure safety easily and comfortably.

The display region 5203 can provide a variety of kinds of information such as navigation data, speed, and the number of revolution. The content or layout of the display can be changed freely by a user as appropriate. Note that such information can also be displayed on the display regions 5200 to 5202. The display regions 5200 to 5203 can also be used as lighting devices.

Figure 12A:
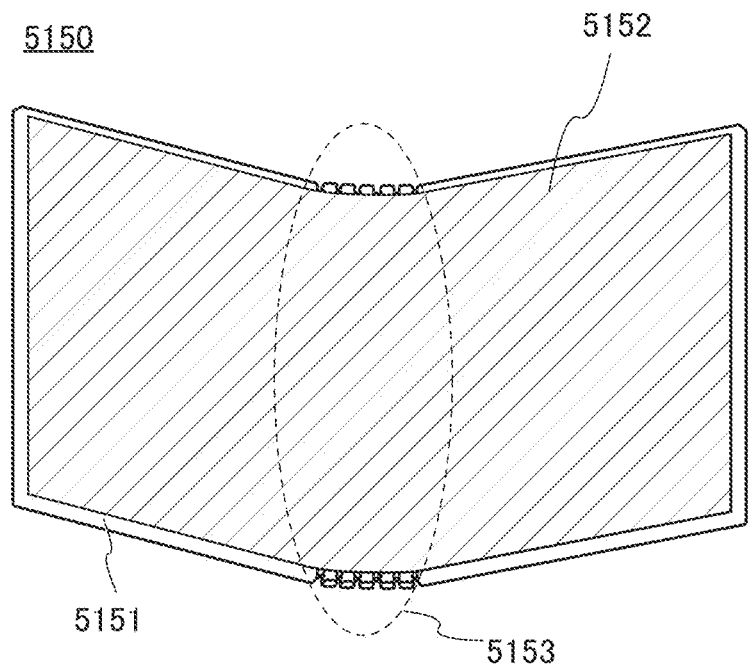
FIGS. 12A and 12B illustrate an electronic device.
Figure 12B:
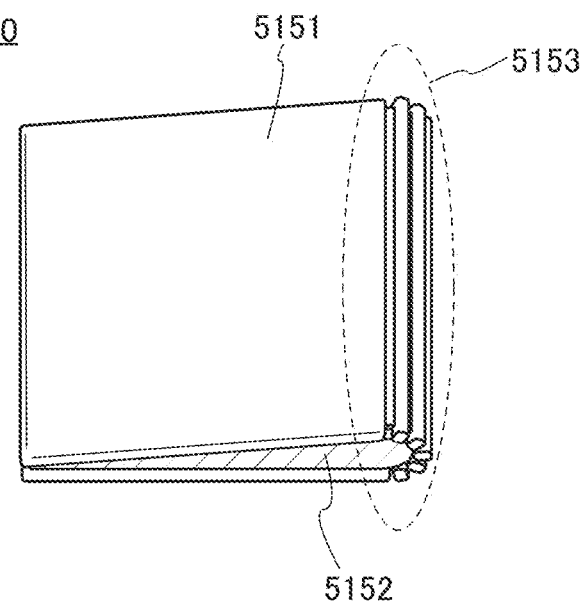

FIGS. 12A and 12B illustrate a foldable portable information terminal 5150. The foldable portable information terminal 5150 includes a housing 5151, a display region 5152, and a bend portion 5153. FIG. 12A illustrates the portable information terminal 5150 that is opened. FIG. 12B illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 includes a flexible member and a plurality of supporting members. When the display region is folded, the flexible member expands and the bend portion 5153 has a radius of curvature of greater than or equal to 2 mm, preferably greater than or equal to 3 mm.

Note that the display region 5152 may be a touch panel (an input/output device) including a touch sensor (an input device). The light-emitting apparatus of one embodiment of the present invention can be used for the display region 5152.

Figure 13A:
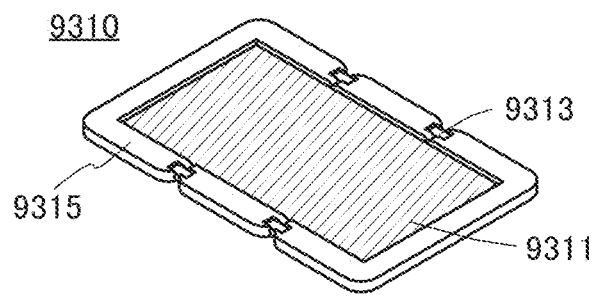
FIGS. 13A to 13C illustrate an electronic device.
Figure 13B:
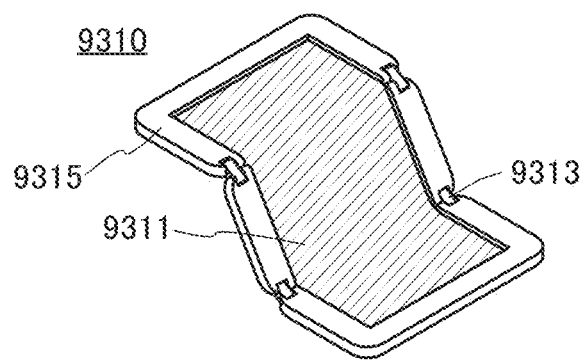
Figure 13C:
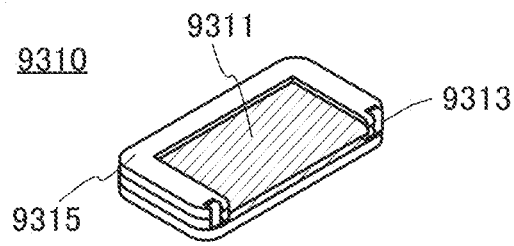

FIGS. 13A to 13C illustrate a foldable portable information terminal 9310. FIG. 13A illustrates the portable information terminal 9310 that is opened. FIG. 13B illustrates the portable information terminal 9310 that is being opened or being folded. FIG. 13C illustrates the portable information terminal 9310 that is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus of one embodiment of the present invention can be used for the display panel 9311.

Note that the structure described in this embodiment can be combined with any of the structures described in Embodiments 1 to 4 as appropriate.

As described above, the application range of the light-emitting apparatus including the light-emitting device described in Embodiment 2 is wide, and thus the light-emitting apparatus can be applied to electronic devices in a variety of fields. By using the light-emitting device described in Embodiment 2, an electronic device with low power consumption can be obtained.

Example 1

Synthesis Example 1

In this example, a method for synthesizing N,N'-Bis[9-(4-tert-butylphenyl)-9H-carbazol-2-yl]-N,N'-diphenyl-naphtho[2,3-b;6,7-b']bisbenzofuran-3,10-diamine (abbreviation: 3,10tBuPCA2Nbf(IV)-02) represented by Structural Formula (136) in Embodiment 1 will be described. The structural formula of 3,10tBuPCA2Nbf(IV)-02 is shown below.

[Chemical Formula 36]

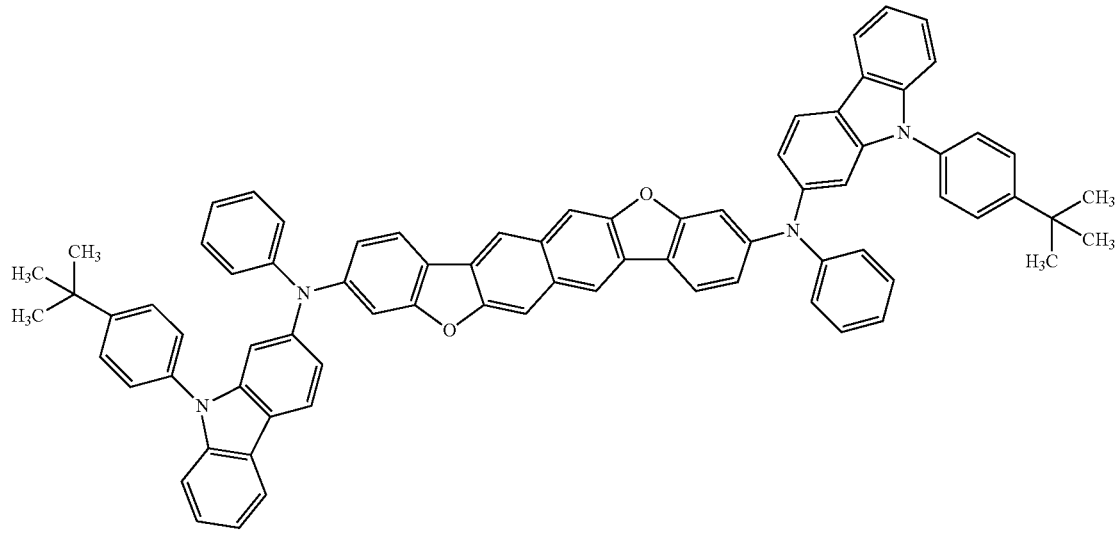

3,10tBuPCA2Nbf(IV)-02

Step 1: Synthesis of 2-chloro-9-(4-tert-butylphenyl)-9H-carbazole

Into a 300-mL three-neck flask were put 5.3 g (27 mmol) of 2-chloro-9H-carbazole, 10 g (48 mmol) of 1-bromo-4-tert-butylbenzene, and 7.7 g (80 mmol) of sodium tert-butoxide. To the mixture were added 130 mL of xylene and 0.4 mL of tri(tert-butyl)phosphine (a 10% hexane solution), and the mixture was degassed by being stirred while the pressure was reduced. Then, 0.15 g (0.27 mmol) of bis(dibenzylideneacetone)palladium(0) was added to the mixture, and the mixture was stirred while being heated at 150° C. under a nitrogen stream for 13 hours. After the stirring, toluene was added to the mixture, and the mixture was suction-filtered through Florisil, Celite, and alumina to give a filtrate. The obtained filtrate was concentrated to give a solid. The solid was purified by silica gel column chromatography (as the developing solvent, hexane was used) to give a solid. Ethanol was added to the obtained solid, and the mixture was irradiated with ultrasonic waves and then filtered, whereby 7.5 g of a white solid was obtained in a yield of 85%. The synthesis scheme of Step 1 is shown below.

[Chemical Formula 37]

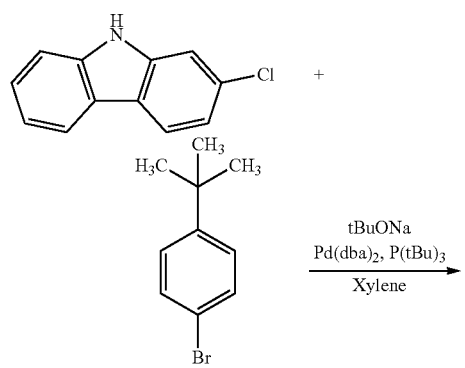

-continued

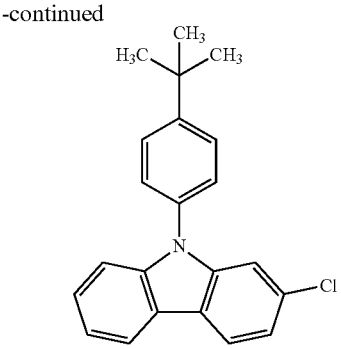

Measurement results obtained by nuclear magnetic resonance (¹H-NMR) spectroscopy of the white solid obtained in Step 1 are shown below. The results revealed that 2-chloro-9-(4-tert-butylphenyl)-9H-carbazole was obtained in Step 1.

¹H-NMR (CD$_2$Cl$_2$, 300 MHz): δ=1.43 (s, 9H), 7.22-7.31 (m, 2H), 7.36-7.48 (m, 5H), 7.62-7.67 (m, 2H), 8.06 (d, J1=8.4 Hz, 1H), 8.11 (dt, J1=7.8 Hz, J2=1.2 Hz, 1H).

Step 2: Synthesis of N-phenyl-9-(4-tert-butylphenyl)-9H-carbazol-2-amine

Into a 200-mL three-neck flask were put 5.0 g (15 mmol) of 2-chloro-9-(4-tert-butylphenyl)-9H-carbazole, 2.1 g (23 mmol) of aniline, 4.3 g (45 mmol) of sodium tert-butoxide, and 0.27 g (0.75 mmol) of di(1-adamantyl)-n-butylphosphine. To the mixture was added 100 mL of xylene, and the mixture was degassed by being stirred while the pressure was reduced. To the mixture was added 86 mg (0.15 mmol) of bis(dibenzylideneacetone)palladium(0), and the mixture was stirred while being heated at 150° C. under a nitrogen stream for 6.5 hours. After the stirring, toluene was added to the mixture, the mixture was suction-filtered through Florisil, Celite, and alumina, and the filtrate was concentrated to give a solid. The solid was purified by silica gel column chromatography (as the developing solvent, toluene and hexane in a ratio of 1:2 were used). The solid failed to be purified was purified by silica gel column chromatography (as the developing solvent, toluene and hexane in a ratio of 1:3 were used, and then toluene and hexane in a ratio of 3:7 were used). As a result, 4.0 g of a white solid was obtained in a yield of 68%. The synthesis scheme of Step 2 is shown below.

[Chemical Formula 38]

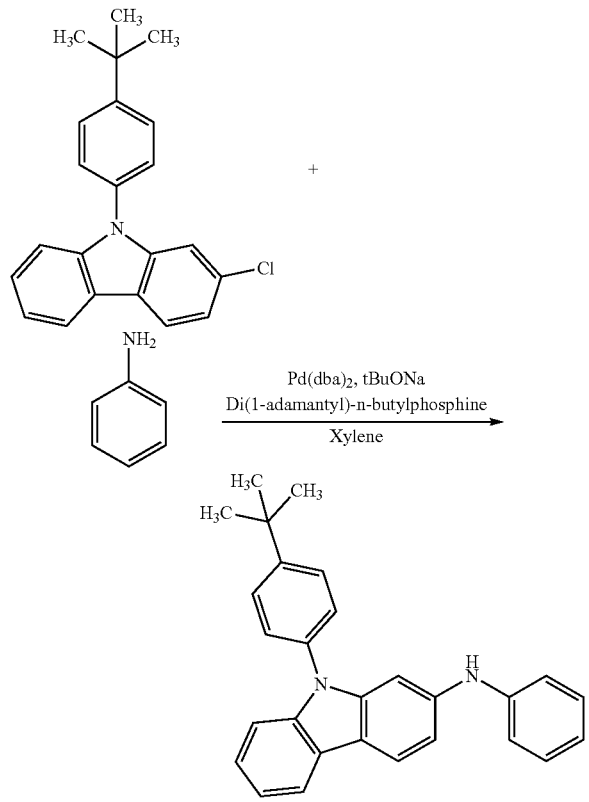

Measurement results obtained by nuclear magnetic resonance (H-NMR) spectroscopy of the white solid obtained in Step 2 are shown below. The results revealed that N-phenyl-9-(4-tert-butylphenyl)-9H-carbazol-2-amine was obtained in Step 2.

$^1$H-NMR (DMSO-$d_6$, 300 MHz): δ=1.38 (s, 9H), 6.81 (t, J1=7.2 Hz, 1H), 7.01-7.11 (m, 4H), 7.18-7.30 (m, 5H), 7.54 (d, J1=8.4 Hz, 2H), 7.68 (d, J1=8.7 Hz, 2H), 8.03-8.08 (m, 2H), 8.36 (s, 1H).

Step 3: Synthesis of 3,10tBuPCA2Nbf(IV)-02

Into a 200-mL three-neck flask were put 0.86 g (2.3 mmol) of 3,10-dichloronaphtho[2,3-b;6,7-b']bisbenzofuran, 2.2 g (5.5 mmol) of N-phenyl-9-(4-tert-butylphenyl)-9H-carbazol-2-amine, 82 mg (0.23 mmol) of di(1-adamantyl)-n-butylphosphine, and 1.3 g (14 mmol) of sodium tert-butoxide. To the mixture was added 25 mL of xylene. The mixture was degassed by being stirred while the pressure was reduced. To the mixture was added 26 mg (46 mol) of bis(dibenzylideneacetone)palladium(0), and the mixture was stirred while being heated at 150° C. under a nitrogen stream for 8 hours. After the stirring, the mixture was filtered to collect a solid. The obtained solid was washed with ethanol and water. The washed solid was purified by silica gel column chromatography (as the developing solvent, toluene was used) to give a solid. The obtained solid was recrystallized with toluene twice, whereby 1.5 g of a yellow solid was obtained in a yield of 59%. Then, 1.1 g of the obtained solid was purified by a train sublimation method under a pressure of $2.7 \times 10^{-2}$ Pa, an argon flow rate of 0 mL/min, and a temperature of 380° C. After the purification by sublimation, 0.40 g of a yellow solid was obtained at a collection rate of 38%. The synthesis scheme of Step 3 is shown below.

[Chemical Formula 39]

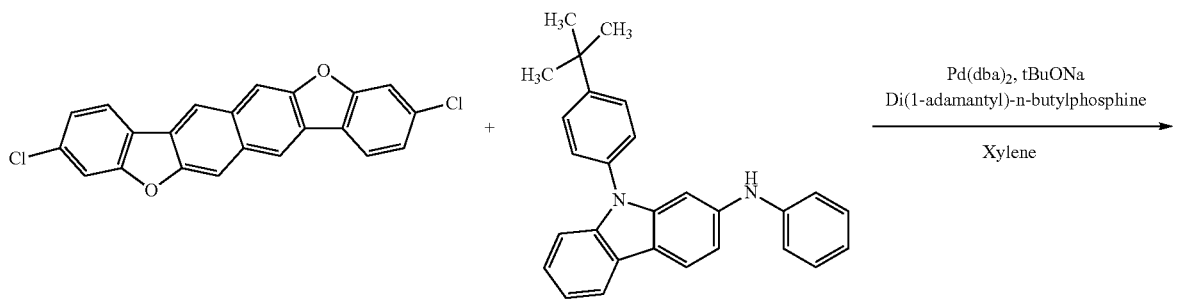

-continued

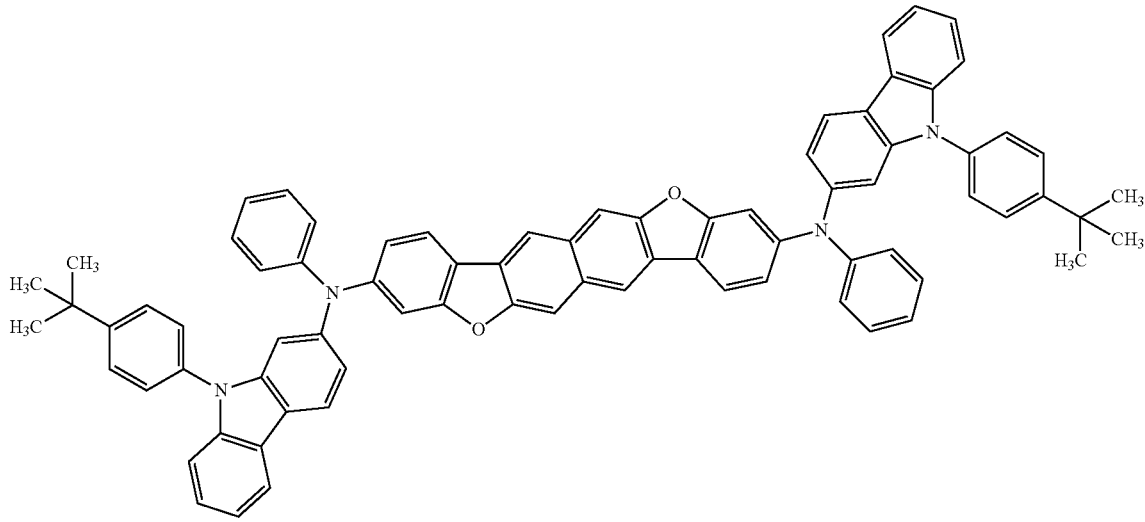

Figure 14A:
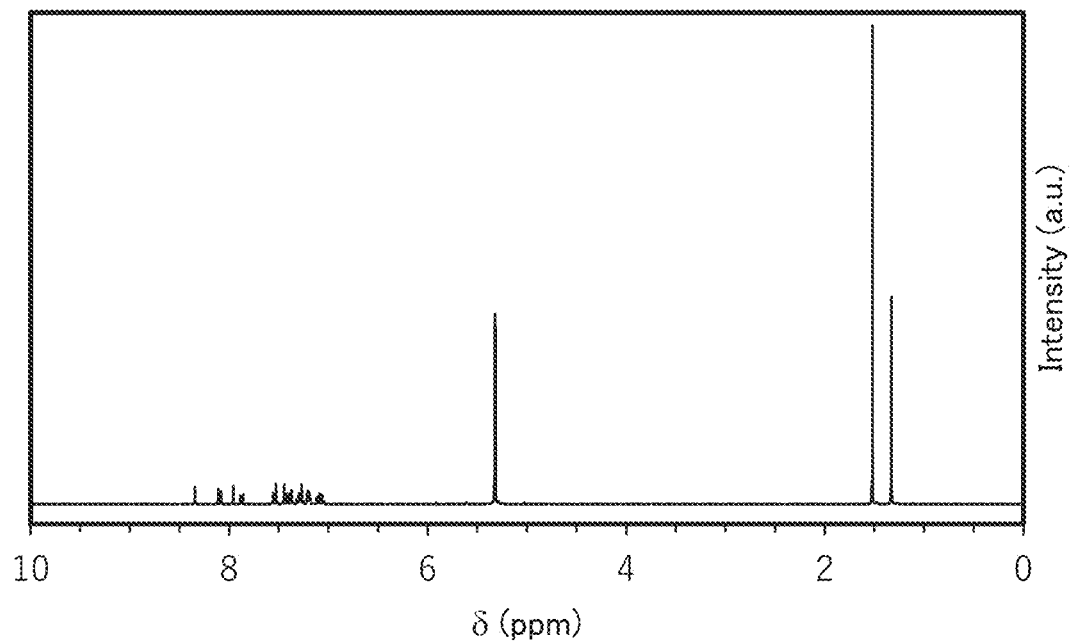
FIGS. 14A and 14B are $^1$H-NMR charts of 3,10tBuPCA2Nbf(IV)-02.
Figure 14B:
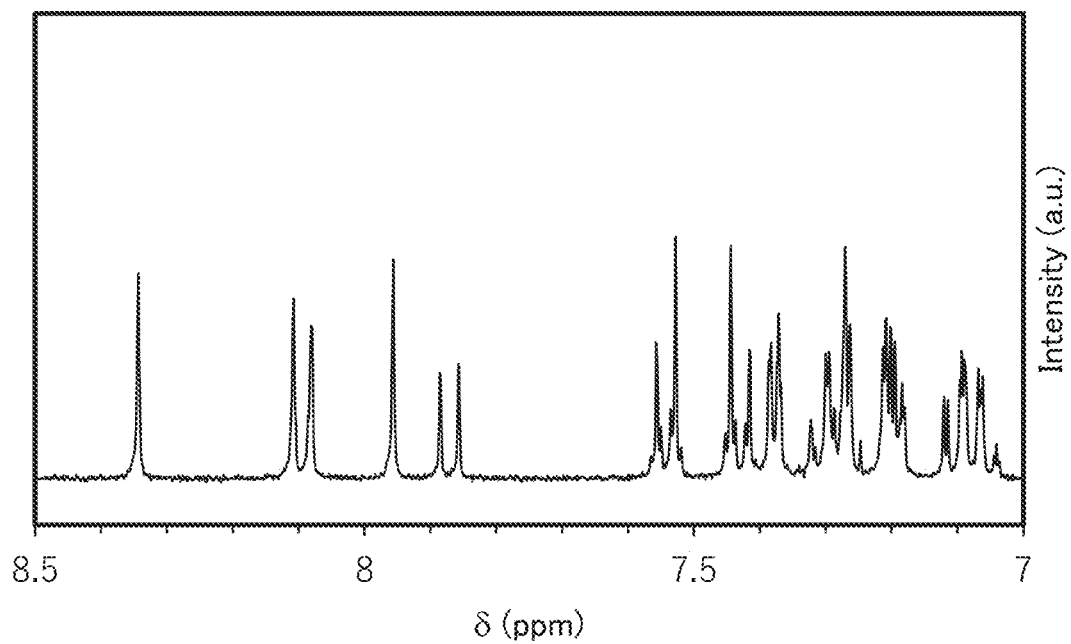

FIGS. 14A and 14B show measurement results obtained by nuclear magnetic resonance ($^1$H-NMR) spectroscopy of the yellow solid obtained in Step 3, whose numerical data is shown below. The results revealed that 3,10tBuPCA2Nbf (IV)-02 was obtained in Step 3.

$^1$H-NMR (CD$_2$Cl$_2$, 300 MHz): δ=1.33 (s, 18H), 7.03-7.12 (m, 6H), 7.18-7.21 (m, 6H), 7.25-7.32 (m, 8H), 7.37-7.57 (m, 12H), 7.87 (d, J1=8.4 Hz, 2H), 7.96 (s, 2H), 8.09 (d, J1=8.1 Hz, 4H), 8.34 (s, 2H).

Figure 15:
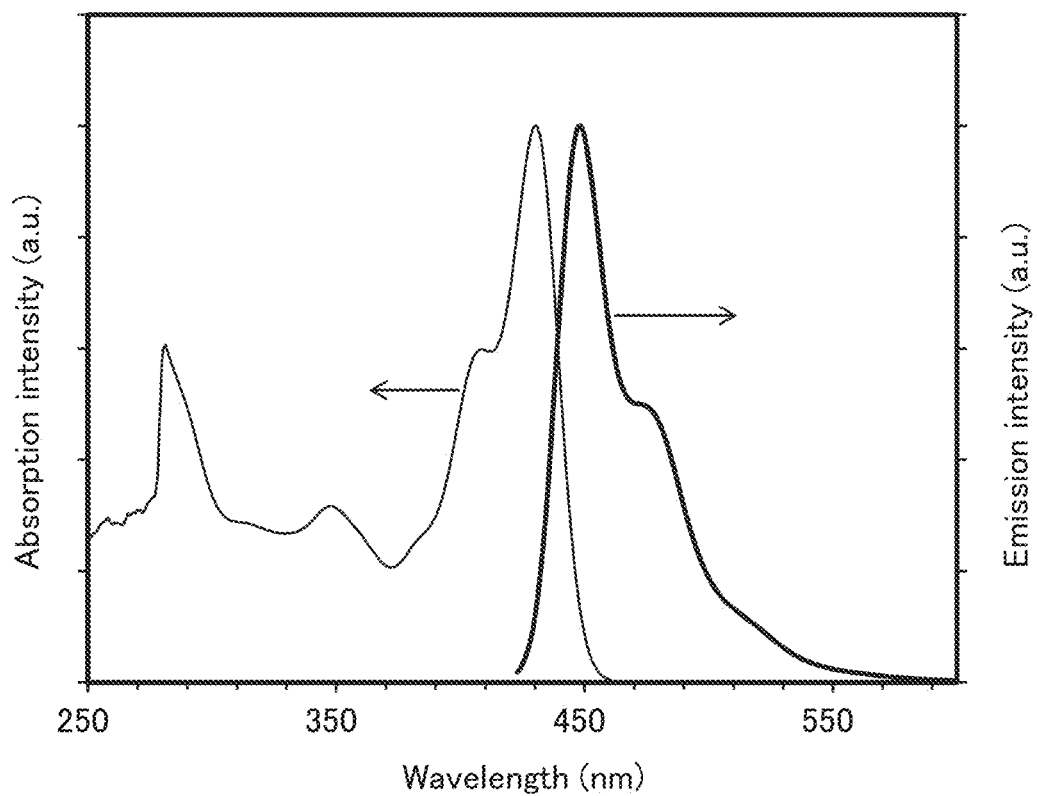
FIG. 15 shows an absorption spectrum and an emission spectrum of 3,10tBuPCA2Nbf(IV)-02 in a toluene solution.
Figure 16:
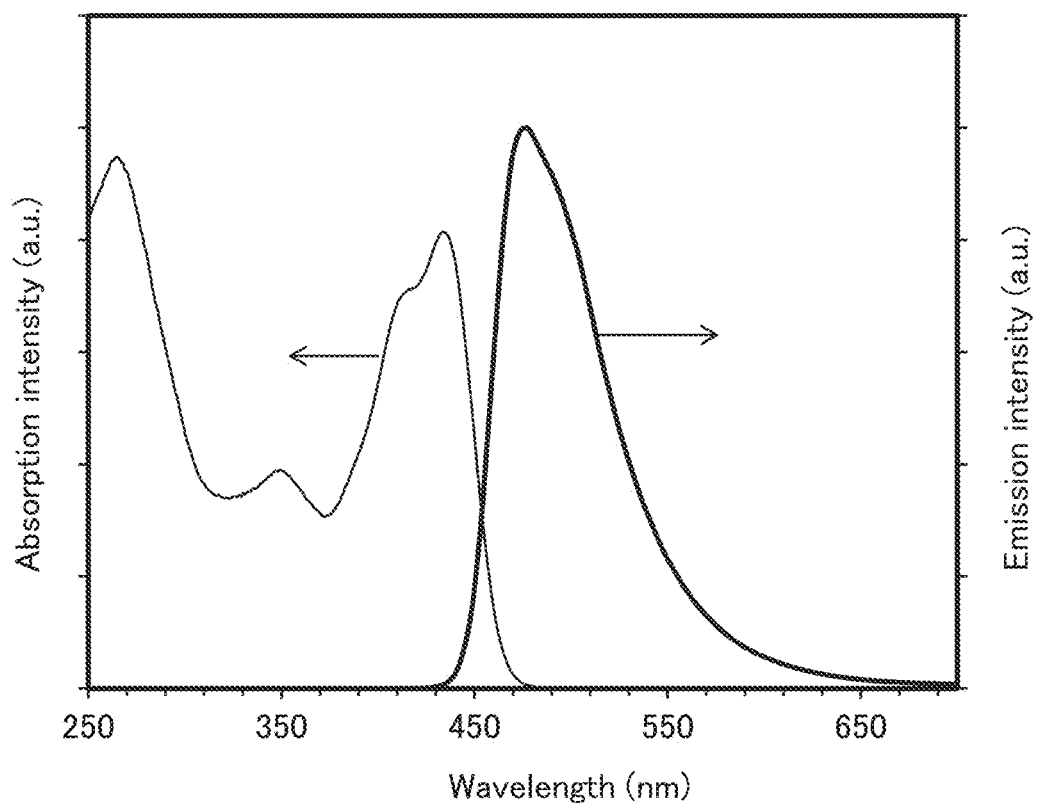
FIG. 16 shows an absorption spectrum and an emission spectrum of 3,10tBuPCA2Nbf(IV)-02 in a thin film state.

Next, FIG. 15 shows the measurement results of the absorption and emission spectra of 3,10tBuPCA2Nbf(IV)-02 in a toluene solution. FIG. 16 shows the absorption and emission spectra of 3,10tBuPCA2Nbf(IV)-02 in a thin film state. The solid thin film was fabricated over a quartz substrate by a vacuum evaporation method. The absorption spectrum of 3,10tBuPCA2Nbf(IV)-02 in the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, manufactured by JASCO Corporation). Quantum yields were measured using an absolute PL quantum yield measurement system (Quantaurus-QY, manufactured by Hamamatsu Photonics K.K.).

FIG. 15 shows that 3,10tBuPCA2Nbf(IV)-02 in the toluene solution has absorption peaks at 430 nm, 408 nm, and 348 nm, and emission spectrum peaks at 448 nm and 474 nm (excitation wavelength: 408 nm). In addition, FIG. 16 shows that the thin film of 3,10tBuPCA2Nbf(IV)-02 has absorption peaks at 434 nm, 416 nm, 349 nm, and 265 nm, and an emission spectrum peak at 482 nm (excitation wavelength: 400 nm). These results indicate that 3,10tBuPCA2Nbf(IV)-02 emits blue light and can be used as a host for a light-emitting substance or a substance that emits fluorescence in the visible region.

The measured quantum yield of 3,10tBuPCA2Nbf(IV)-02 in the toluene solution was as high as 89%, which indicates that 3,10tBuPCA2Nbf(IV)-02 is suitable for a light-emitting material.

Example 2

In this example, a method for synthesizing N,N'-Bis[9-(3-tert-butylphenyl)-9H-carbazol-2-yl]-N,N'-diphenyl-naphtho[2,3-b;6,7-b']bisbenzofuran-3,10-diamine (abbreviation: 3,10mtBuPCA2Nbf(IV)-02) represented by Structural Formula (135) in Embodiment 1 will be described. The structural formula of 3,10mtBuPCA2Nbf (IV)-02 is shown below.

[Chemical Formula 40]

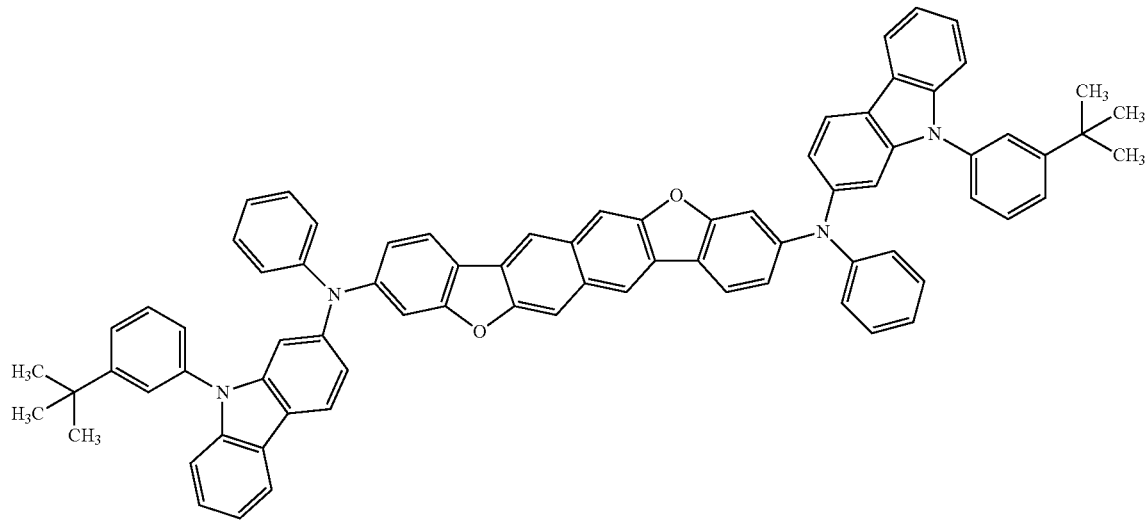

3,10mtBuPCA2Nbf(IV)-02

Step 1: Synthesis of 2-chloro-9-(3-tert-butylphenyl)-9H-carbazole

Into a 300-mL three-neck flask were put 5.0 g (25 mmol) of 2-chloro-9H-carbazole, 9.5 g (45 mmol) of 1-bromo-3-tert-butylbenzene, and 7.2 g (74 mmol) of sodium tert-butoxide. To the mixture were added 125 mL of xylene and 0.4 mL of tri(tert-butyl)phosphine (a 10% hexane solution), and the mixture was degassed by being stirred while the pressure was reduced. To the mixture was added 0.14 g (0.25 mmol) of bis(dibenzylideneacetone)palladium(0), and then the mixture was stirred while being heated at 150° C. under a nitrogen stream for 11.5 hours. After the stirring, toluene was added to the mixture, and the mixture was suction-filtered through Florisil, Celite, and alumina to give a filtrate. The obtained filtrate was concentrated to give an oily substance. The oily substance was purified by silica gel column chromatography (as the developing solvent, hexane was used), whereby 7.9 g of a colorless transparent oily substance was obtained in a yield of 95%. The synthesis scheme of Step 1 is shown below.

[Chemical Formula 41]

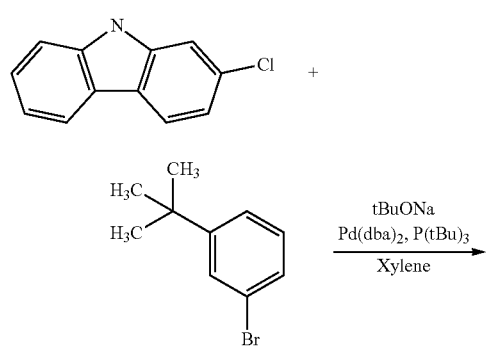

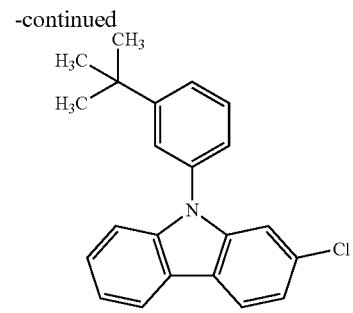

Measurement results obtained by nuclear magnetic resonance ($^1$H-NMR) spectroscopy of the oily substance obtained in Step 1 are shown below. The results revealed that 2-chloro-9-(3-tert-butylphenyl)-9H-carbazole was obtained in Step 1.

$^1$H-NMR (CDCl$_3$, 300 MHz): δ=1.39 (s, 9H), 7.23-7.45 (m, 6H), 7.45-7.57 (m, 3H), 8.04 (d, J1=8.4 Hz, 1H), 8.11 (d, J1=7.8 Hz, 1H).

Step 2: Synthesis of N-phenyl-9-(3-tert-butylphenyl)-9H-carbazol-2-amine

Into a 200-mL three-neck flask were put 7.9 g (24 mmol) of 2-chloro-9-(3-tert-butylphenyl)-9H-carbazole, 3.3 g (35 mmol) of aniline, 6.8 g (71 mmol) of sodium tert-butoxide, and 0.42 g (1.2 mmol) of di(1-adamantyl)-n-butylphosphine. To the mixture was added 115 mL of xylene, and the mixture was degassed by being stirred while the pressure was reduced. To the mixture was added 0.14 g (0.24 mmol) of bis(dibenzylideneacetone)palladium(0), and the mixture was stirred while being heated at 150° C. under a nitrogen stream for 6 hours. After the stirring, toluene was added to the mixture, and the mixture was suction-filtered through Florisil, Celite, and alumina, and the filtrate was concentrated to give a brown oily substance. The oily substance was purified by silica gel column chromatography (as the developing solvent, toluene and hexane in a ratio of 1:3 were used, and then toluene and hexane in a ratio of 1:2 were used). The oily substance failed to be purified was purified by silica gel column chromatography (as the developing solvent, hexane and ethyl acetate in a ratio of 20:1 were used). As a result, 7.2 g of a pale yellow solid was obtained in a yield of 78%. The synthesis scheme of Step 2 is shown below.

Measurement results obtained by nuclear magnetic resonance ($^1$H-NMR) spectroscopy of the pale yellow solid obtained in Step 2 are shown below. The results revealed that N-phenyl-9-(3-tert-butylphenyl)-9H-carbazol-2-amine was obtained in Step 2.

$^1$H-NMR (DMSO-d$_6$, 300 MHz): δ=1.35 (s, 9H), 6.82 (t, J1=6.9 Hz, 1H), 7.00 (dd, J1=8.4 Hz, J2=1.8 Hz, 1H), 7.05 (d, J1=1.8 Hz, 1H), 7.11-7.33 (m, 7H), 7.40 (dt, J1=7.8 Hz, J2=1.8 Hz, 1H), 7.50-7.61 (m, 3H), 8.03-8.08 (m, 2H), 8.36 (s, 1H).

Step 3: Synthesis of 3,10mtBuPCA2Nbf(IV)-02

Into a 200-mL three-neck flask were put 0.86 g (2.3 mmol) of 3,10-dichloronaphtho[2,3-b;6,7-b']bisbenzofuran, 2.2 g (5.5 mmol) of N-phenyl-9-(3-tert-butylphenyl)-9H-carbazol-2-amine, 82 mg (0.23 mmol) of di(1-adamantyl)-n-butylphosphine, and 1.3 g (14 mmol) of sodium tert-butoxide. To the mixture was added 25 mL of xylene. The mixture was degassed by being stirred while the pressure was reduced. To the mixture was added 26 mg (46 mol) of bis(dibenzylideneacetone)palladium(0), and the mixture was stirred while being heated at 150° C. under a nitrogen stream for 21 hours. After the stirring, toluene was added to the mixture, the mixture was suction-filtered through Florisil, Celite, and alumina, and the filtrate was concentrated to give a solid. The obtained solid was purified by silica gel column chromatography (as the developing solvent, toluene and hexane in a ratio of 1:2 were used) to give a solid. The obtained solid was recrystallized with toluene/ethyl acetate, whereby 1.9 g of a yellow solid was obtained in a yield of 75%.

Then, 1.2 g of the obtained solid was sublimated and purified by a train sublimation method. The purification by sublimation was performed by heating at 385° C. under a pressure of 2.2×10$^{-2}$ Pa with an argon flow rate of 0 mL/min. After the purification by sublimation, 1.0 g of a yellow solid was obtained at a collection rate of 85%. The synthesis scheme of Step 3 is shown below.

[Chemical Formula 42]

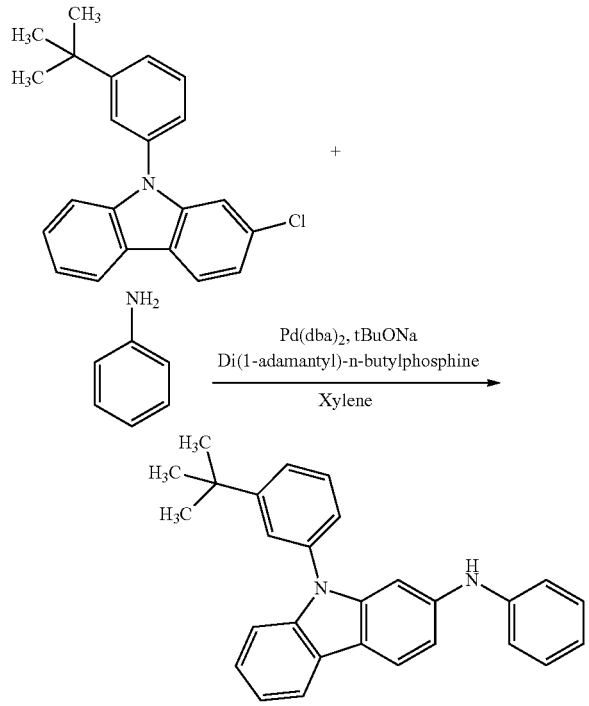

[Chemical Formula 43]

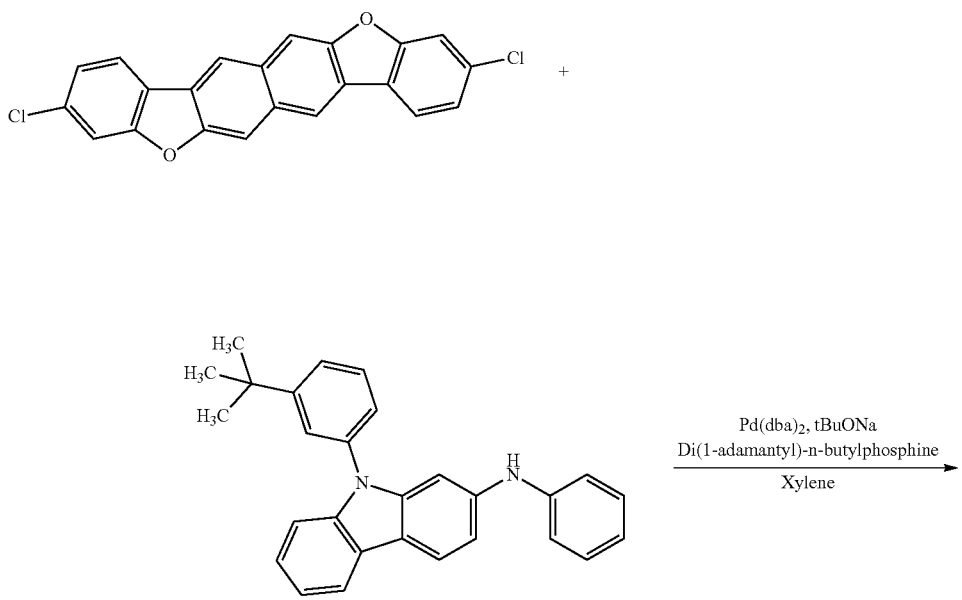

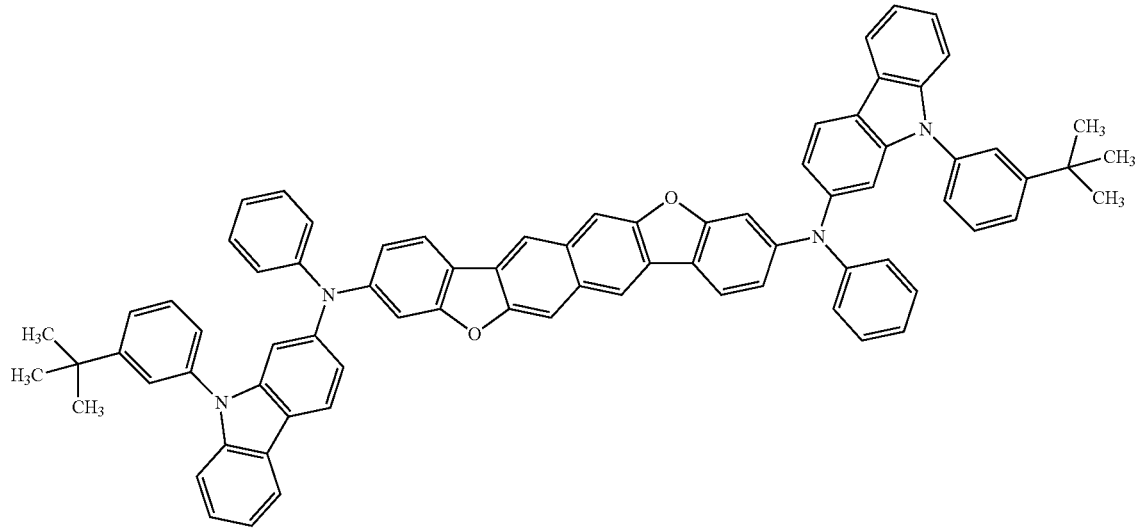

Figure 17A:
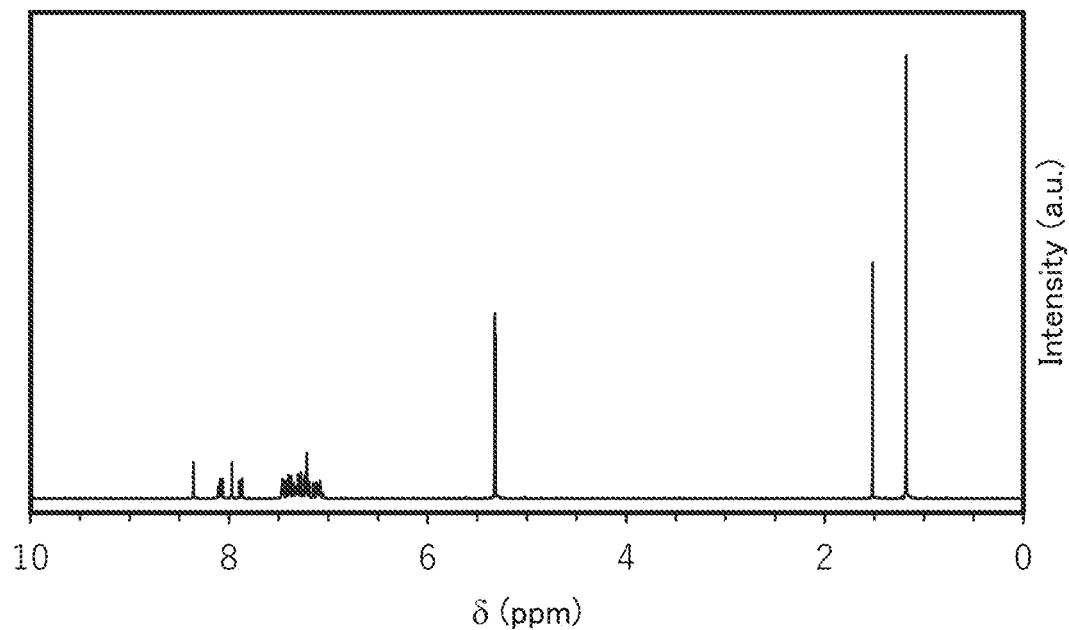
FIGS. 17A and 17B are H-NMR charts of 3,10mtBuPCA2Nbf(IV)-02.
Figure 17B:
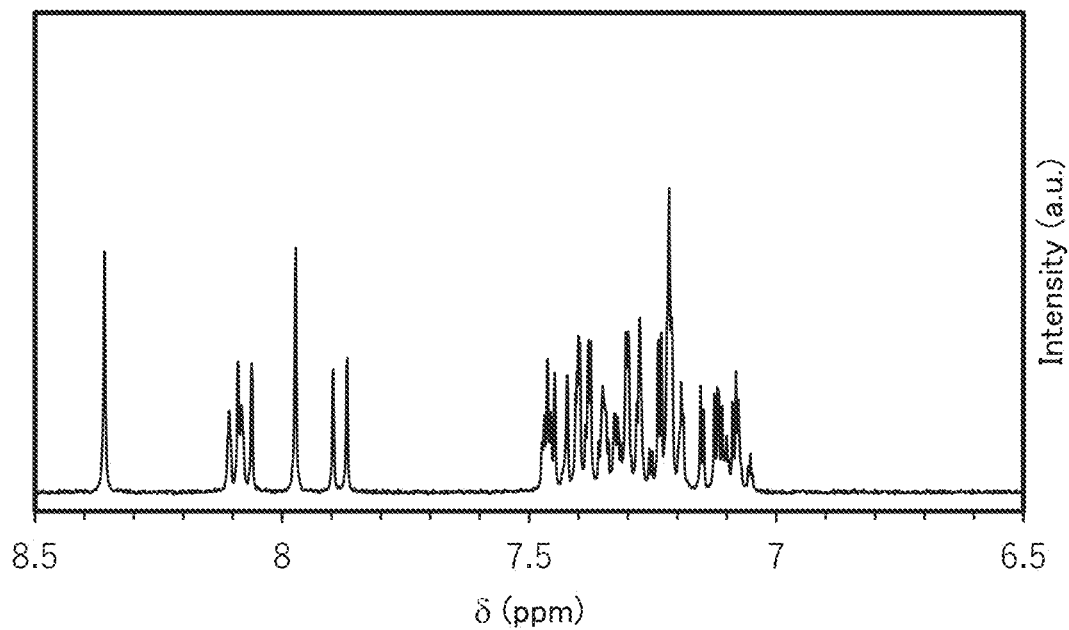

FIGS. 17A and 17B show measurement results obtained by nuclear magnetic resonance ($^1$H-NMR) spectroscopy of the yellow solid obtained in Step 3, whose numerical data is shown below. The results revealed that 3,10mtBuPCA2Nbf (IV)-02 was obtained in Step 3.

$^1$H-NMR (CD$_2$Cl$_2$, 300 MHz): δ=1.18 (s, 18H), 7.05-7.47 (m, 32H), 7.89 (d, J1=2.4 Hz, 2H), 7.97 (s, 2H), 8.06-8.11 (m, 4H), 8.36 (s, 2H).

Figure 18:
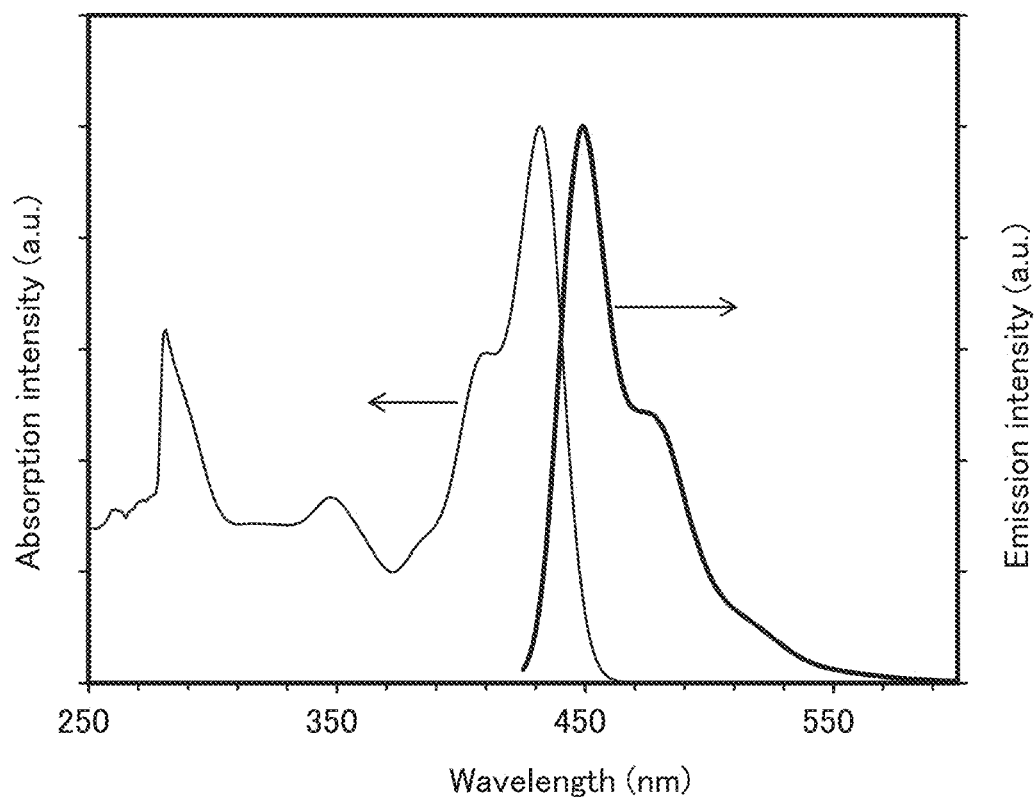
FIG. 18 shows an absorption spectrum and an emission spectrum of 3,10mtBuPCA2Nbf(IV)-02 in a toluene solution.
Figure 19:
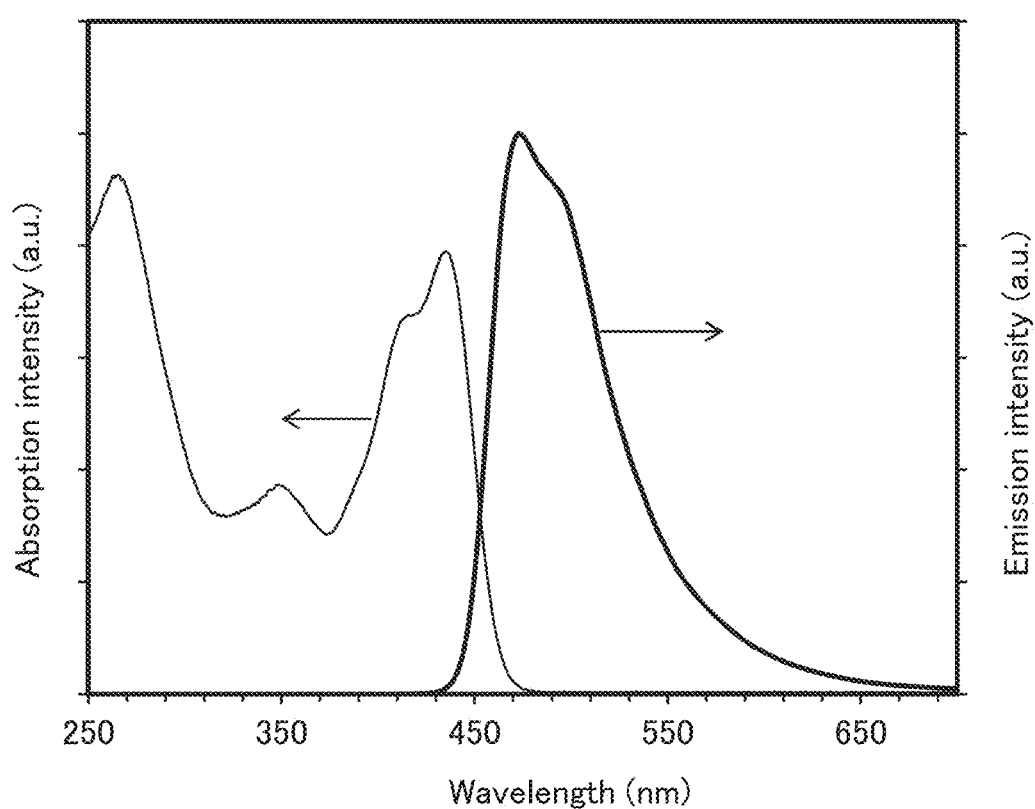
FIG. 19 shows an absorption spectrum and an emission spectrum of 3,10mtBuPCA2Nbf(IV)-02 in a thin film state.

Next, FIG. 18 shows the measurement results of the absorption and emission spectra of 3,10mtBuPCA2Nbf(IV)-02 in a toluene solution. FIG. 19 shows the absorption and emission spectra of a thin film of 3,10mtBuPCA2Nbf(IV)-02. The solid thin film was fabricated over a quartz substrate by a vacuum evaporation method. The absorption spectrum of 3,10mtBuPCA2Nbf(IV)-02 in the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, manufactured by JASCO Corporation). Quantum yields were measured using an absolute PL quantum yield measurement system (Quantaurus-QY, manufactured by Hamamatsu Photonics K.K.).

FIG. 18 shows that 3,10mtBuPCA2Nbf(IV)-02 in the toluene solution has absorption peaks at 430 nm, 408 nm, and 348 nm, and emission spectrum peaks at 448 nm and 474 nm (excitation wavelength: 408 nm). In addition, FIG. 19 shows that the thin film of 3,10mtBuPCA2Nbf(IV)-02 has absorption peaks at 434 nm, 416 nm, 349 nm, and 265 nm, and an emission spectrum peak at 482 nm (excitation wavelength: 400 nm). These results indicate that 3,10mtBuPCA2Nbf(IV)-02 emits blue light and can be used as a host for a light-emitting substance or a substance that emits fluorescence in the visible region.

The measured quantum yield of 3,10mtBuPCA2Nbf(IV)-02 in the toluene solution was as high as 89%, which indicates that 3,10mtBuPCA2Nbf(IV)-02 is suitable for a light-emitting material.

Example 3

In this example, light-emitting devices of one embodiment of the present invention and a comparative light-emitting device are described. Structural formulae of organic compounds used in this example are shown below.

[Chemical Formula 44]
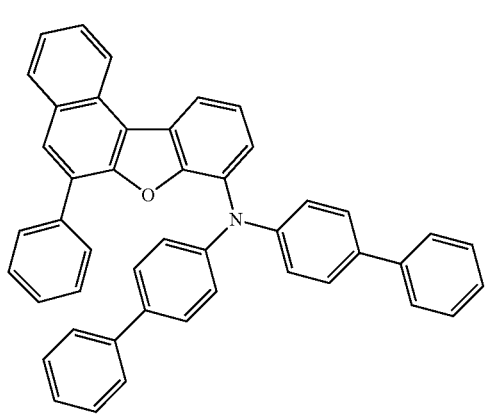
BBABnF
(i)
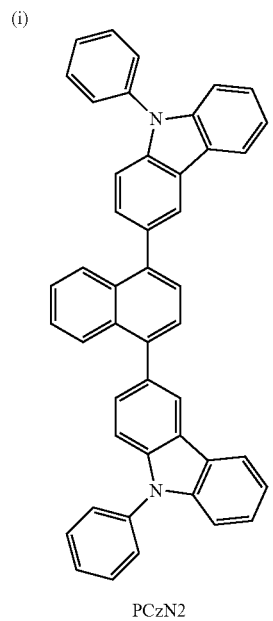
PCzN2
(ii)
(iii)
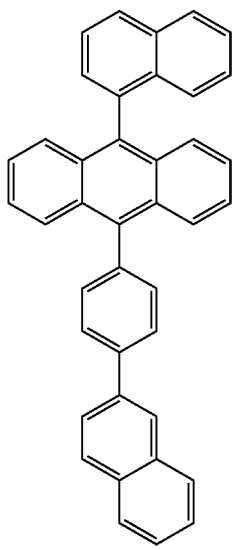
αB-βNPAnth -continued
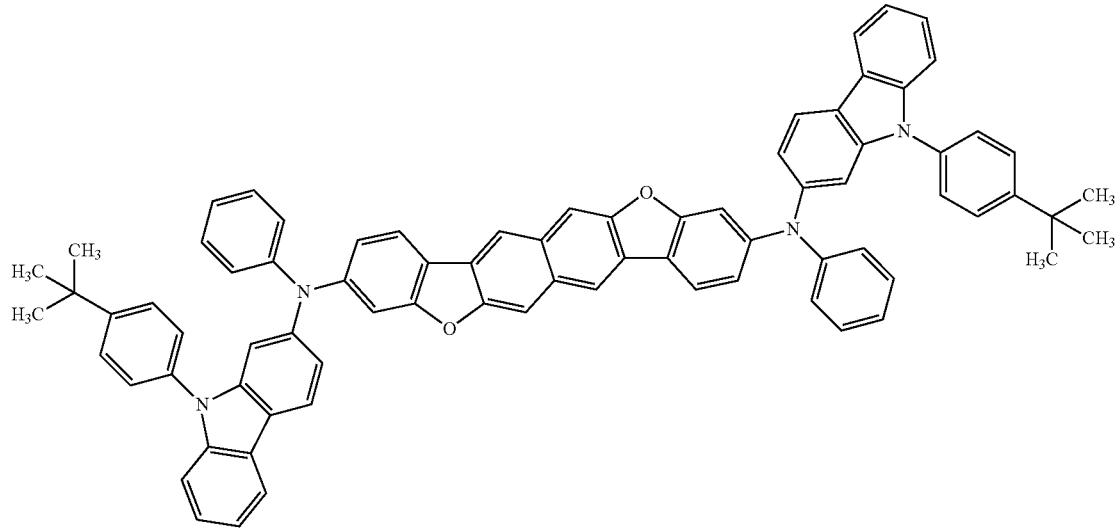
3,10tBuPCA2Nbf(IV)-02 (iv)
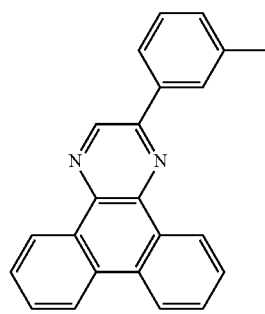
2mDBTBPDBq-II (v)
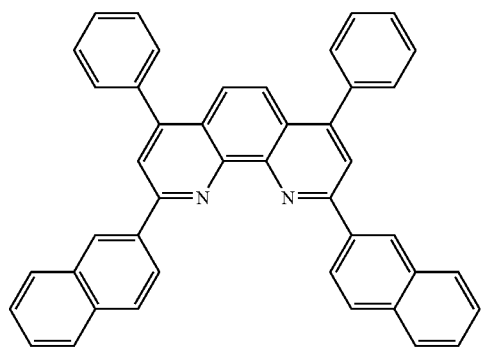
NBPhen (vi)
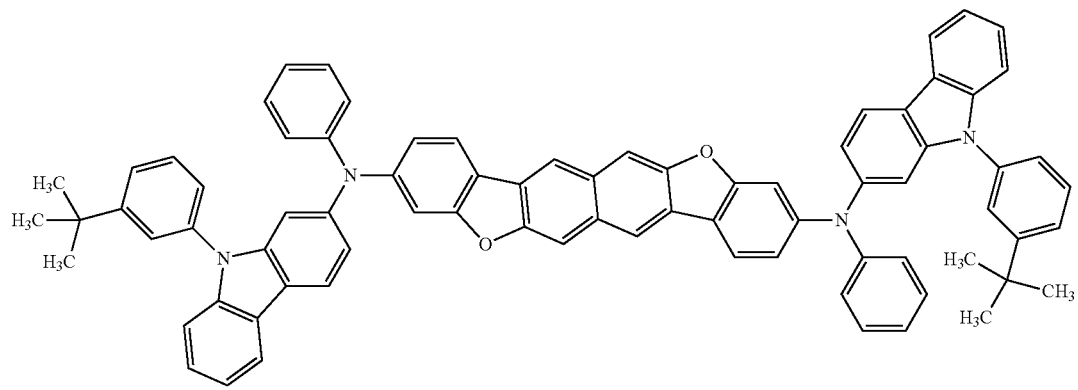
3,10mtBuPCA2Nbf(IV)-02 (vii)

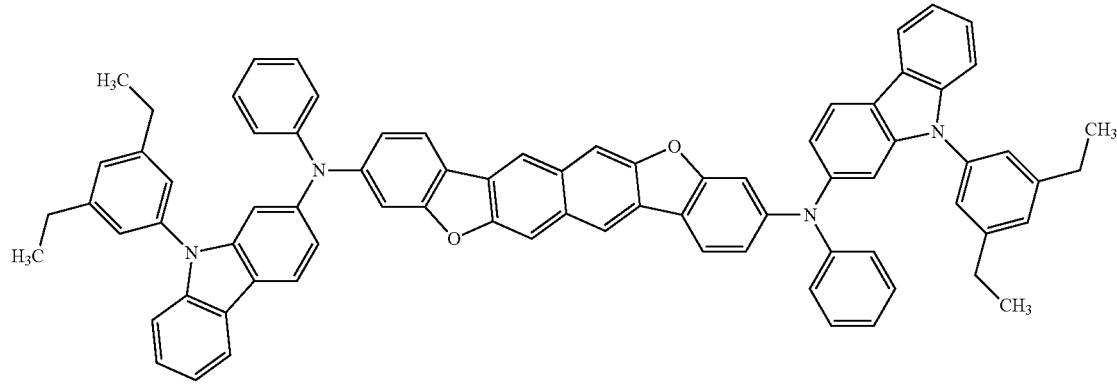

3,10mmEtPCA2Nbf(IV)-02

(Fabrication Method of Light-Emitting Device 1)

First, indium tin oxide containing silicon oxide (ITSO) was deposited over a glass substrate by a sputtering method to form the first electrode 101. The thickness of the first electrode 101 was 70 nm and the electrode area was 2 mm×2 mm.

Next, in pretreatment for forming the light-emitting device over a substrate, a surface of the substrate was washed with water, baking was performed at 200° C. for 1 hour, and then UV ozone treatment was performed for 370 seconds.

After that, the substrate was transferred into a vacuum evaporation apparatus where the pressure was reduced to approximately 10-4 Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the side on which the first electrode 101 was formed faced downward. Then, N,N-bis (4-biphenyl)-6-phenylbenzo[b]naphtho[1,2-d]furan-8-amine (abbreviation: BBABnf) represented by Structural Formula (i) and an electron-acceptor material (OCHD-001) were deposited by co-evaporation to a thickness of 10 nm over the first electrode 101 using a resistance-heating method such that the weight ratio of BBABnf to OCHD-001 was 1:0.1, whereby the hole-injection layer 111 was formed.

Subsequently, over the hole-injection layer 111, BBABnf was deposited by evaporation to a thickness of 20 nm, and then 3,3'-(naphthalene-1,4-diyl)bis(9-phenyl-9H-carbazole) (abbreviation: PCzN2) represented by Structural Formula (ii) was deposited by evaporation to a thickness of 10 nm, whereby the hole-transport layer 112 was formed.

Then, 9-(1-naphthyl)-10-[4-(2-naphthyl)phenyl]anthracene (abbreviation: αN-βNPAnth) represented by Structural Formula (iii) and N,N'-Bis[9-(4-tert-butylphenyl)-9H-carbazol-2-yl]-N,N'-diphenyl-naphtho[2,3-b;6,7-b']bisbenzofuran-3,10-diamine (abbreviation: 3,10tBuPCA2Nbf(IV)-02) represented by Structural Formula (iv) were deposited by co-evaporation to a thickness of 25 nm such that the weight ratio of αN-βNPAnth to 3,10tBuPCA2Nbf(IV)-02 was 1:0.015, whereby the light-emitting layer 113 was formed.

Then, over the light-emitting layer 113, 2-[3'-(dibenzothiophen-4-yl)biphenyl-3-yl]dibenzo[f,h]quinoxaline (abbreviation: 2mDBTBPDBq-II) represented by Structural Formula (v) was deposited to a thickness of 15 nm, and then 2,9-di(2-naphthyl)-4,7-diphenyl-1,10-phenanthroline (abbreviation: NBPhen) represented by Structural Formula (vi) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Thus, the light-emitting device 1 of this example was fabricated.

(Fabrication Method of Light-Emitting Device 2)

The light-emitting device 2 was fabricated in the same manner as that of the light-emitting device 1 except that 3,10tBuPCA2Nbf(IV)-02 was replaced with N,N'-Bis[9-(3-tert-butylphenyl)-9H-carbazol-2-yl]-N,N'-diphenyl-naphtho[2,3-b;6,7-b']bisbenzofuran-3,10-diamine (abbreviation: 3,10mtBuPCA2Nbf(IV)-02) represented by Structural Formula (vii).

(Fabrication Method of Comparative Light-Emitting Device 1)

The comparative light-emitting device 1 was fabricated in the same manner as that of the light-emitting device 1 except that 3,10tBuPCA2Nbf(IV)-02 was replaced with N,N'-Bis[9-(3,5-diethylphenyl)-9H-carbazol-2-yl]-N,N'-diphenyl-naphtho[2,3-b;6,7-b']bisbenzofuran-3,10-diamine (abbreviation: 3,10mmEtPCA2Nbf(IV)-02) represented by Structural Formula (viii).

The structures of the light-emitting devices and the comparative light-emitting device are listed in the following table.

TABLE 1

| | Hole-injection layer 10 nm | Hole-transport layer 1 20 nm | Hole-transport layer 2 10 nm | Light-emitting layer 25 nm | Electron-transport layer 1 15 nm | Electron-transport layer 2 10 nm |
|---|---|---|---|---|---|---|
| Light-emitting device 1 | BBABnf:OCHD-001 (1:0.1) | BBABnf | PCzN2 | *1 | 2mDBTBPDBq-II | NBPhen |
| Light-emitting device 2 | | | | *2 | | |
| Comparative light-emitting device 1 | | | | *3 | | |

*1 αN-βNPAnth:3,10tBuPCA2Nbf(IV)-02 (1:0.015)
*2 αN-βNPAnth:3,10mtBuPCA2Nbf(IV)-02 (1:0.015)
*3 αN-βNPAnth:3,10mmEtPCA2Nbf(IV)-02 (1:0.015)

The light-emitting devices and the comparative light-emitting device were sealed using a glass substrate in a glove box containing a nitrogen atmosphere so as not to be exposed to the air (a sealing material was applied to surround the devices and UV treatment and heat treatment at 80° C. for 1 hour were performed at the time of sealing). Then, the initial characteristics of the light-emitting devices and the comparative light-emitting device were measured.

Figure 20:
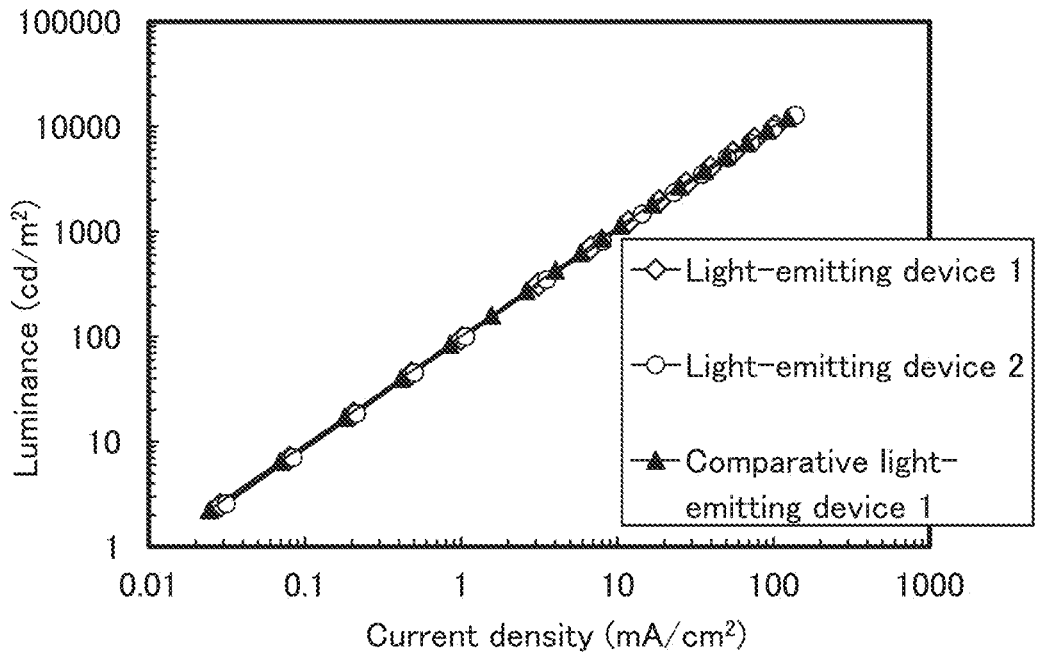
FIG. 20 shows the luminance-current density characteristics of a light-emitting device 1, a light-emitting device 2, and a comparative light-emitting device 1.
Figure 21:
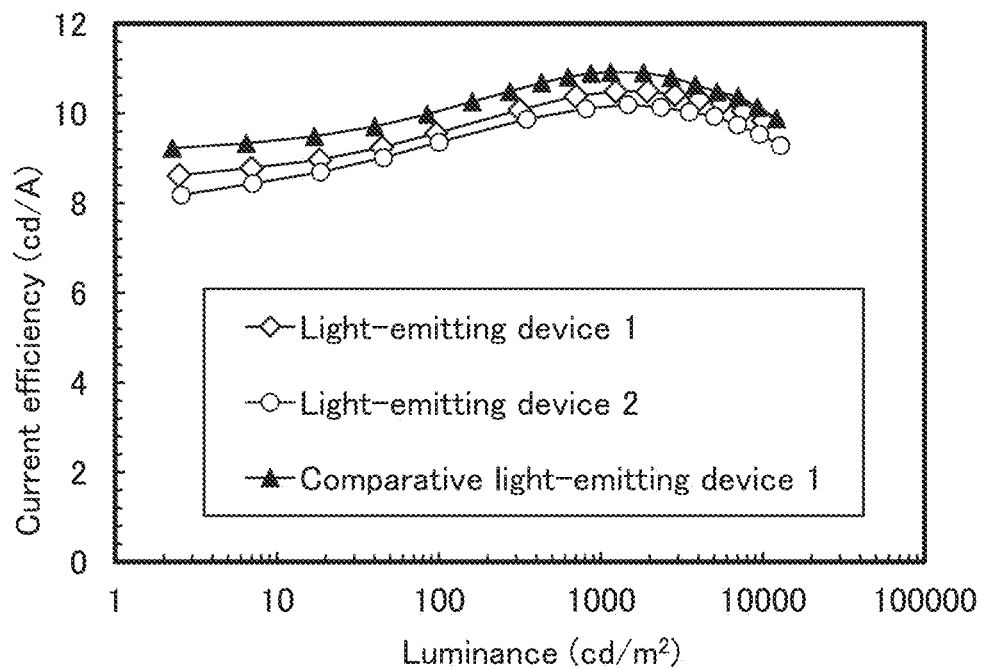
FIG. 21 shows the current efficiency-luminance characteristics of the light-emitting device 1, the light-emitting device 2, and the comparative light-emitting device 1.
Figure 22:
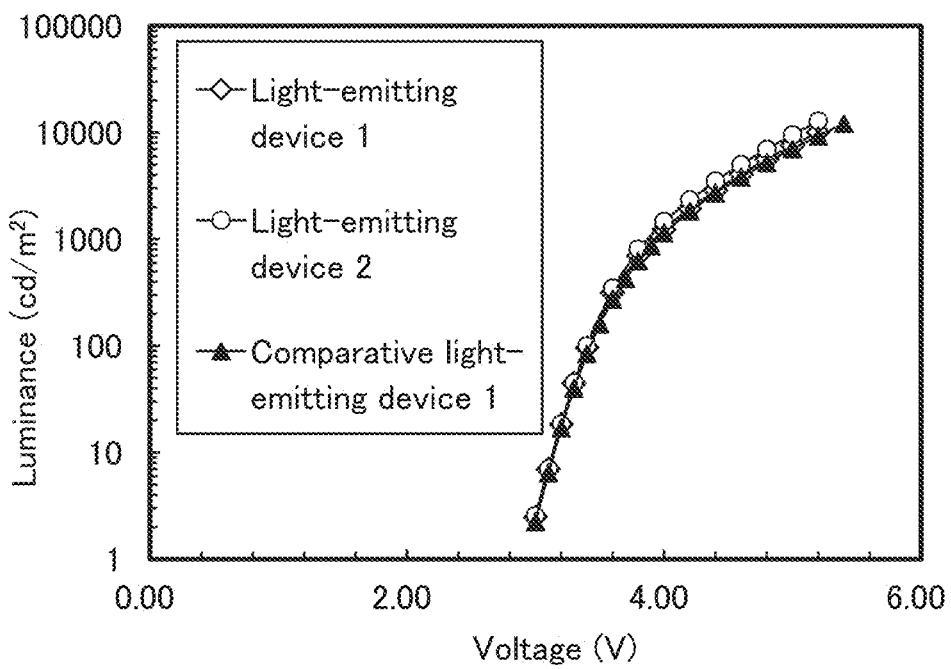
FIG. 22 shows the luminance-voltage characteristics of the light-emitting device 1, the light-emitting device 2, and the comparative light-emitting device 1.
Figure 23:
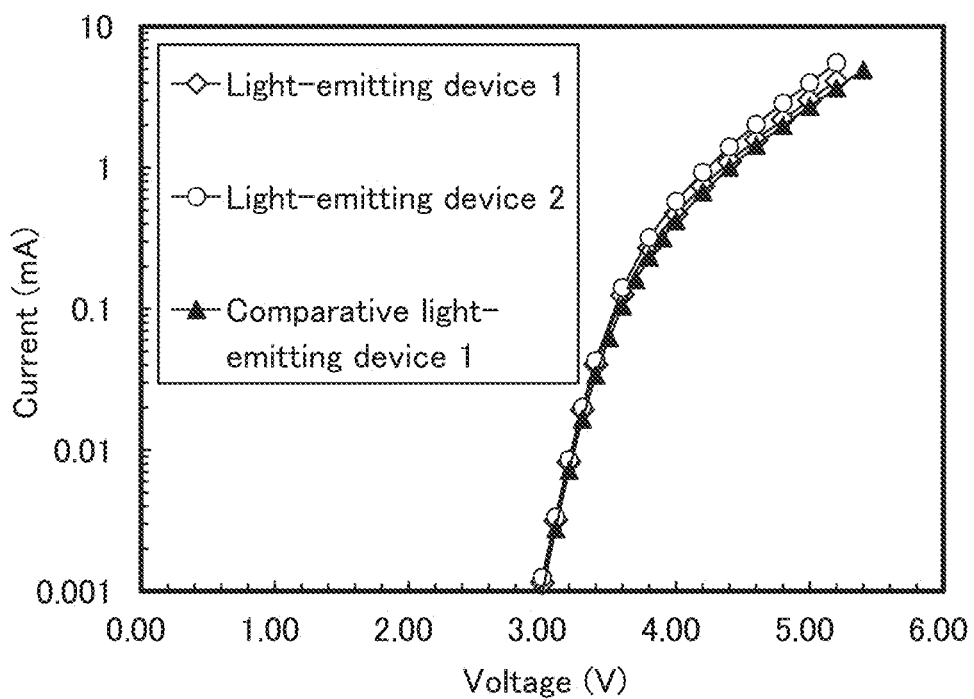
FIG. 23 shows the current-voltage characteristics of the light-emitting device 1, the light-emitting device 2, and the comparative light-emitting device 1.
Figure 24:
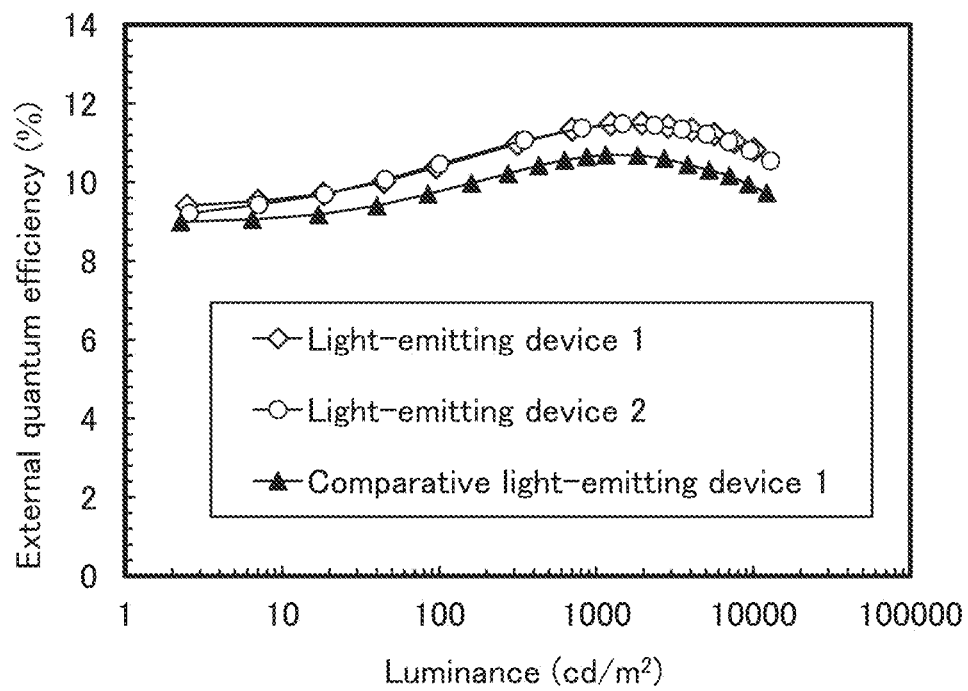
FIG. 24 shows the external quantum efficiency-luminance characteristics of the light-emitting device 1, the light-emitting device 2, and the comparative light-emitting device 1.
Figure 25:
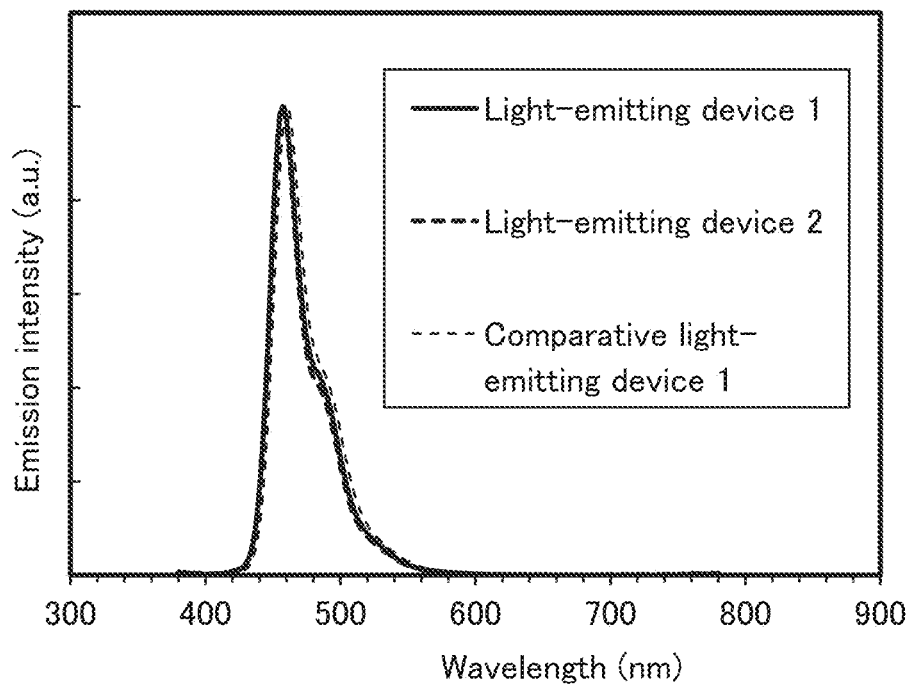
FIG. 25 shows the emission spectra of the light-emitting device 1, the light-emitting device 2, and the comparative light-emitting device 1.

FIG. 20 shows the luminance-current density characteristics of the light-emitting device 1, the light-emitting device 2, and the comparative light-emitting device 1. FIG. 21 shows the current efficiency-luminance characteristics thereof. FIG. 22 shows the luminance-voltage characteristics thereof. FIG. 23 shows the current-voltage characteristics thereof. FIG. 24 shows the external quantum efficiency-luminance characteristics thereof. FIG. 25 shows the emission spectra thereof. The following table shows the main characteristics of the light-emitting devices and the comparative light-emitting device at a luminance of about 1000 cd/m$^2$.

FIGS. 20 to 25 show that the light-emitting devices 1 and 2 of one embodiment of the present invention and the comparative light-emitting device 1 are EL devices having high emission efficiency.

Shown here are the results of examination on the properties of the following substances: 3,10tBuPCA2Nbf(IV)-02 used as a light-emitting material of the light-emitting device 1; 3,10mtBuPCA2Nbf(IV)-02 used as alight-emitting material of the light-emitting device 2; 3,10mmEtPCA2Nbf(IV)-02 used as alight-emitting material of the comparative light-emitting device 1; N,N'-Bis[9-(3,5-dihexylphenyl)-9H-carbazol-2-yl]-N,N'-diphenyl-naphtho[2,3-b;6,7-b']bis-benzofuran-3,10-diamine (abbreviation: 3,10mmHexPCA2Nbf(IV)-02) represented by Structural Formula (ix); and 3,10-Bis[N-(9-phenyl-9H-carbazol-2-yl)-N-phenylamino]naphtho[2,3-b;6,7-b']bisbenzofuran (abbreviation: 3,10PCA2Nbf(IV)-02) represented by Structural Formula (x).

TABLE 2

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 1 | 4.0 | 0.47 | 11.8 | 0.14 | 0.10 | 10.5 | 11.5 |
| Light-emitting device 2 | 3.8 | 0.32 | 8.0 | 0.14 | 0.10 | 10.1 | 11.4 |
| Comparative light-emitting device 1 | 3.9 | 0.32 | 8.0 | 0.13 | 0.12 | 10.9 | 10.6 |

[Chemical Formula 45]

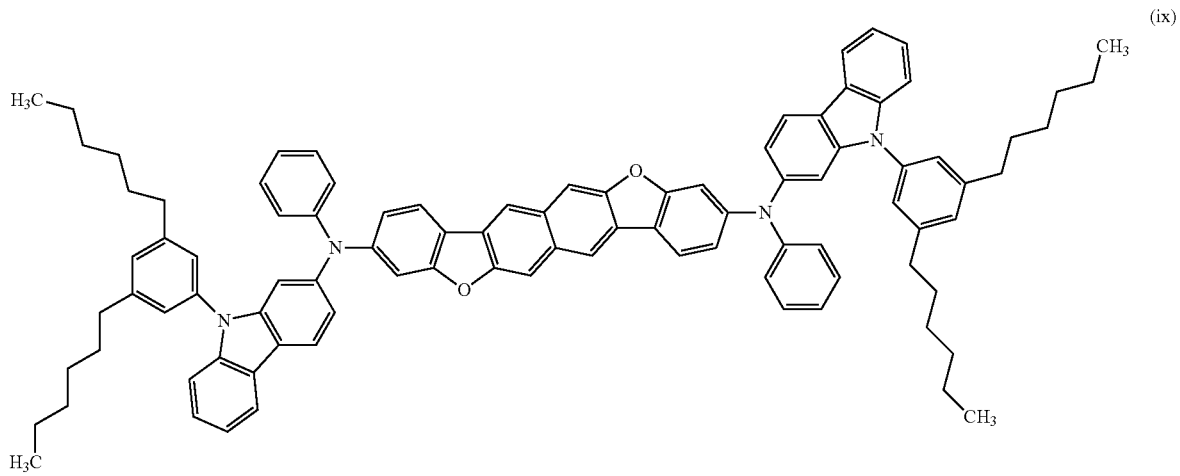

3,10mmHexPCA2Nbf(IV)-02

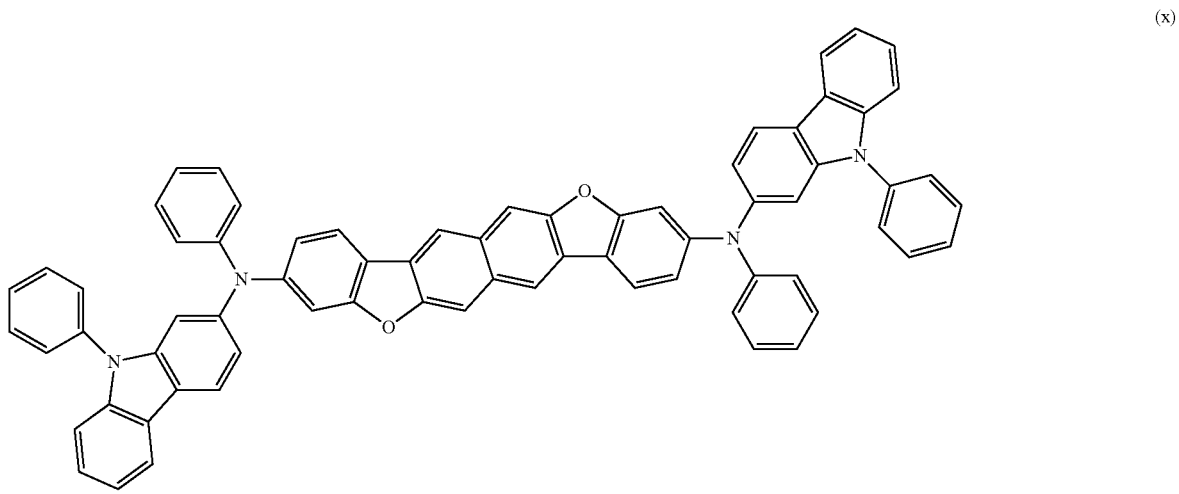

3,10PCA2Nbf(IV)-02

Note that 3,10tBuPCA2Nbf(IV)-02 is a substance in which a tert-butyl group is bonded to the para-position of a phenyl group that is bonded to the 9-position of a carbazolyl group included in 3,10PCA2Nbf(IV)-02. In addition, 3,10mtBuPCA2Nbf(IV)-02 is a substance in which a tert-butyl group is bonded to the meta-position of the phenyl group that is bonded to the 9-position of the carbazolyl group included in 3,10PCA2Nbf(IV)-02. In addition, 3,10mmEtPCA2Nbf(IV)-02 is a substance in which two ethyl groups are bonded to the meta-position of the phenyl group that is bonded to the 9-position of the carbazolyl group included in 3,10PCA2Nbf(IV)-02. In addition, 3,10mmHexPCA2Nbf(IV)-02 is a substance in which two n-hekyl groups are bonded to the meta-position.

Figure 26:
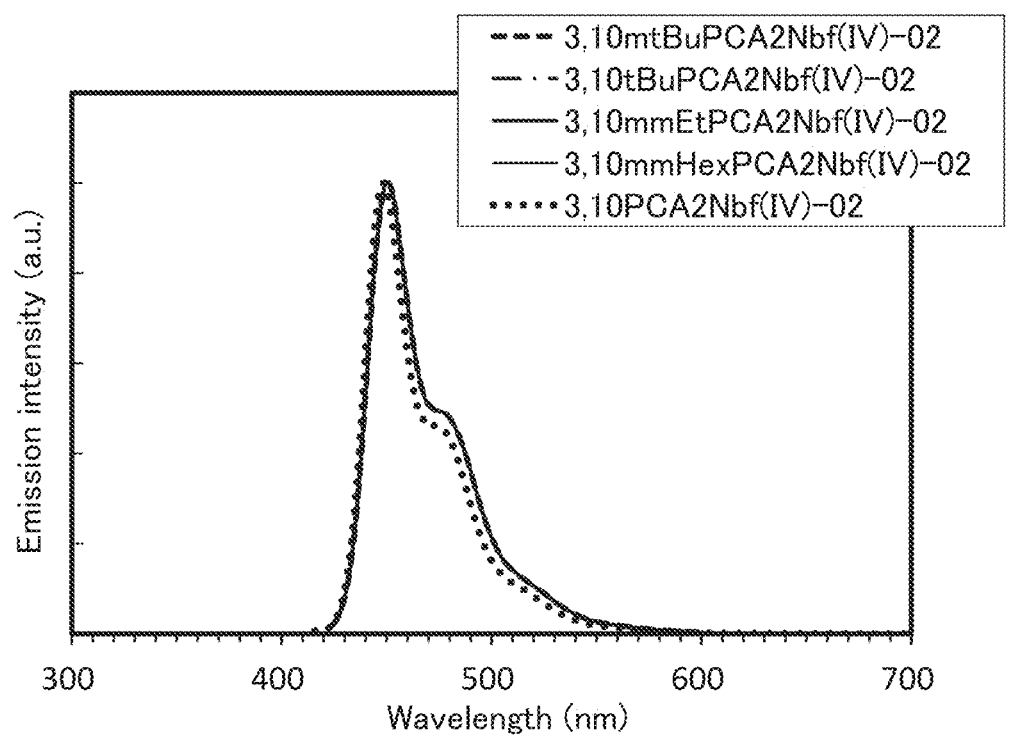
FIG. 26 shows the emission spectra of 3,10tBuPCA2Nbf (IV)-02, 3,10mtBuPCA2Nbf(IV)-02, 3,10mmEtPCA2Nbf (IV)-02, 3,10mmHexPCA2Nbf(IV)-02, and 3,10PCA2Nbf (IV)-02, each of which is in a solution state.

FIG. 26 shows the emission spectra of the five substances each in a toluene solution. As shown in FIG. 26, the five substances have substantially the same emission spectrum shapes with peaks at similar positions. This indicates that the four substances in the above paragraph except for 3,10PCA2Nbf(IV)-02 each receive little influence on the conjugation and the emission color from the introduction of the above-described substituent to the phenyl group bonded to the 9-position of the carbazolyl group.

That is, similarly to 3,10PCA2Nbf(IV)-02 emitting blue light with high color purity, 3,10tBuPCA2Nbf(IV)-02, 3,10mtBuPCA2Nbf(IV)-02, 3,10mmEtPCA2Nbf(IV)-02, and 3,10mmHexPCA2Nbf(IV)-02 were found to be organic compounds emitting blue light with high color purity, whose emission and absorption spectra are hardly affected by the substituent introduction. As for 3,10PCA2Nbf(IV)-02 including arylamine bonded to a main skeleton that is a luminophore, it is known that the emission spectrum shifts to a longer wavelength side and the color purity decreases when a substituent similar to the above substituents is introduced to a phenyl group in the arylamine.

Figure 27:
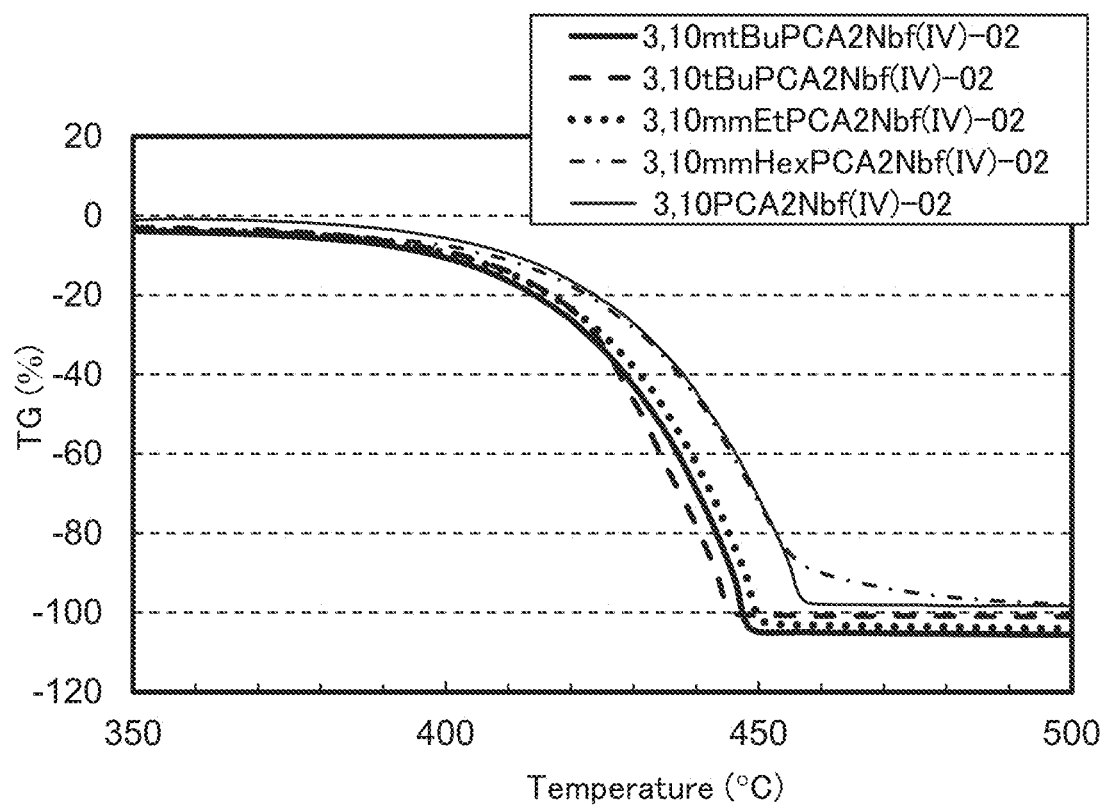
FIG. 27 shows the relation between weight and temperature in a thermogravimetry-differential thermal analysis performed on 3,10tBuPCA2Nbf(IV)-02, 3,10mtBuPCA2Nbf (IV)-02, 3,10mmEtPCA2Nbf(IV)-02, 3,10mmHexPCA2Nbf(IV)-02, and 3,10PCA2Nbf(IV)-02.

Then, the thermogravimetry-differential thermal analysis (TG-DTA) was performed on these five substances. The measurement was performed using a high vacuum differential type differential thermal balance (TG-DTA2410SA, manufactured by Bruker AXS K.K.). FIG. 27 shows the relationship between weight and temperature measured at 10 Pa and a temperature rising rate of 10° C./min. Table 3 shows temperatures (weight loss temperatures) at which the weight of the above organic compounds decreases from the initial amount by −5%, −10% and −50%.

TABLE 3

| | | TG [%] | | |
|---|---|---|---|---|
| | | −5 | −10 | −50 |
| Temeperature [° C.] | (x) 3,10PCA2Nbf(IV)-02 | 398 | 411 | 442 |
| | (iv) 3,10tBuPCA2Nbf(IV)-02 | 384 | 403 | 431 |
| | (vii) 3,10mtBuPCA2Nbf(IV)-02 | 374 | 399 | 433 |
| | (viii) 3,10mmEtPCA2Nbf(IV)-02 | 380 | 402 | 436 |
| | (ix) 3,10mmHexPCA2Nbf(IV)-02 | 384 | 407 | 442 |

FIG. 27 and Table 3 show that, among the four substances in which an alkyl group is bonded to the phenyl group bonded to the 9-position of the carbazolyl group included in 3,10PCA2Nbf(IV)-02, three substances except for

[Chemical Formula 46]

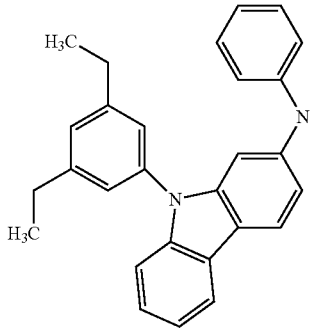
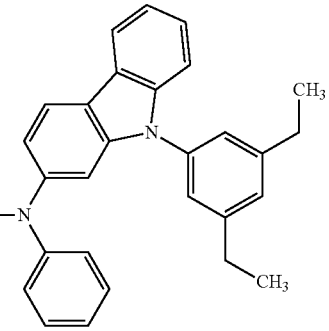

3,10mmEtPCA2Nbf(IV)-02

3,10mmHexPCA2Nbf(IV)-02 have a lower weight loss temperature and a higher sublimation property than 3,10PCA2Nbf(IV)-02, which does not have a substituent bonded to the phenyl group bonded to the 9-position of the carbazolyl group.

Figure 28:
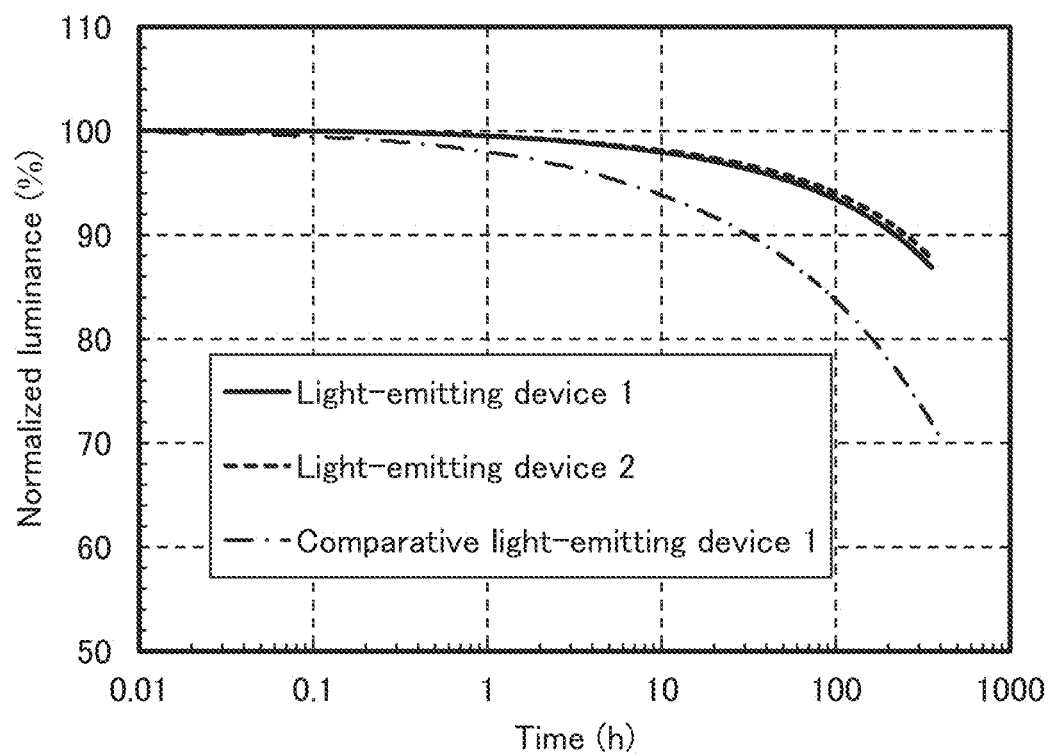
FIG. 28 is a graph showing a change in luminance over driving time of the light-emitting device 1, the light-emitting device 2, and the comparative light-emitting device 1.

FIG. 28 shows a change in luminance over driving time of the light-emitting device 1, the light-emitting device 2, and the comparative light-emitting device 1 at a current density of 50 mA/cm². As shown in FIG. 28, the light-emitting devices 1 and 2 of one embodiment of the present invention show more favorable characteristics than the comparative light-emitting device 1. This reveals that an ethyl-substituted product such as 3,10mmEtPCA2Nbf(IV)-02 used in the comparative light-emitting device 1 increases the sublimation property but decreases the reliability.

Note that 3,10mmHexPCA2Nbf(IV)-02 was decomposed during purification by sublimation, and thus a light-emitting device including 3,10mmHexPCA2Nbf(IV)-02 failed to be fabricated and the device data was notable to be obtained. This reveals that an n-hexyl-substituted product has a poor sublimation property.

As described above, the organic compound of one embodiment of the present invention includes a secondary or tertiary alkyl group in which a carbon atom bonded to a phenyl group bonded to the 9-position of a carbazolyl group branches, and thus can have a favorable sublimation property and enables a highly reliable light-emitting device to be fabricated.

Reference Example 1

Reference Synthesis Example 1

In this reference synthesis example, a method for synthesizing N,N'-Bis[9-(3,5-diethylphenyl)-9H-carbazol-2-yl]-N,N'-diphenyl-naphtho[2,3-b;6,7-b']bisbenzofuran-3,10-diamine (abbreviation: 3,10mmEtPCA2Nbf(IV)-02), which is used in Example 3, is described. The structural formula of 3,10mmEtPCA2Nbf(IV)-02 is shown below.

Step 1: Synthesis of 2-chloro-9-(3,5-diethylphenyl)-9H-carbazole

Into a 300-mL three-neck flask were put 3.2 g (16 mmol) of 2-chloro-9H-carbazole, 5.0 g (23 mmol) of 1-bromo-3,5-diethylbenzene, and 4.5 g of (47 mmol) of sodium tert-butoxide. To the mixture were added 80 mL of xylene and 0.2 mL of tri(tert-butyl)phosphine (a 10% hexane solution), and the mixture was degassed by being stirred while the pressure was reduced. To the mixture was added 90 mg (0.16 mmol) of bis(dibenzylideneacetone)palladium(0), and the mixture was stirred while being heated at 150° C. under a nitrogen stream for 7 hours. After the stirring, toluene was added to the mixture, and the mixture was suction-filtered through Florisil, Celite, and alumina to give a filtrate. The obtained filtrate was concentrated to give an oily substance. The oily substance was purified by silica gel column chromatography (as the developing solvent, hexane was used), whereby 4.8 g of a colorless transparent oily substance was obtained in a yield of 93%. The synthesis scheme of Step 1 is shown below.

[Chemical Formula 47]

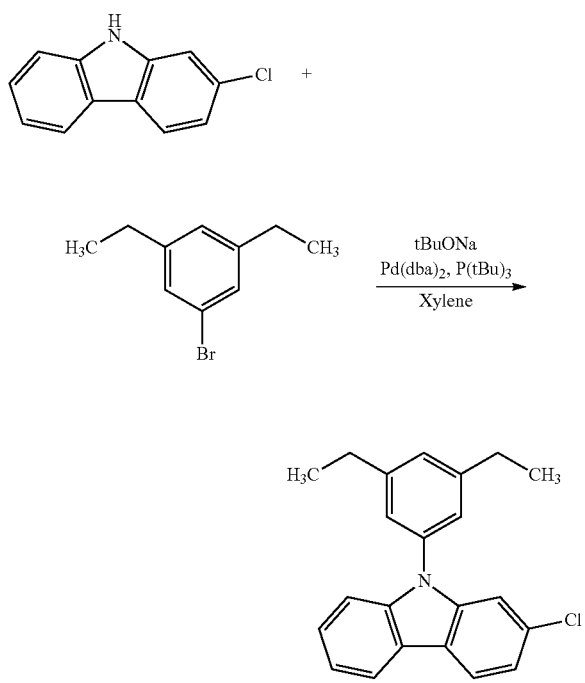

Measurement results obtained by nuclear magnetic resonance ($^1$H-NMR) spectroscopy of the colorless transparent oily substance obtained in Step 1 are shown below. The results revealed that 2-chloro-9-(3,5-diethylphenyl)-9H-carbazole was obtained in Step 1.

$^1$H-NMR (CDCl$_3$, 300 MHz): δ=1.31 (t, J1=7.5 Hz, 6H), 2.75 (q, J1=7.5 Hz, 4H), 7.12-7.31 (m, 2H), 7.36-7.44 (m, 3H), 8.03 (dd, J1=8.1 Hz, J2=0.3 Hz, 1H), 8.25 (ddd, J1=7.8 Hz, J2=1.2 Hz, J3=0.9 Hz, 1H).

Step 2: Synthesis of N-[9-(3,5-diethylphenyl)-9H-carbazol-2-yl]-N-phenylamine

Into a 300-mL three neck flask were put 4.8 g (14 mmol) of 2-chloro-9-(3,5-diethylphenyl)-9H-carbazole, 2.0 g of (22 mmol) of aniline, 4.2 g (43 mmol) of sodium tert-butoxide, and 0.26 g (0.72 mmol) of di(1-adamantyl)-n-butylphosphine. To the mixture was added 75 mL of xylene, and the mixture was degassed by being stirred while the pressure was reduced. To the mixture was added 83 mg (0.14 mmol) of bis(dibenzylideneacetone)palladium(0), and the mixture was stirred while being heated at 150° C. under a nitrogen stream for 7 hours. After the stirring, toluene was added to the mixture, the mixture was suction-filtered through Florisil, Celite, and alumina, and the filtrate was concentrated to give a solid. The solid was purified by silica gel column chromatography (as the developing solvent, toluene and hexane in a ratio of 3:7 were used, and then toluene and hexane in a ratio of 2:3 were used). Ethanol and hexane were added to the obtained oily substance, the resulting mixture was irradiated with ultrasonic waves, and the precipitated solid was collected, whereby 3.9 g of a white solid was obtained in a yield of 69%. The synthesis scheme of Step 2 is shown below.

[Chemical Formula 48]

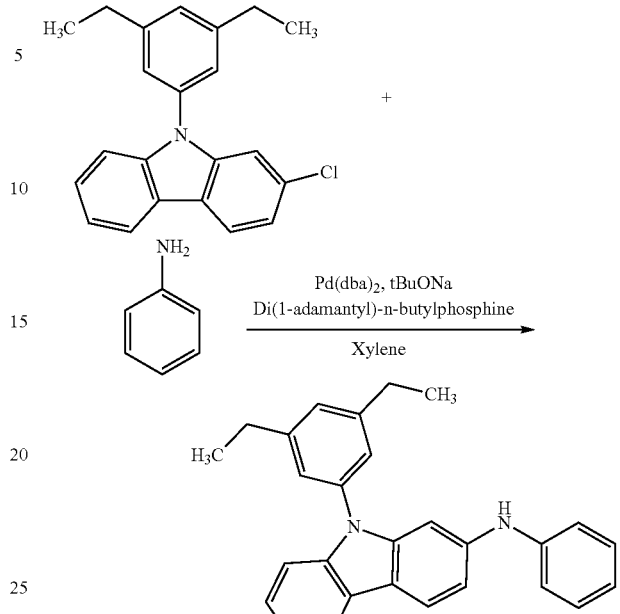

Measurement results obtained by nuclear magnetic resonance (H-NMR) spectroscopy of the white solid obtained in Step 2 are shown below. The results revealed that N-[9-(3,5-diethylphenyl)-9H-carbazol-2-yl]-N-phenylamine was obtained in Step 2.

$^1$H-NMR (DMSO-d$_6$, 300 MHz): 1.25 (t, J1=7.8 Hz, 6H), 2.70 (q, J1=7.8 Hz, 4H), 6.82 (t, J1=7.2 Hz, 1H), 7.00 (dd, J1=8.4 Hz, J2=1.8 Hz, 1H), 7.07 (d, J1=1.8 Hz, 1H), δ=7.12-7.31 (m, 10H), 8.02-8.07 (m, 2H), 8.37 (s, 1H).

Step 3: Synthesis of 3,10mmEtPCA2Nbf(IV)-02

Into a 200-mL three-neck flask were put 0.87 g (2.3 mmol) of 3,10-dichloronaphtho[2,3-b;6,7-b']bisbenzofuran, 2.2 g (5.5 mmol) of N-[9-(3,5-diethylphenyl)-9H-carbazol-2-yl]-N-phenylamine, 82 mg (0.23 mmol) of di(1-adamantyl)-n-butylphosphine, and 1.3 g (14 mmol) of sodium tert-butoxide. To the mixture was added 25 mL of xylene. The mixture was degassed by being stirred while the pressure was reduced. To the mixture was added 26 mg (46 mol) of bis(dibenzylideneacetone)palladium(0), and the mixture was stirred while being heated at 150° C. under a nitrogen stream for 14 hours. After the stirring, toluene was added to the mixture, the mixture was suction-filtered through Florisil, Celite, and alumina, and the filtrate was concentrated to give a solid. The obtained solid was purified by silica gel column chromatography (as the developing solvent, toluene and hexane in a ratio of 1:2 were used) to give a solid. The obtained solid was recrystallized with toluene/ethyl acetate, whereby 1.9 g of a yellow solid was obtained in a yield of 75%. Then, 1.2 g of the obtained solid was sublimated and purified by a train sublimation method. The purification by sublimation was performed by heating at 385° C. under a pressure of 2.2×10$^{-2}$ Pa with an argon flow rate of 0 mL/min. After the purification by sublimation, 0.93 g of a yellow solid was obtained at a collection rate of 78%. The synthesis scheme of Step 3 is shown below.

[Chemical Formula 49]

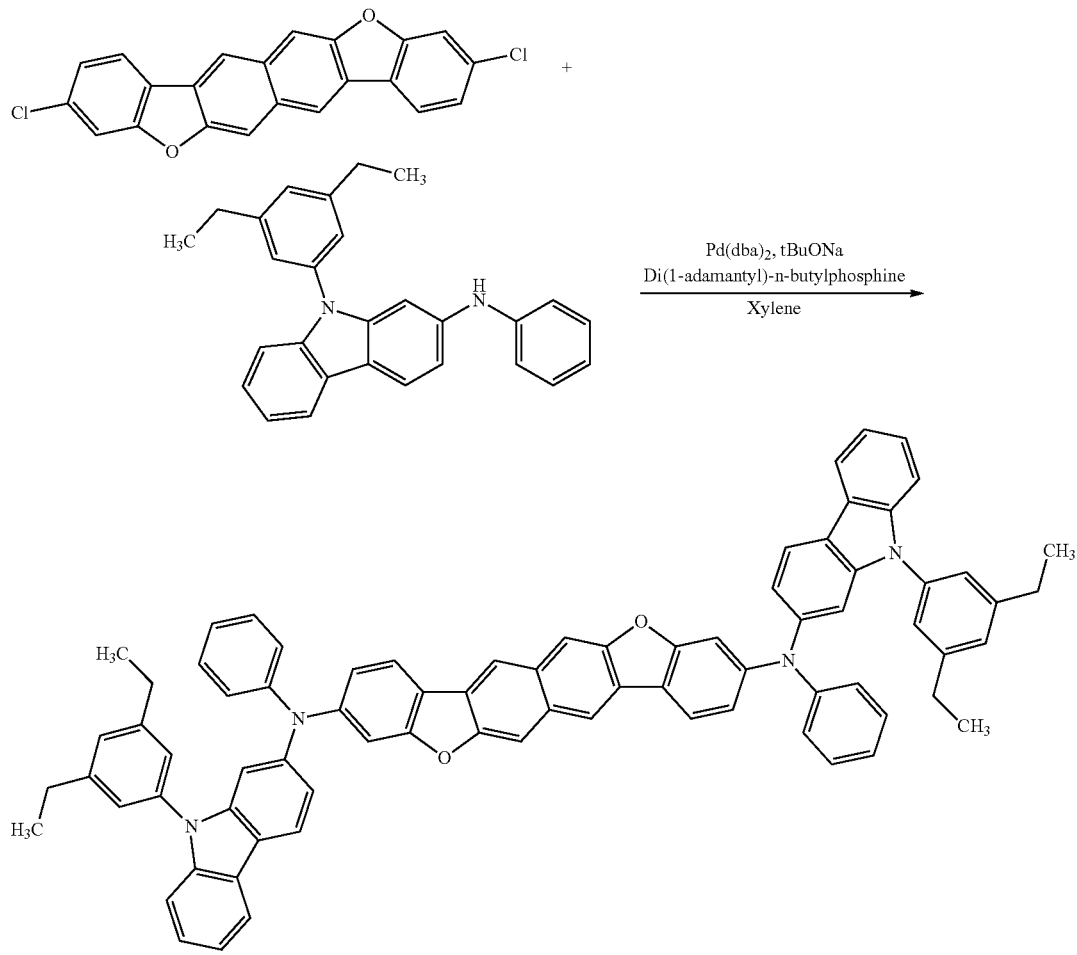

Measurement results obtained by nuclear magnetic resonance ($^1$H-NMR) spectroscopy of the yellow solid obtained in Step 3 are shown below. The results revealed that 3,10mmEtPCA2Nbf(IV)-02 was obtained in Step 3.

$^1$H-NMR (CD$_2$Cl$_2$, 300 MHz): δ=1.12 (t, J1=7.8 Hz, 12H), 2.60 (q, J1=7.8 Hz, 8H), 7.01 (s, 2H), 7.06-7.13 (m, 10H), 7.20-7.44 (m, 18H), 7.89 (d, J1=8.4 Hz, 2H), 7.97 (s, 2H), 8.04-8.10 (m, 4H), 8.36 (s, 2H).

Figure 29:
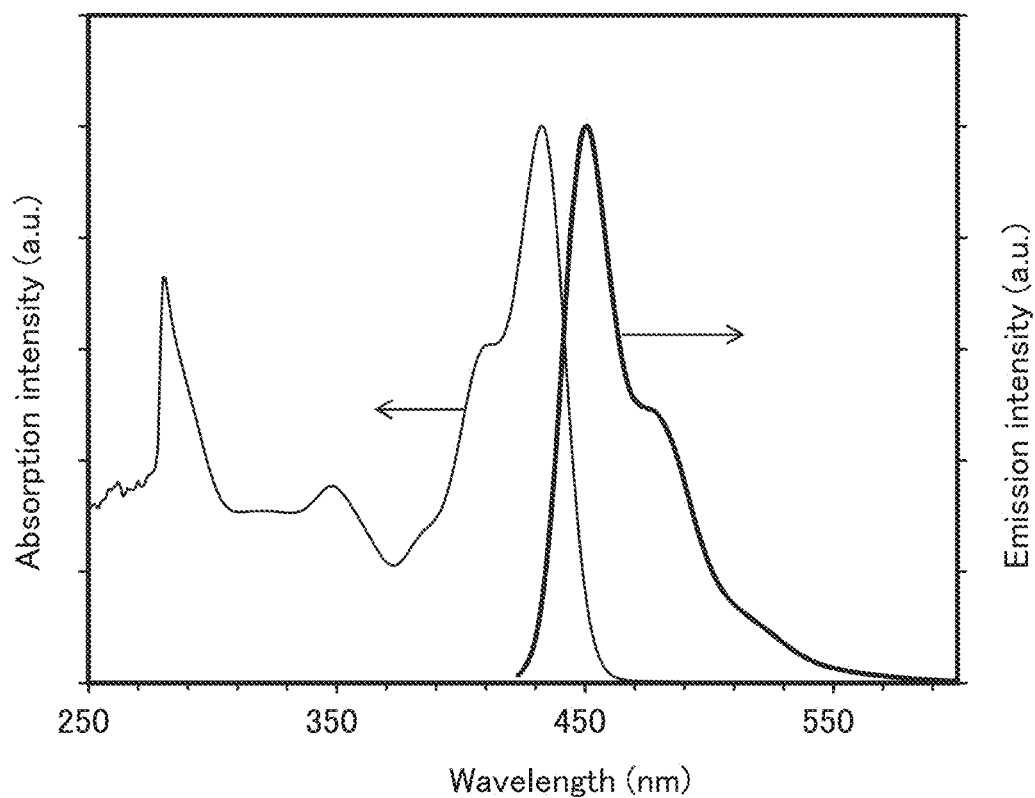
FIG. 29 shows an absorption spectrum and an emission spectrum of 3,10mmEtPCA2Nbf(IV)-02 in a toluene solution.
Figure 30:
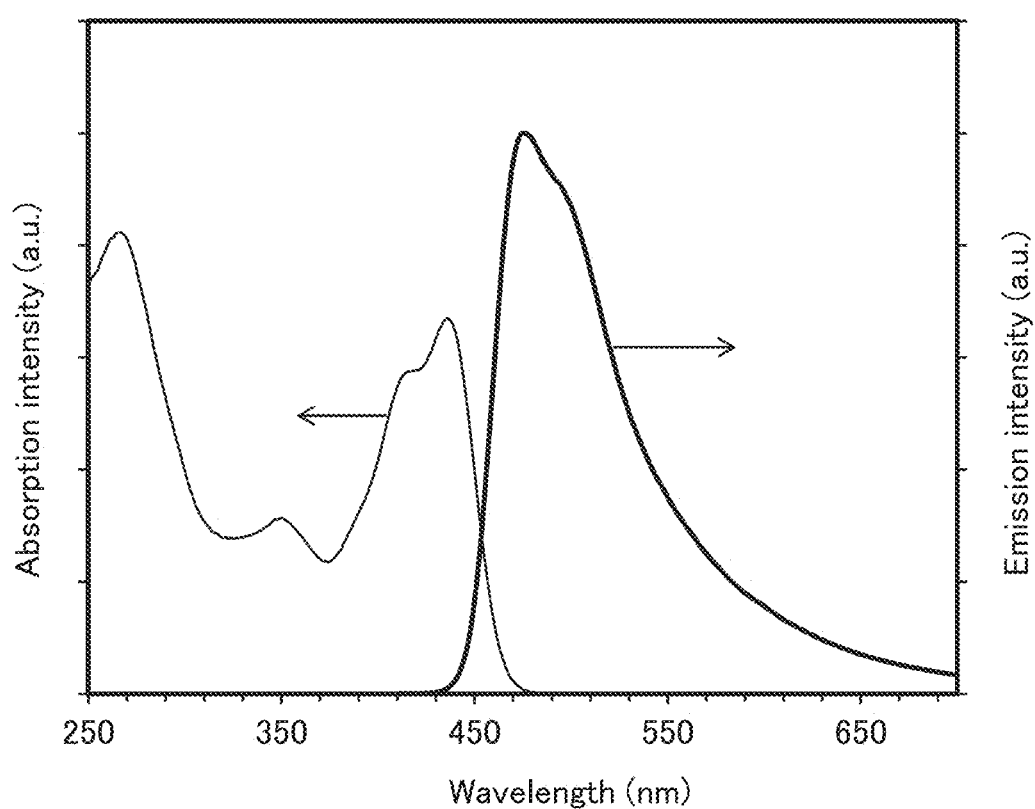
FIG. 30 shows an absorption spectrum and an emission spectrum of 3,10mmEtPCA2Nbf(IV)-02 in a thin film state.

Next, FIG. 29 shows the measurement results of the absorption and emission spectra of 3,10mmEtPCA2Nbf (IV)-02 in a toluene solution. FIG. 30 shows the absorption and emission spectra of a thin film of 3,10mmEtPCA2Nbf (IV)-02. The solid thin film was fabricated over a quartz substrate by a vacuum evaporation method. The absorption spectrum of 3,10mmEtPCA2Nbf(IV)-02 in the toluene solution was measured with an ultraviolet-visible light spectrophotometer (V550, manufactured by JASCO Corporation), and the spectrum of toluene alone in a quartz cell was subtracted. The absorption spectrum of the thin film was measured with a spectrophotometer (U-4100 Spectrophotometer, manufactured by Hitachi High-Technologies Corporation). The emission spectrum was measured with a fluorescence spectrophotometer (FP-8600, manufactured by JASCO Corporation). Quantum yields were measured using an absolute PL quantum yield measurement system (Quantaurus-QY, manufactured by Hamamatsu Photonics K.K.).

FIG. 29 shows that 3,10mmEtPCA2Nbf(IV)-02 in the toluene solution has absorption peaks at 433 nm, 411 nm, 348 nm, 322 nm, and 280 nm, and emission spectrum peaks at 451 nm and 478 nm (excitation wavelength: 408 nm). In addition, FIG. 30 shows that the thin film of 3,10mmEtPCA2Nbf(IV)-02 has absorption peaks at 436 nm, 418 nm, 348 nm, 322 nm, and 280 nm, and an emission spectrum peak at 480 nm (excitation wavelength: 400 nm). These results indicate that 3,10mmEtPCA2Nbf(IV)-02 emits blue light and can be used as a host for a light-emitting substance or a substance that emits fluorescence in the visible region.

The measured quantum yield of 3,10mmEtPCA2Nbf(IV)-02 in the toluene solution was as high as 88%, which indicates that 3,10mmEtPCA2Nbf(IV)-02 is suitable for a light-emitting material.

Reference Example 2

Reference Synthesis Example 2

In this reference synthesis example, a method for synthesizing N,N'-Bis[9-(3,5-diethylphenyl)-9H-carbazol-2-yl]-N, N'-diphenyl-naphtho[2,3-b;6,7-b']bisbenzofuran-3,10-diamine (abbreviation: 3,10mmHexPCA2Nbf(IV)-02), which is used in Example 3, is described. The structural formula of 3,10mmHexPCA2Nbf(IV)-02 is shown below.

[Chemical Formula 50]

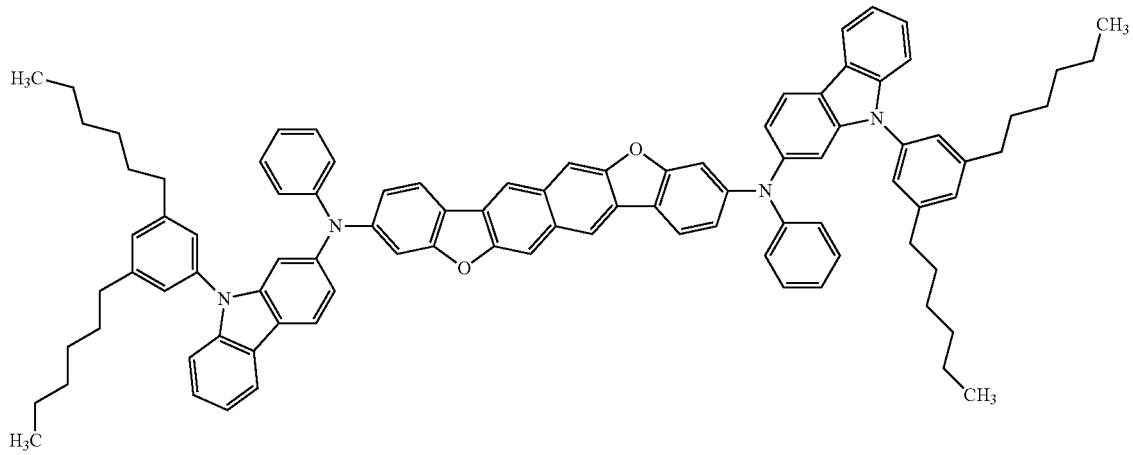

3,10mmHexPCA2Nbf(IV)-02

Step 1: Synthesis of 2-chloro-9-(3,5-dihexylphenyl)-9H-carbazole

Into a 300-mL three-neck flask were put 2.9 g (14 mmol) of 2-chloro-9H-carbazole, 8.4 g (26 mmol) of 1-bromo-3,5-dihexylbenzene, and 4.2 g (43 mmol) of sodium tert-butoxide. To the mixture were added 75 mL of xylene and 0.2 mL of tri(tert-butyl)phosphine (a 10% hexane solution), and the mixture was degassed by being stirred while the pressure was reduced. To the mixture was added 82 mg (10.14 mmol) of bis(dibenzylideneacetone)palladium(0), and the mixture was stirred while being heated at 150° C. under a nitrogen stream for 1.5 hours. After the stirring, toluene was added to the mixture, and the mixture was suction-filtered through Florisil, Celite, and alumina to give a filtrate. The obtained filtrate was concentrated to give an oily substance. The oily substance was purified by silica gel column chromatography (as the developing solvent, hexane was used), whereby 1.4 g of a colorless transparent oily substance was obtained in a yield of 22%. The synthesis scheme of Step 1 is shown below.

[Chemical Formula 51]

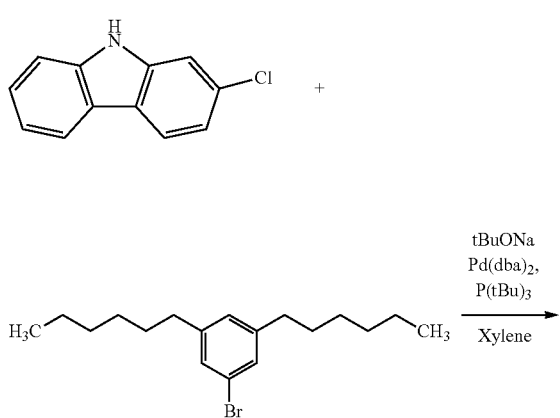

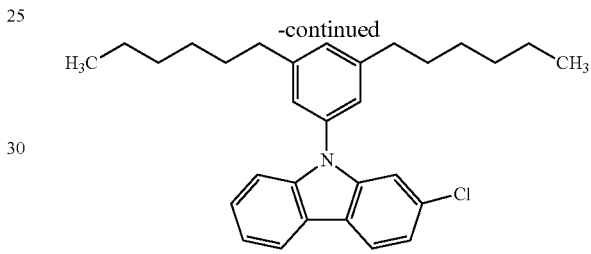

Measurement results obtained by nuclear magnetic resonance ($^1$H-NMR) spectroscopy of the oily substance obtained in Step 1 are shown below. The results revealed that 2-chloro-9-(3,5-dihexylphenyl)-9H-carbazole was obtained in Step 1.

$^1$H-NMR (CDCl$_3$, 300 MHz): δ=0.89 (t, J1=6.9 Hz, 6H), 1.29-1.43 (m, 12H), 1.68 (quin, J1=7.8 Hz, 4H), 2.69 (t, J1=7.8 Hz, 4H), 7.11-7.31 (m, 5H), 7.36-7.44 (m, 3H), 8.03 (d, J1=8.4 Hz, 1H), 8.09 (dt, J1=7.8 Hz, J2=0.9 Hz, 1H).

Step 2: Synthesis of N-[9-(3,5-dihexylphenyl)-9H-carbazol-2-yl]-N-phenylamine Into a 200-mL three-neck flask were put 1.4 g (3.1 mmol) of 2-chloro-9-(3,5-dihexylphenyl)-9H-carbazole, 0.55 g (5.9 mmol) of aniline, 0.90 g (9.4 mmol) of sodium tert-butoxide, and 56 mg (0.16 mmol) of di(1-adamantyl)-n-butylphosphine. To the mixture was added 20 mL of xylene and the mixture was degassed by being stirred while the pressure was reduced. To the mixture was added 18 mg (31 mol) of bis(dibenzylideneacetone)palladium(0), and the mixture was stirred while being heated at 150° C. under a nitrogen stream for 7 hours. After the stirring, toluene was added to the mixture, the mixture was suction-filtered through Florisil, Celite, and alumina, and the filtrate was concentrated to give a brown oily substance.

Into a 200-mL three-neck flask were put 2.7 g (6.1 mmol) of 2-chloro-9-(3,5-dihexylphenyl)-9H-carbazole, 0.85 g (9.1 mmol) of aniline, 1.8 g (18 mmol) of sodium tert-butoxide, and 0.11 g (0.30 mmol) of di(1-adamantyl)-n-butylphosphine. To the mixture was added 30 mL of xylene, and the mixture was degassed by being stirred while the pressure was reduced. To the mixture was added 35 mg (61 mol) of bis(dibenzylideneacetone)palladium(0), and the mixture was stirred while being heated at 150° C. under a nitrogen stream for 7 hours. After the stirring, toluene was added to the mixture, the mixture was suction-filtered through Florisil, Celite, and alumina, and the filtrate was concentrated to give a brown oily substance. Then, two batches of the oily substance were mixed and purified by silica gel column chromatography (as the developing solvent, toluene and hexane in a ratio of 1:4 were used), whereby 1.7 g of a yellow solid was obtained in a yield of 31%. The synthesis scheme of Step 2 is shown below.

[Chemical Formula 52]

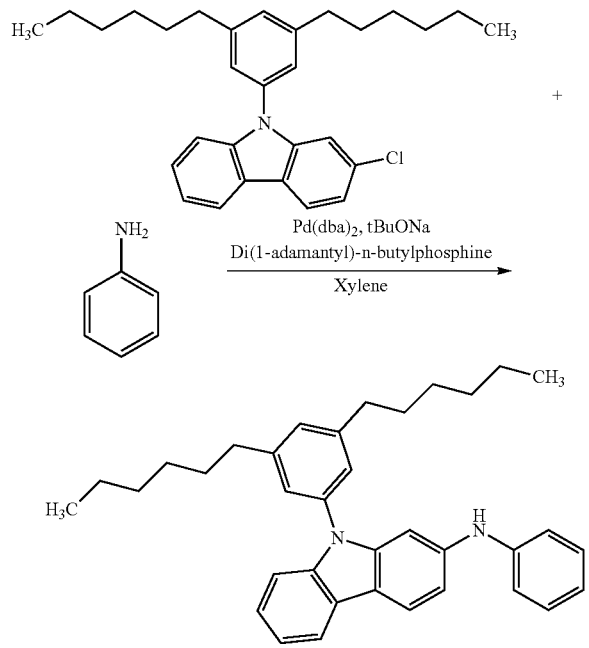

Measurement results obtained by nuclear magnetic resonance ($^1$H-NMR) spectroscopy of the yellow solid obtained in Step 2 are shown below. The results revealed that N-[9-(3,5-dihexylphenyl)-9H-carbazol-2-yl]-N-phenylamine was obtained in Step 2.

$^1$H-NMR (DMSO-$d_6$, 300 MHz): δ=0.84 (t, J1=7.2 Hz, 6H), 1.23-1.35 (m, 12H), 1.62 (quin, J1=7.8 Hz, 4H), 2.66 (t, J1=7.8 Hz, 4H), 6.81 (tt, J1=6.9 Hz, J2=1.2 Hz, 1H), 6.99 (dd, J1=8.7 Hz, J2=1.8 Hz, 1H), 7.07 (d, J1=1.8 Hz, 1H), 7.11-7.15 (m, 3H), 7.18-7.32 (m, 7H), 8.02-8.07 (m, 2H), 8.35 (s, 1H).

Step 3: Synthesis of 3,10mmHexPCA2Nbf(IV)-02

Into a 200-mL three-neck flask were put 0.54 g (1.4 mmol) of 3,10-dichloronaphtho[2,3-b;6,7-b']bisbenzofuran, 1.7 g (3.4 mmol) of N-[9-(3,5-dihexylphenyl)-9H-carbazol-2-yl]-N-phenylamine, 51 mg (0.14 mmol) of di(1-adamantyl)-n-butylphosphine, and 0.83 g (8.6 mmol) of sodium tert-butoxide. To the mixture was added 15 mL of xylene. The mixture was degassed by being stirred while the pressure was reduced. To the mixture was added 16 mg (29 mol) of bis(dibenzylideneacetone)palladium(0), and the mixture was stirred while being heated at 150° C. under a nitrogen stream for 14.5 hours. After the stirring, toluene was added to the mixture, the mixture was suction-filtered through Florisil, Celite, and alumina, and the filtrate was concentrated to give a solid. The obtained solid was purified by silica gel column chromatography (as the developing solvent, toluene and hexane in a ratio of 1:2 were used). The obtained solid was reprecipitated with ethyl acetate/ethanol, whereby 1.7 g of a yellow solid was obtained in a yield of 93%. The synthesis scheme of Step 3 is shown below.

[Chemical Formula 53]

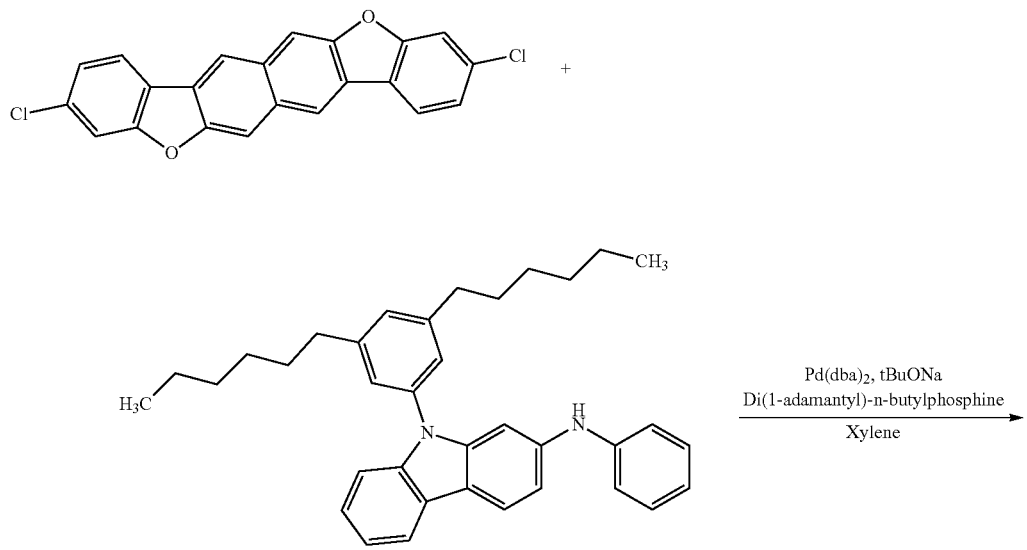

-continued

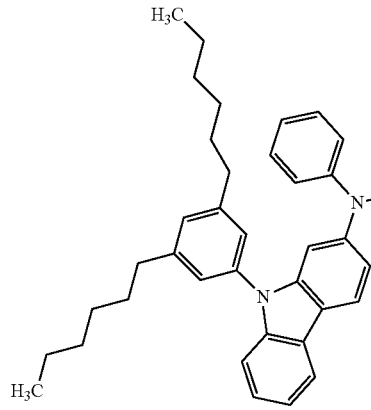
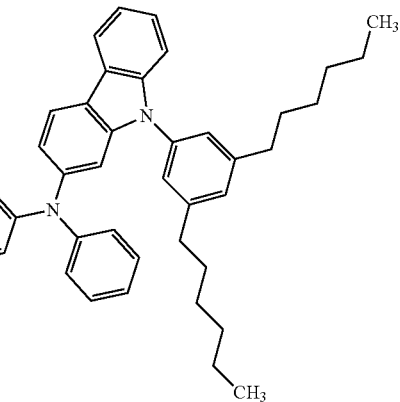

Measurement results obtained by nuclear magnetic resonance ($^1$H-NMR) spectroscopy of the yellow solid obtained in Step 3 are shown below. The results revealed that 3,10mmHexPCA2Nbf(IV)-02 was obtained in Step 3.

$^1$H-NMR (CD$_2$Cl$_2$, 300 MHz): δ=0.83 (t, J1=6.6 Hz, 12H), 1.17-1.31 (m, 24H), 1.47-1.57 (m, 8H), 2.55 (t, J1=7.8 Hz, 8H), 6.98 (s, 2H), 7.06-7.13 (m, 10H), 7.20-7.43 (m, 18H), 7.88 (d, J1=8.4 Hz, 2H), 7.96 (s, 2H), 8.04-8.09 (m, 4H), 8.35 (s, 2H).

This application is based on Japanese Patent Application Serial No. 2019-224653 filed with Japan Patent Office on Dec. 12, 2019, the entire contents of which are hereby incorporated by reference.

What is claimed is:

1. An organic compound represented by Formula (G1),

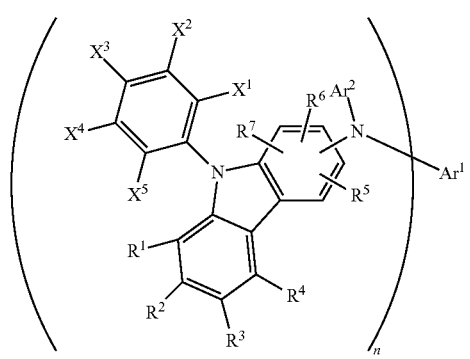

(G1)

wherein:
one of $X^1$ to $X^5$ is a secondary or tertiary alkyl group having 3 to 6 carbon atoms, wherein one of the 3 to 6 carbon atoms is a branched carbon atom bonded to the phenyl group;
each of the others of $X^1$ to $X^5$ is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms;
each of $R^1$ to $R^7$ is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms;
$Ar^1$ represents a substituted or unsubstituted condensed heteroaromatic ring skeleton having 8 to 60 carbon atoms and including two or more aromatic rings;
$Ar^2$ represents a substituted or unsubstituted aryl group having 6 to 25 carbon atoms;
n is 2; and
the groups bonded to $Ar^1$ are the same or different from each other.

2. The organic compound according to claim 1, wherein $Ar^1$ includes 3 to 9 aromatic rings.

3. The organic compound according to claim 1, wherein $Ar^1$ includes 3 to 7 aromatic rings.

4. The organic compound according to claim 1, wherein the one of $X^1$ to $X^5$ is the secondary or tertiary alkyl group having 3 or 4 carbon atoms.

5. The organic compound according to claim 1, wherein $Ar^1$ is any of heteroaromatic ring skeletons represented by Formulae (B1) to (B4),

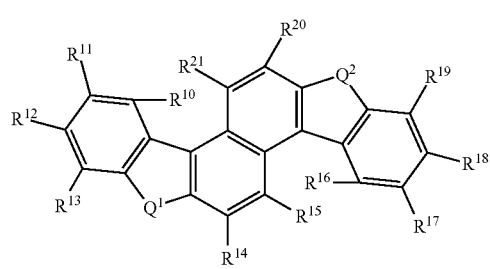

(B1)

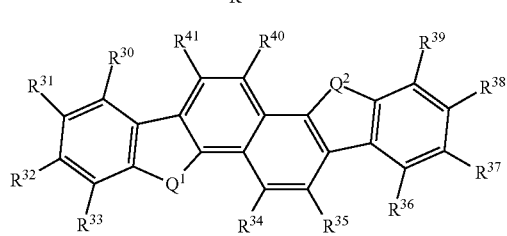

(B2)

-continued (B3)

(B4)

wherein in Formulae (B1) to (B4):
  each of Q¹ and Q² independently represents an oxygen atom or a sulfur atom, wherein in Formula (B1):
  two of $R^{10}$ to $R^{21}$ represent a single bond connected to the nitrogen atom; and
  each of the others of $R^{10}$ to $R^{21}$ independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms, wherein in Formula (B2):
  two of $R^{30}$ to $R^{41}$ represent a single bond connected to the nitrogen atom; and
  each of the others of $R^{30}$ to $R^{41}$ independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms, wherein in Formula (B3):
  two of $R^{50}$ to $R^{61}$ represent a single bond connected to the nitrogen atom; and
  each of the others of $R^{50}$ to $R^{61}$ independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms, and wherein in Formula (B4):

two of $R^{70}$ to $R^{81}$ represent a single bond connected to the nitrogen atom; and
  each of the others of $R^{70}$ to $R^{81}$ independently represents any of hydrogen, an alkyl group having 1 to 6 carbon atoms, a cycloalkyl group having 3 to 12 carbon atoms, and an unsubstituted or alkyl-substituted aryl group having 6 to 13 carbon atoms.

6. The organic compound according to claim 1, wherein $Ar^1$ is a heteroaromatic ring skeleton represented by Formula (B1-1) or (B3-1), (B1-1)

(B3-1)

wherein each of Q¹ and Q² independently represents an oxygen atom or a sulfur atom, and
wherein each of $R^{12}$, $R^{18}$, $R^{52}$, and $R^{58}$ represents a single bond connected to the nitrogen atom.

7. An organic compound represented by Formula (G1-1), (G1-1)

wherein:
  one of $X^{11}$ to $X^{15}$ is a secondary or tertiary alkyl group having 3 to 6 carbon atoms, wherein one of the 3 to 6 carbon atoms is a branched carbon atom bonded to the phenyl group;
  each of the others of $X^{11}$ to $X^{15}$ is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms;
  one of $X^{21}$ to $X^{25}$ is a secondary or tertiary alkyl group having 3 to 6 carbon atoms, including a branched carbon atom bonded to the phenyl group;

each of the others of $X^{21}$ to $X^{25}$ is independently any of hydrogen, an alkyl group having 1 to 6 carbon atoms, a cycloalkyl group having 3 to 12 carbon atoms, and an unsubstituted or alkyl-substituted aryl group having 6 to 13 carbon atoms; and each of $Ar^{21}$ and $Ar^{22}$ independently represents a substituted or unsubstituted aryl group having 6 to 25 carbon atoms.

8. A light-emitting device comprising the organic compound according to claim 1.

9. An optical device comprising the organic compound according to claim 1.

10. An electronic device comprising:
the light-emitting device according to claim 8; and
at least one of a sensor, an operation button, a speaker, and a microphone.

11. A light-emitting apparatus comprising:
the light-emitting device according to claim 8; and
at least one of a transistor and a substrate.

12. A lighting device comprising:
the light-emitting device according to claim 8; and
a housing.

13. A light-emitting device comprising the organic compound according to claim 7.

14. An optical device comprising the organic compound according to claim 7.

15. An electronic device comprising:
the light-emitting device according to claim 13; and
at least one of a sensor, an operation button, a speaker, and a microphone.

16. A light-emitting apparatus comprising:
the light-emitting device according to claim 13; and
at least one of a transistor and a substrate.

17. A lighting device comprising:
the light-emitting device according to claim 13; and
a housing.

* * * * *